(12) United States Patent
Dunlop et al.

(10) Patent No.: US 8,221,755 B2
(45) Date of Patent: *Jul. 17, 2012

(54) MONOCLONAL ANTIBODY AGAINST INTERLEUKIN-13 RECEPTOR ALPHA 1 (IL-13RALPHA1)

(75) Inventors: Felicity Meredith Dunlop, Regent (AU); Manuel Baca, Viewbank (AU); Andrew Donald Nash, Kew (AU); Louis Jerry Fabri, Diamond Creek (AU); Douglas James Hilton, Warrandyte (AU); Nicos A. Nicola, Mont Albert (AU)

(73) Assignee: Zenyth Operations Pty Ltd., Richmond, Victoria (AU)

( * ) Notice: Subject to any disclaimer, the term of this patent is extended or adjusted under 35 U.S.C. 154(b) by 0 days.

This patent is subject to a terminal disclaimer.

(21) Appl. No.: 12/828,589

(22) Filed: Jul. 1, 2010

(65) Prior Publication Data

US 2011/0020363 A1    Jan. 27, 2011

Related U.S. Application Data

(63) Continuation of application No. 10/850,270, filed on May 20, 2004, now Pat. No. 7,785,590, which is a continuation of application No. PCT/AU03/00352, filed on Mar. 21, 2003.

(30) Foreign Application Priority Data

Mar. 22, 2002 (AU) .................................. 1301/02
Feb. 3, 2003 (AU) ................................ 2003900437

(51) Int. Cl.
*A61K 39/395* (2006.01)
(52) U.S. Cl. ................................. 424/144.1; 530/388.22
(58) Field of Classification Search ........................ None
See application file for complete search history.

(56) References Cited

U.S. PATENT DOCUMENTS

| 5,859,205 A * | 1/1999 | Adair et al. ................ 530/387.3 |
| 5,919,456 A | 7/1999 | Puri et al. |
| 6,143,871 A | 11/2000 | Bonnefoy et al. |
| 6,911,530 B1 | 6/2005 | Willson et al. |
| 7,785,590 B2 * | 8/2010 | Dunlop et al. ............. 424/133.1 |

FOREIGN PATENT DOCUMENTS

| JP | 11-514873 | 12/1999 |
| JP | 2000-511042 | 8/2000 |
| JP | 2003-547458 | 4/2005 |
| WO | 90/07861 A1 | 7/1990 |
| WO | 97/15663 | 5/1997 |
| WO | 97/15663 A1 | 5/1997 |
| WO | 98/10638 | 3/1998 |
| WO | 03/046009 | 6/2003 |
| WO | 2008060814 A2 | 5/2008 |

OTHER PUBLICATIONS

Eduardo Padlan, Mol Immunol. Feb. 1994;31(3):169-217.*
Portolano et al., J Immunol. Feb. 1, 1993;150(3):880-7.*
Damschroder et al., Mol Immunol. Aug. 2004;41(10):985-1000.*
Humphreys et al., Current Opinion in Drug Discovery & Development 2001 4(2):172-185.*
Zurawski, G. et al., "Interleukin 13, an Interleukin 4-like Cytokine That Acts on Monocytes and B-Cells, but Not on T Cells" *Immunology Today* (1994) pp. 19-26, vol. 15(1).
Endo, T. et al., "LPS-Dependent Cyclooxygenase-2 Induction in Human Monocytes is Down-Regulated by IL-13, but Not by IFN-Gamma" *Journal of Immunology* (1996) pp. 2240-2246, vol. 156(6).
Poudrier, J. et al., "A Novel Monoclonal Antibody, C41, Reveals IL-13Rα1 Expression by Murine Germinal Center B Cells and Follicular Dendritic Cells", *European Journal of Immunology*, 30(11):3157-3164 (2000).
Vermot-Desroches, C. et al., "Identification and Characterization of Abs Anti-IL-13 Rα1 or Anti-IL-13 Rα2", *Tissue Antigens*, 55(1):52-53 (2000), abstract H.25.
Graber, P. et al., "The Distribution of IL-13 Receptor α1 Expression on B Cells, T Cells and Monocytes and its Regulation by IL-13 and IL-4", *European Journal of Immunology*, 28(12): 42864298 (1998).
Clement, C. et al., "Monoclonal Antibodies Against the Interleukin-13 Receptor α1 and α2", *Cytokine*, 9(11):959 (1997), abstract 280.
Shan, H. et al., "The Mechanism of Autoantibody Production in an Autoimmune MRL/lpr Mouse", *The Journal of Immunology*, 153(11):5104-5120 (1994) and Database Gen Pept, Accession No. AAB32552.
Database PIR, Accession No. S20708 (1992).
Akaiwa M. et al., "Localization of Human Interleukin 13 Receptor in Non-haematopoietic Cells", *Cytokine* 13(2): 75-84 (2001).
Hershey G. K. K, "IL-13 receptors and signaling pathways: An evolving web", *Journey of Allergy and Clinical Immunology* 111(4): 677-690 (2003).
English-Language Translation of an Official Action from the Japanese Patent Office, dated Oct. 1, 2008, issued in corresponding Japanese Patent Application No. 2003-578428.
United States Patent Application Publication No. US 2005/0154192 A1, published Jul. 14, 2005 to Shirakawa et al., corresponding to Japanese Patent Application No. 2003-547458.
United States Patent Application Publication No. US 2002/0045741 A1, published Apr. 18, 2002 to Willson et al., corresponding to Japanese Patent Application No. 11-514873.
Janeway et al., *Immunobiology*, 5th Ed., Garland Science, pp. 94-105 (2001).
Moy et al., *Journal of Molecular Biology* (2001) pp. 219-230, vol. 310(1).

(Continued)

*Primary Examiner* — Zachary Skelding
(74) *Attorney, Agent, or Firm* — Scully, Scott, Murphy & Presser, P.C.

(57) ABSTRACT

The present invention relates generally to antibodies that bind to the Interleukin-13 receptor.alpha.1 chain (IL-13R.alpha.1) and antagonize IL-13 receptor-mediated signaling by IL-13 and/or IL-4. More particularly, the present invention provides humanized or human antibodies to mammalian and in particular IL-13R.alpha.1. These antibodies have uses in the treatment or prevention of IL-13- and/or IL-4-mediated diseases or conditions. The present invention further contemplates a method of modulating IL-13- and/or IL-4-mediated diseases or conditions by the administration of the subject antibodies. The present invention further provides an assay system useful for identifying antibodies or other agents which modulate IL-13 and/or IL-4 signaling through an IL-13 receptor complex. Accordingly, a method of screening for modulators of IL-13R.alpha.1/ligand interaction is also provided.

4 Claims, 11 Drawing Sheets

OTHER PUBLICATIONS

Kawakami et al., *Blood* (2001) pp. 2673-2679, vol. 97(9).
Obiri et al., *Journal of Immunology* (1997) pp. 756-765, vol. 158(2).
Aman et al., *Journal of Biological Chemistry* (1996) pp. 29265-29270, vol. 271(46).
Caput et al., *Journal of Biological Chemistry* (1996) pp. 16921-16926, vol. 271(28).
Murata et al., *Blood* (1998) pp. 3884-3891, vol. 91(10).
Tang et al., *Vet Immunopathology* (2001) pp. 181-195, vol. 79(3-4).
Trigona et al., *Vet Immunopathology* (999) pp. 73-79, vol. 72(1-2).
Hilton et al., *Proc National Academy of Science in USA* (1996) pp. 497-450, vol. 93(1).
Pierrot et al., *Biochem Biophys Res Communication* (2001) pp. 969-976, vol. 287(4).
Vajdos et al., *Journal of Molecular Biology* (2002) pp. 415-428, vol. 320(2).
Rudikoff et al., *Proc National Academy of Science in USA* (1982) pp. 1979-1983, vol. 79.
Chien et al., *Proc National Academy of Science in USA* (1989) pp. 5532-5536, vol. 86(14).
Whitty et al., *Chemical Biology* (1999) pp. R107-R118, vol. 6(4).
Huang, Z., *Pharmacological Therapy* (2002) pp. 201-215, vol. 86(3).
Colman, P.M., *Research in Immunology* (1994) pp. 33-36, vol. 145.
Arima, K. et al., "Characterization of the Interaction between Interleukin-13 and Interleukin-13 Receptors" The Journal of Biological Chemistry (2005) pp. 24915-24922, vol. 280, No. 26.

* cited by examiner

$V_L$ domain

```
                10              20        abcde 30              40
Mu.1D9    DILMTQAAFSNPVTLGTSASISCRSSKSLLHSNGITYLYWYLQKP
HuV_LkI   DIQMTQSPSSLSASVGDRVTITC---------------WYQQKP
          |         FR1          |      CDR1     |

50              60              70              80
Mu.1D9    GQSPQLLIYQMSNLASGVPDRFSCSGSGTDFTLSISRVEA
HuV_LkI   GKAPKLLIY------GVPSRFSGSGSGTDFTLTISSLQP
              FR2    | CDR2  |        FR3

90             100
Mu.1D9    EDVGFYYCAQNLELPFTFGSGTKLEIE
HuV_LkI   EDFATYYC--------FGQGTKVEIK
                  |  CDR3   |  FR4
```

$V_H$ domain

```
                10              20              30              40
Mu.1D9    EVKLVESGGGLVKPGGSLKLSCAASGFTFSGYGMSWVRQT
HuV_HIII  EVQLVESGGGLVQPGGSLRLSCAAS-----------WVRQA
          |         FR1          |      CDR1     |

50        a     60              70              80
Mu.1D9    PEKRLEWVATISGLGGYTYYPDSVKGRFTISRDNAKNTLYL
HuV_HIII  PGKGLEWVA-----------------RFTISRDNSKNTLYL
            FR2     |       CDR2        |      FR3 abc       90        100abcd       110
Mu.1D9    QMSSLRSDDTAFYYCARRFYGDYVGAMDYWGQGTSVTVSS
HuV_HIII  QMNSLRAEDTAVYYCAR-----------WGQGTLVTVSS
                           |    CDR3    |  FR4
```

Figure 10

MONOCLONAL ANTIBODY AGAINST INTERLEUKIN-13 RECEPTOR ALPHA 1 (IL-13RALPHA1)

RELATED APPLICATIONS

This application is a continuation of U.S. patent application Ser. No. 10/850,270, filed May 20, 2004, which is a continuation of PCT Application No. PCT/AU03/00352, filed on Mar. 21, 2003 the entire content and disclosure of which is incorporated herein by reference.

BACKGROUND OF THE INVENTION

1. Field of the Invention

The present invention relates generally to antibodies that bind to the Interleukin-13 receptor al chain (IL-13Rα1) and antagonize IL-13 receptor-mediated signaling by IL-13 and/or IL-4. More particularly, the present invention provides humanized or human antibodies to mammalian and in particular IL-13Rα1. These antibodies have uses in the treatment or prevention of IL-13- and/or IL-4-mediated diseases or conditions. The present invention further contemplates a method of modulating IL-13- and/or IL-4-mediated diseases or conditions by the administration of the subject antibodies. The present invention further provides an assay system useful for identifying antibodies or other agents which modulate IL-13 and/or IL-4 signaling through an IL-13 receptor complex. Accordingly, a method of screening for modulators of IL-13Rα1/ligand interaction is also provided.

2. Description of the Prior Art

Bibliographic details of the publications referred to in this specification are also collected at the end of the description.

Reference to any prior art in this specification is not, and should not be taken as, an acknowledgment or any form of suggestion that this prior art forms part of the common general knowledge in any country.

Interleukin-13 (IL-13) is a member of the interleukin (IL) family whose biological effects have significant physiological implications since both up- and down-regulation of activity of this cytokine in vivo could potentially provide pharmacological treatments for a wide range of common pathologies. For this reason, amongst others, the study of IL-13 and other IL molecules is of great medical importance. For example, IL-13 is strongly involved in the induction of IgE and IgG4 production as well as the differentiation of T-helper (Th) cells into a secretory (Th2) phenotype. These immunostimulatory steps are critical in the development of atopic diseases which are a major threat to human health, such as anaphylaxis (Howard et al., *Am J Hum Genet.* 70(1): 230-236, 2002; Noguchi et al., *Hum Immunol* 62(11): 1251-1257, 2001) as well as milder conditions such as hay fever, allergic rhinitis and chronic sinusitis which, although not life-threatening, are responsible for considerable morbidity worldwide.

IL-13 is a mediator in the pathology of the acute and chronic stages of asthma. During an asthma attack, its activity increases and its effects include reduction of the capacity of lung epithelial cells to maintain a tight barrier against inhaled particles and pathogens (Ahdieh et al., *Am J. Physiol. Cell Physiol.* 281(6): C2029-2038, 2000) and promotion of allergen-induced airway hyper-responsiveness (Morse et al., *Am. J. Physiol. Lung Cell Mol. Physiol.* 282(1): L44-49, 2002). In the longer term, IL-13 promotes non-inflammatory structural changes to asthmatic airways, such as enhanced expression of mucin genes, airway damage and obstruction of the small airways (Howard et al., *Am. J. Hum. Genet.* 70(1): 230-236, 2002; Danahay et al., *Am. J. Physiol. Lung Cell Mol. Physiol.* 282(2): L226-236, 2002).

Up-regulation of IL-13 activity may be beneficial in certain immune deficiency conditions to reduce disease progression. In HIV infection, for example, a reduction in secretion by Th2 cells reduces antigen-specific immune responses (Bailer et al., *J. Immunol.* 162(12): 7534-7542, 1999). IL-13, whose levels gradually decline in accordance with disease progression in HIV, has been found to enhance antigen presentation in immune deficiency conditions and to reduce de novo HIV-infection of macrophages (Bailer et al., *Eur. J. Immunol.* 30(5): 1340-1349, 2000).

The biological effects of IL-13 are mediated by a dimeric receptor complex comprising the subunits IL-13Rα1 (or the NR4 subunit) and IL-4Rα. It is postulated that IL-13 binding to IL-13Rα1 triggers dimerization with IL-4Rα and activation of intracellular mediators that include the Janus Kinases JAK1 and JAK2, as well as STAT6, ERK and p38 (David et al., *Oncogene* 20(46): 6660-6668, 2001; Perez et al., *J. Immunol.* 168(3): 1428-1434, 2002).

IL-13 shows many overlapping biological effects with those of IL-4. IL-13 and IL-4 are related by sequence and are involved in many related processes, such as myelopoiesis and the regulation of monocyte/macrophage pro-inflammatory functions. For example, both IL-13 and IL-4 have been shown to effect B cells in a similar fashion, up-regulating surface molecules such as MHC class II and CD23 molecules, and promoting the secretion of IgG4 and IgE.

The overlapping activities of IL-13 and IL-4 can be explained in part by their shared dimeric receptor complex. The Type I IL-13 receptor complex is comprised of an IL-13Rα1 and an IL-4Rα; this same receptor complex is also the Type II IL-4 receptor complex (Callard et al., *Immunology Today* 17(3): 108, 1996). As such, in looking to achieve therapeutic control of the IL-13 receptor complex by blocking cytokine mediated signaling, it may be useful to have not only a molecule that antagonized signaling mediated by IL-13, but a molecule that antagonized signaling mediated by both IL-13 and IL-4.

Antibodies to IL-13Rα1 may potentially act as antagonists of IL-13-signaling through IL-13 receptor complex. International Patent Publication No. WO 97/15663 suggests antibodies to human IL-13Rα1 as potential therapeutic agents. Gauchat et al. (*Eur. J. Immunol.* 28: 4286-4298, 1998) reported murine antibodies to human IL-13Rα1 which blocked interaction of a tagged IL-13 with a tagged and immobilized soluble IL-13Rα1. The antibodies also inhibited IL-13 binding to IL-13Rα1 in transfected HEK-293 cells. However, all of these antibodies failed to neutralize IL-13 induced biological activity, suggesting that they were not antagonists of the complete IL-13Rα1/IL-4Rα receptor complex. In a later paper, Gauchat et al. (*Eur. J. Immunol.* 30: 3157-3164, 2000) reported a rat antibody, designated as C41, to murine IL-13Rα1 which bound to HEK-293 cells transfected with murine IL-13Rα1. However, C41 did not neutralize IL-13 induced biological activities. Further, C41 did not react with the soluble form of human IL-13Rα1. Akaiwa et al. (*Cytokine* 13: 75-84, 2001) reported an antibody that recognized soluble IL-13Rα1 by enzyme immunoassay and a tagged full length IL-13Rα1 transfected into COST cells. The antibody was used for immunohistochemistry but there is no indication as to whether it was a neutralizing antibody.

In accordance with the present invention, antibodies are generated which bind to the IL-13Rα1 chain, block IL-13 binding to the IL-13Rα1 chain and which antagonize IL-13 signaling through the IL-13Rα1/IL-4Rα complex. Such antibodies are proposed to inhibit IL-13 mediated biological activity. In a preferred embodiment, some antibodies of the present invention surprisingly antagonize signaling by both IL-13 and IL-4 through the IL-13Rα1/IL-4Rα complex.

SUMMARY OF THE INVENTION

Throughout this specification, unless the context requires otherwise, the word "comprise", or variations such as "comprises" or "comprising", will be understood to imply the inclusion of a stated element or integer or group of elements or integers but not the exclusion of any other element or integer or group of elements or integers.

Nucleotide and amino acid sequences are referred to by a sequence identifier number (SEQ ID NO:). The SEQ ID NOs: correspond numerically to the sequence identifiers <400>1 (SEQ ID NO:1), <400>2 (SEQ ID NO:2), etc. A summary of the sequence identifiers is provided in Table 1. A sequence listing is provided after the claims.

The present invention provides antibodies that function as IL-13Rα1 antagonists and may be used for treating certain conditions induced by IL-13. The present invention also provides methods for treating these conditions comprising administering an IL-13Rα1 antagonist to a patient afflicted with such a condition. Also provided are compositions for use in such methods comprising one or more IL-13Rα1 antagonists.

The IL-13Rα1 chain may be from any animal, including a mammal such as a human. Preferred IL-13Rα1 chains are the human IL-13Rα1 chain, the murine IL-13Rα1 chain, the rat IL-13Rα1 chain, the canine IL-13Rα1 chain, the ovine IL-13Rα1 chain or the cynamologus monkey IL-13Rα1 chain. Preferably, the IL-13Rα1 chain is the human IL-13Rα1 chain. There is a high level of sequence homology between IL-13Rα1 chains from different species. For example, ovine IL-13Rα1 has 87% homology at the amino acid level and 88.7% homology at the DNA level to human IL-13Rα1. Ovine IL-13Rα1 has 75% homology at the amino acid level and 82.2% homology at the DNA level to murine IL-13Rα1. Human IL-13Rα1 has 75% homology at the amino acid level and 81.3% homology at the DNA level to murine IL-13Rα1. Consequently, the present invention contemplates an IL-13Rα1 chain or its equivalent from any source such as an IL-13Rα1 having at least about 65% identity to human IL-13Rα1 after optimal alignment. The antibodies of the present invention bind, interact or otherwise associate to the IL-13Rα1 or a portion thereof. The antibodies may be specific for IL-13Rα1 from a particular species, such as human IL-13Rα1, or, in view of the level of sequence similarity between IL-13Rα1 from different species, the antibodies may show some cross-reactivity with IL-13Rα1 from two or more species. In the case of antibodies directed towards human IL-13Rα1, some level of cross-reactivity with other mammalian forms of IL-13Rα1 may be desirable in certain circumstances, such as for example, for the purpose of testing antibodies in animal models of a particular disease and for conducting toxicology studies in a manner where IL-13 and/or IL-4 signaling in the test animal is affected by the test antibody. Species where cross-reactivity of an antibody to human IL-13Rα1 may be desirable include monkey, sheep, dog and rat. Accordingly, one preferred group of antibodies are those which exhibit some level of species cross-reactivity. A particularly preferred group of such antibodies are those to human IL-13Rα1 which exhibit some level of species cross-reactivity.

Antibodies of the present invention include, but are not limited to, antibodies that bind IL-13Rα1 and inhibit IL-13 induced signaling through the IL-13 receptor complex, and other compounds that inhibit a biological effect that results from the binding of IL-13 to a cell surface IL-13 receptor. A preferred group of antibodies are those that inhibit signaling by both IL-13 and IL-4 through the IL-13 receptor complex.

Preferably, the antibodies are monoclonal antibodies or antigen-binding fragments thereof. Most preferably, the antibodies are humanized or human antibodies suitable for administration to humans. These include humanized antibodies prepared, for example, from murine monoclonal antibodies and human monoclonal antibodies which may be prepared, for example, using transgenic mice or by phage display.

Antibodies in accordance with the present invention include the murine monoclonal antibody 1D9, and humanized forms of mAb 1D9.

The present invention contemplates methods of modulating IL-13- and/or IL-4-mediated diseases or conditions by the administration of antibodies of the present invention. Conditions to be treated in accordance with the present invention include fibrosis, Hodgkin's disease, ulcerative colitis, scleroderma, lung disorders such as asthma and chronic obstructive pulmonary disease, allergic rhinitis, oncological conditions, inflammatory bowel disease and other inflammatory conditions in the gastrointestinal tract, allergic reactions to medication and any other IL-13 mediated diseases or conditions.

The present invention also provides an assay system useful for identifying antibodies or other agents which modulate IL-13 and/or IL-4 signaling through an IL-13 receptor complex. Accordingly, a method of screening for modulators of IL-13Rα1/ligand interaction, which method involves the assay system, is provided.

A hybridoma producing murine monoclonal antibody 1D9 was deposited on Mar. 21, 2003 at the European Collection of Cell Cultures (ECACC), Centre for Applied Microbiology and Research, Porton Down, Salisbury, United Kingdom, under Accession No. 03032101 on Mar. 21, 2003.

A summary of sequence identifiers used throughout the subject specification is provided in Table 1.

TABLE 1

Summary of sequence identifiers

| SEQUENCE ID NO: | DESCRIPTION |
|---|---|
| 1 | Nucleotide sequence encoding IL-4Rα |
| 2 | Amino acid sequence of IL-4Rα |
| 3 | Nucleotide sequence encoding human IL-13Rα1 |
| 4 | Amino acid sequence of human IL-13Rα1 |
| 5 | Nucleotide sequence encoding gp130 |
| 6 | Amino acid sequence of gp130 |
| 7 | Nucleotide sequence encoding IL-4Rα-gp130 fusion |
| 8 | Amino acid sequence of IL-4Rα-gp130 fusion |
| 9 | Nucleotide sequence encoding IL-13Rα1-gp130 fusion |
| 10 | Amino acid sequence of IL-13Rα1-gp130 fusion |
| 11 | IL-13Rα1 5' oligonucleotide |
| 12 | IL-13Rα1 3' oligonucleotide |
| 13 | gp130 5' oligonucleotide |
| 14 | gp130 3' oligonucleotide |
| 15 | IL-4Rα 5' amplification oligonucleotide |
| 16 | IL-4Rα 3' amplification oligonucleotide |
| 17 | IL-4Rα 5' oligonucleotide |
| 18 | IL-4Rα 3' oligonucleotide |
| 19 | Amino acid sequence of murine 1D9 CDR1 in $V_L$ domain |
| 20 | Amino acid sequence of murine 1D9 CDR2 in $V_L$ domain |
| 21 | Amino acid sequence of murine 1D9 CDR3 in $V_L$ domain |
| 22 | Amino acid sequence of murine 1D9 CDR1 in $V_H$ domain |
| 23 | Amino acid sequence of murine 1D9 CDR2 in $V_H$ domain |
| 24 | Amino acid sequence of murine 1D9 CDR3 in $V_H$ domain |

TABLE 1-continued

Summary of sequence identifiers

| SEQUENCE ID NO: | DESCRIPTION |
|---|---|
| 25 | Amino acid sequence of murine 1D9 CDR regions from $V_L$ domain grafted onto human consensus framework |
| 26 | Amino acid sequence of murine 1D9 CDR region from $V_H$ domain grafted onto human consensus framework |
| 27 | Amino acid sequence of $V_L$ domain of murine 1D9 |
| 28 | Amino acid sequence of $V_H$ domain of murine 1D9 |

BRIEF DESCRIPTION OF THE FIGURES

FIG. 10 is a representation of the amino acid sequence of murine mAb ID9 variable domains and human consensus framework. Sequence numbering is according to Kabat et al., (*Sequences of Proteins of Immunological Interest*, 5$^{th}$ Ed., 1991, ed. Bethesda: Public Health Services, National Institutes of Health) and key framework residues are indicated by bullets (Baca et al., *J. Biol. Chem.* 272(16): 10678-10684, 1997). CDR sequences are underlined and are defined according to the sequence definition of Kabat et al. (1991, supra) with the exception of CDR-H1, which is the combined sequence and structural definition (Chothia et al., *Nature* 342(6252): 877-883, 1989). The framework is the consensus sequence for the human light chain K subgroup I-heavy chain subgroup III (Chuntharapai et al., *Cytokine* 15(5): 250-260, 2001). The sequences shown correspond to the following sequence identifiers:

| | |
|---|---|
| $V_L$ Domain Mu. 1D9 | SEQ ID NO: 27 |
| $V_L$ Domain Hu$V_L$KI | SEQ ID NO: 25 |
| $V_H$ Domain Mu. 1D9 | SEQ ID NO: 28 |
| $V_H$ Domain Hu$V_H$III | SEQ ID NO: 26 |

Figures 11A, 11B:
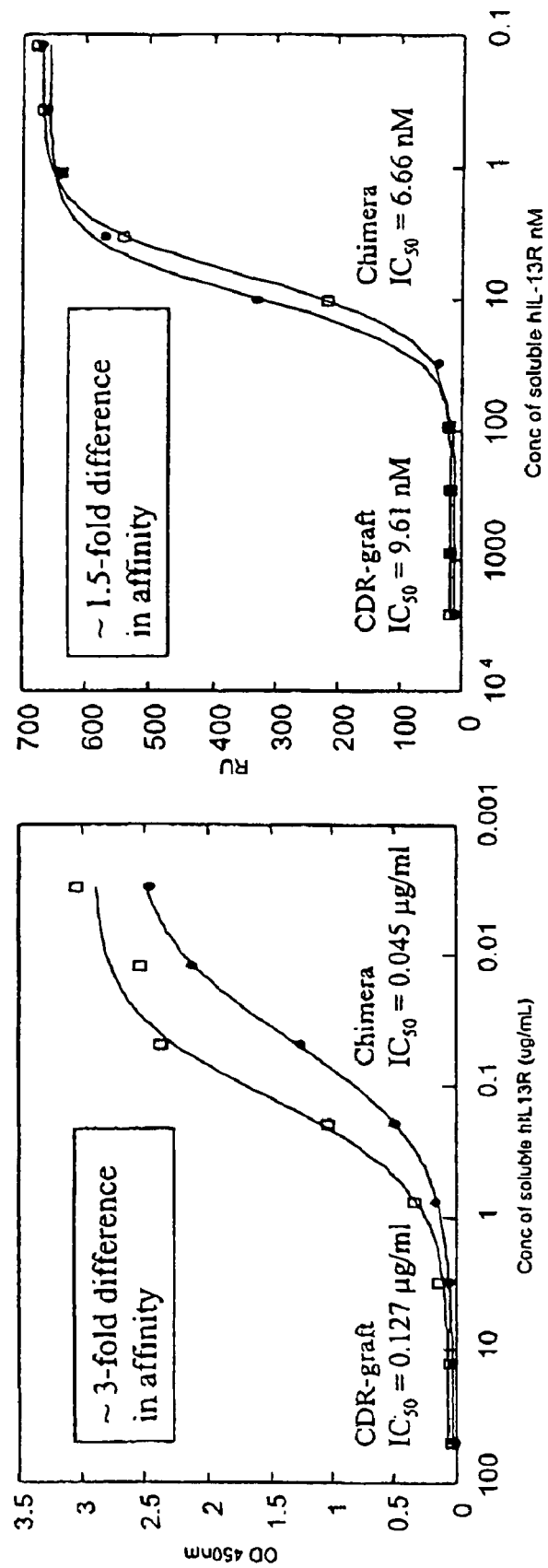

FIGS. 11A and 11B are graphical representations of binding affinities of the chimeric and CDR-grafted Fab fragment. (A) Competition ELISA of chimeric or CDR-grafted 1D9 phage displayed Fabs binding to plate bound hIL-13Rα1-Fc (ECD) (2.5 µg/ml) competed by soluble hIL-13Rα1 (ECD). (B) Biosensor competition assay of soluble 1D9 chimeric or CDR-grafted Fab binding to immobilized hIL-13Rα1 (ECD) competed by soluble hIL-13Rα1 (ECD). Fold-difference in affinity is calculated from ($IC_{50}/IC_{50}$).

DETAILED DESCRIPTION OF THE INVENTION

The present invention relates generally to antibodies that bind, interact or otherwise associated to or with the IL-13Rα1 chain or a fragment, portion or part thereof and antagonize IL-13 receptor-mediated signaling by IL-13 and/or IL-4 and which may be employed in the methods of the present invention. The antibodies preferably are monoclonal antibodies or antigen-binding fragments thereof. Preferably, the antibodies are in isolated, homogenous or fully or partially purified form.

Most preferably, the antibodies are humanized or human antibodies suitable for administration to humans. These include humanized antibodies prepared, for example, from murine monoclonal antibodies, and human monoclonal antibodies which may be prepared, for example, using transgenic mice as described below, or by phage display.

Reference to "binding" of an antibody means binding, interacting or associating with or to a target antigen such as IL-13Rα1. Reference to "IL-13Rα1" includes it fragments or portions which comprise the epitopes to which an antibody binds. Consequently, reference to an antibody binding to IL-13Rα1 includes the binding, interaction or association of the antibody or an antigen-binding portion thereof, part, fragment or epitope-containing region thereof.

Generally, "binding", "interaction" or "association" means or includes the specific binding, interaction or association of the antibody to an IL-13Rα1 or a portion thereof.

The biological effects of IL-13 are mediated by a dimeric receptor complex comprise the subunits IL-13Rα1 (or the NR4 subunit) and IL-4Rα (referred to hereinafter as the IL-13 receptor). Thus, some antibodies raised against IL-13Rα1 which block IL-13 binding and/or signaling through the IL-13 receptor complex, may also block the signaling of IL-4 through the IL-13 receptor complex.

Examples of antibodies contemplated by the present invention include those that bind to IL-13Rα1 and block the signaling of IL-13 through the IL-13 receptor complex, and preferably those that bind to IL-13Rα1 and block the signaling of IL-13 and/or IL-4 through the IL-13 receptor complex, thereby inhibiting an IL-13 induced and/or an IL-4 induced biological activity. Such antibodies, referred to herein as blocking antibodies, may be raised with an IL-13Rα1 polypeptide or immunogenic parts thereof, such as for example, the extracellular domain of IL-13Rα1 and screened in assays for the ability to block the signaling of IL-13 and/or IL-4 through the IL-13 receptor complex. Suitable assays are assays that test the antibodies for the ability to inhibit binding of IL-13 to cells expressing the IL-13 receptor complex, or that test antibodies for the ability to reduce a biological or cellular response that results from the signaling of IL-13 and IL-4 through the IL-13 receptor complex.

In one embodiment, the present invention provides antibodies that bind to IL-13Rα1 and inhibit IL-13 signaling through the IL-13 receptor complex.

In a further embodiment, the present invention provides antibodies that bind to IL-13Rα1 and inhibit IL-13- and IL-4-signaling through the IL-13 receptor complex.

Preferably the antibodies are monoclonal antibodies or antigen-binding fragments thereof.

Most preferably, the antibodies are human or humanized monoclonal antibodies suitable for use in human therapeutics.

As such, in a preferred embodiment, the present invention provides antibodies that are human or humanized monoclonal antibodies that bind to IL-13Rα1 and inhibit IL-13 signaling through the IL-13 receptor complex.

In an especially preferred embodiment, the present invention provides antibodies that are human or humanized monoclonal antibodies that bind to IL-13Rα1 and inhibit IL-13- and IL-4-signaling through the IL-13 receptor complex.

Reference to an "antibody" or "antibodies" includes reference to all the various forms of antibodies, including but not limited to whole antibodies, antibody fragments, including, for example, Fv, Fab, Fab' and F(ab')$_2$ fragments, humanized antibodies, human antibodies (e.g., produced in transgenic animals or through phage display) and immunoglobulin-derived polypeptides produced through genetic engineering techniques.

Unless stated otherwise, specificity in respect of an antibody of the present invention is intended to mean that the antibody does not exhibit any meaningful cross-reactivity with non-IL-13Rα1 proteins. However, it is not intended to indicate that there is no cross-reactivity with other forms of the IL-13Rα1 which may exist, (for example, soluble forms, splice variants or fragments of the receptor), nor is it intended to indicate that no cross-reactivity with IL-13Rα1 from other species may exist. The amino acid sequence of IL-13Rα1 is a well conserved across species, with other mammalian forms of the receptor showing substantial amino acid homology with the human IL-13Rα1 chain.

The antibodies may be specific for an IL-13Rα1 chain from a particular species, such as human IL-13Rα1, or, because of the level sequence similarity between IL-13Rα1 chains from certain mammalian species, may show some cross-reactivity with IL-13Rα1 chains from other mammalian species. In the case of antibodies directed towards human IL-13Rα1, some level of cross reactivity with other mammalian forms of IL-13Rα1 may be desirable in certain circumstances. For example, such antibodies are useful for the purpose of testing antibodies in animal models of a particular disease, and for conducting toxicology studies in a manner where IL-13 and/or IL-4 signaling in the test animal is affected by the test antibody. Species where cross reactivity of an antibody to human IL-13Rα1 may be desirable include monkey, sheep, dog and rat. Accordingly, one preferred group of antibodies are those which exhibit some level of species cross reactivity. A particularly preferred group of antibodies are those antibodies to human IL-13Rα1 which exhibit some level of species cross-reactivity.

The antibodies of the present invention bind to the IL-13Rα1 chain. The IL-13Rα1 chain may be the human IL-13Rα1 chain or from another animal, such as the murine IL-13Rα1 chain, the rat IL-13Rα1 chain, the canine IL-13Rα1 chain, the ovine IL-13Rα1 chain and the cynamologus monkey IL-13Rα1 chain. Preferably, the IL-13Rα1 chain is the human IL-13Rα1 chain. There is a high level of sequence homology between IL-13Rα1 chains from different species. For example, the ovine IL-13Rα1 chain is 87% homologous at the amino acid level and 88.7% homologous at the DNA level to human IL-13Rα1. Ovine IL-13Rα1 is 75% homologous at the amino acid level and 82.2% homologous at the DNA level to murine IL-13Rα1. Human IL-13Rα1 is 75% homologous at the amino acid level and 81.3% homologous at the DNA level to murine IL-13Rα1.

In a preferred embodiment, the present invention provides antibodies that bind to human IL-13Rα1 and to cynamolgus monkey IL-13Rα1 and inhibit IL-13 signaling through the IL-13 receptor complex.

In a further preferred embodiment, the present invention provides antibodies that bind to human IL-13Rα1 and to ovine IL-13Rα1 and which inhibit IL-13 signaling through the IL-13 receptor complex.

In still a further preferred embodiment, the present invention provides antibodies that bind to human IL-13Rα1 and to canine IL-13Rα1 and which inhibit IL-13 signaling through the IL-13 receptor complex.

In yet a further preferred embodiment, the present invention provides antibodies that bind to human IL-13Rα1 and to rat IL-13Rα1 and which inhibit IL-13 signaling through the IL-13 receptor complex.

In yet a further preferred embodiment, the present invention provides antibodies that bind to human IL-13Rα1 and to murine IL-13Rα1 and which inhibit IL-13 signaling through the IL-13 receptor complex.

The antibodies of the present invention may be prepared by well known procedures. See, for example, Monoclonal Antibodies, Hybridomas: A New Dimension in Biological Analyses, Kennet et al. (eds.), Plenum Press, New York (1980); and Antibodies: A Laboratory Manual, Harlow and Land (eds.), Cold Spring Harbor Laboratory Press, Cold Spring Harbor, N.Y., (1988).

One method for producing an antibody of the present invention comprises immunizing a non-human animal, such as a mouse or a transgenic mouse, with an IL-13Rα1 polypeptide, or immunogenic parts thereof, such as, for example, the extracellular domain of IL-13Rα1, whereby antibodies directed against the IL-13Rα1 polypeptide are generated in said animal.

Both polyclonal and monoclonal antibodies can be produced by this method. The methods for obtaining both types of sera are well known in the art. Polyclonal sera are less preferred but are relatively easily prepared by injection of a suitable laboratory animal with an effective amount of an IL-13Rα1 polypeptide, or immunogenic parts thereof, such as, for example, the extracellular domain of IL-13Rα1, collecting serum from the animal and isolating IL-13Rα1 specific sera by any of the known immunoadsorbent techniques. Antibodies produced by this technique are generally less favoured, because of the potential for heterogeneity of the product.

The use of monoclonal antibodies is particularly preferred because of the ability to produce them in large quantities and the homogeneity of the product. Monoclonal antibodies may be produced by conventional procedures.

The present invention contemplates a method for producing a hybridoma cell line comprises immunizing a non-human animal, such as a mouse or a transgenic mouse, with an IL-13Rα1 polypeptide, or immunogenic parts thereof, such as, for example, the extracellular domain of IL-13Rα1; harvesting spleen cells from the immunized animal; fusing the harvested spleen cells to a myeloma cell line to generate hybridoma cells; and identifying a hybridoma cell line that produces a monoclonal antibody that binds an IL-13Rα1 polypeptide.

Such hybridoma cell lines and the anti-IL-13Rα1 monoclonal antibodies produced by them are encompassed by the present invention. Monoclonal antibodies secreted by the hybridoma cell lines are purified by conventional techniques. Hybridomas or the monoclonal antibodies produced by them may be screened further to identify monoclonal antibodies with particularly desirable properties, such as the ability to inhibit IL-13- and IL-4-signaling through the IL-13 receptor complex.

The IL-13Rα1 polypeptide or immunogenic part thereof that may be used to immunize animals in the initial stages of the production of the antibodies of the present invention may be from any mammalian source. Preferably, the IL-13Rα1 polypeptide or immunogenic part thereof is human IL-13Rα1.

Antigen-binding fragments of antibodies of the present invention may be produced by conventional techniques. Examples of such fragments include, but are not limited to, Fab, Fab', F(ab') 2 and Fv fragments, including single chain Fv fragments (termed sFv or scFv). Antibody fragments and derivatives produced by genetic engineering techniques, such as disulphide stabilized Fv fragments (dsFv), single chain variable region domain (Abs) molecules and minibodies are also contemplated for use. Unless otherwise specified, the terms "antibody" and "monoclonal antibody" as used herein encompass both whole antibodies and antigen-binding fragments thereof.

Such derivatives of monoclonal antibodies directed against IL-13Rα1 may be prepared and screened for desired properties, by known techniques, including the assays described herein. The assays described herein provide the means to identify derivatives of the antibodies of the present invention that bind to IL-13Rα1, as well as identify those derivatives that also retain the activity of inhibiting signaling by IL-13 through the IL-13 receptor complex, and preferably, inhibiting signaling by IL-13 and IL-4 through the IL-13 receptor complex. Certain of the techniques involve isolating DNA encoding a polypeptide chain (or a portion thereof) of a mAb of interest, and manipulating the DNA through recombinant DNA technology. The DNA may be fused to another DNA of interest, or altered (e.g. by mutagenesis or other conventional techniques) to add, delete, or substitute one or more amino acid residues, for example.

DNA encoding antibody polypeptides (e.g. heavy or light chain, variable region only or full length) may be isolated from B-cells of mice that have been immunized with IL-13Rα1. The DNA may be isolated by conventional procedures such as polymerase chain reaction (PCR). Phage display is another example of a known technique whereby derivatives of antibodies may be prepared. In one approach, polypeptides that are components of an antibody of interest are expressed in any suitable recombinant expression system, and the expressed polypeptides are allowed to assemble to form antibody molecules.

Single chain antibodies may be formed by linking heavy and light chain variable region (Fv region) fragments via an amino acid bridge (short peptide linker), resulting in a single polypeptide chain. Such single-chain Fvs (scFvs) have been prepared by fusing DNA encoding a peptide linker between DNAs encoding the two variable region polypeptides (VL and VH). The resulting antibody fragments can form dimers or trimers, depending on the length of a flexible linker between the two variable domains (Kortt et al., *Protein Engineering* 10: 423, 1997). Techniques developed for the production of single chain antibodies include those described in U.S. Pat. No. 4,946,778; Bird (*Science* 242: 423, 1988), Huston et al. (*Proc. Natl. Acad. Sci. USA* 85: 5879, 1988) and Ward et al. (*Nature* 334: 544, 1989). Single chain antibodies derived from antibodies provided herein are encompassed by the present invention.

In one embodiment, the present provides derivatives of the antibodies of the present invention that bind to IL-13Rα1, and inhibit signaling by IL-13 through the IL-13 receptor complex. Preferably, the derivatives block signaling by Il-13 and IL-4 through the Il-13 receptor complex.

Techniques are known for deriving an antibody of a different subclass or isotype from an antibody of interest, i.e., subclass switching. Thus, IgG1 or IgG4 monoclonal antibodies may be derived from an IgM monoclonal antibody, for example, and vice versa. Such techniques allow the preparation of new antibodies that possess the antigen-binding properties of a given antibody (the parent antibody), but also exhibit biological properties associated with an antibody isotype or subclass different from that of the parent antibody. Recombinant DNA techniques may be employed. Cloned DNA encoding particular antibody polypeptides may be employed in such procedures, e.g. DNA encoding the constant region of an antibody of the desired isotype.

The monoclonal production process described above may be used in animals, for example mice, to produce monoclonal antibodies. Conventional antibodies derived from such animals, for example murine antibodies, are known to be generally unsuitable for administration to humans as they may cause an immune response. Therefore, such antibodies may need to be subjected to a humanization process in order to provide antibodies suitable for administration to humans. Such humanization processes are well known in the art and are described in further detail below.

Additional embodiments include chimeric antibodies and humanized versions of murine monoclonal antibodies. Such chimeric or humanized antibodies may be prepared by known techniques, for example, CDR grafting, and offer the advantage of reduced immunogenicity when the antibodies are administered to humans. In one embodiment, a chimeric monoclonal antibody comprises the variable region of a murine antibody (or just the antigen binding site thereof) and a constant region derived from a human antibody. Alternatively, a humanized antibody fragment may comprise the antigen binding sites (complementarity determining regions CDRs) of a murine monoclonal antibody and a variable region fragment (lacking the antigen-binding site) derived from a human antibody. Procedures for the production of chimeric and humanized monoclonal antibodies include those described in Riechmann et al. (*Nature* 332: 323, 1988) Liu et al. (*Proc. Natl. Acad. Sci. USA* 84: 3439, 1987), Larrick et al. (*Bio/Technology* 7: 934, 1989) and Winter and Harris (*TIPS* 14: 139, 1993).

The complementarity determining regions (CDRs) of a given antibody may be identified using the system described by Kabat et al. in Sequences of Proteins of Immunological Interest, 5th Ed., US Dept. of Health and Human Services, PHS, NIH, NIH Publication No. 91-3242, 1991).

For example, the murine monoclonal antibody 1D9 has been subjected to humanization to reduce the immunogenicity of the antibody in a target host, as described in the Examples below. Murine monoclonal antibody 1D9 has a specific and potent antagonistic effect against IL-13Rα1 and inhibits signaling through the IL-13 receptor and IL-4 signaling through the IL-13 receptor. However, the potential immunogenicity of mAb 1D9 in other hosts, and in particular humans, makes the use of mAb 1D9 unsuitable as a therapeutic agent in these hosts.

In a particular embodiment, the antibodies of the present invention comprise within the variable region of their light chain, at least one of the CDRs found in the light chain of mAb 1D9. The CDRs of mAb 1D9 are disclosed in FIG. 10 and in SEQ ID NOs: 9-24. Thus, among the antibodies contemplated by the present invention are those that comprise from one to all three of the CDR sequences from the light chain variable region of mAb 1D9. Further, among the antibodies contemplated by the present invention are those that comprise from one to all three of the CDR sequences from the heavy chain variable region of mAb 1D9. In a preferred embodiment, the antibodies of the present invention comprise from one to all six CDR sequences from the heavy and light chain variable regions of mAb 1D9.

Procedures for generating human antibodies in non-human animals have also been developed and are well known to those skilled in the art. The antibodies may be partially human, or preferably completely human. For example, transgenic mice into which genetic material encoding one or more human immunoglobulin chains has been introduced may be used to produce the antibodies of the present invention. Such mice may be genetically altered in a variety of ways. The genetic manipulation may result in human immunoglobulin polypeptide chains replacing endogenous immunoglobulin chains in at least some (preferably virtually all) antibodies produced by the animal upon immunization.

Mice in which one or more endogenous immunoglobulin genes have been inactivated by various means have been prepared. Human immunoglobulin genes have been introduced into the mice to replace the inactivated mouse genes. Antibodies produced in the animals incorporate 22 human immunoglobulin polypeptide chains encoded by the human genetic material introduced into the animal. Examples of techniques for production and use of such transgenic animals are described in U.S. Pat. Nos. 5,814,318, 5,569,825, and 5,545,806, which are incorporated by reference herein.

As such, antibodies of the present invention may include, but are not limited to, partially human (preferably fully human) monoclonal antibodies that inhibit signaling by IL-13, and preferably, inhibit signaling by IL-13 and IL-4 through the IL-13 receptor complex.

Another method for generating human antibodies is phage display. Phage display techniques for generating human antibodies are well known to those skilled in the art, and include the methods used by companies such as Cambridge Antibody Technology and MorphoSys and which are described in International Patent Publication Nos. WO 92/01047, WO 92/20791, WO 93/06213 and WO 93/11236.

Antibodies of the present invention may be employed in vitro or in vivo. Among the uses for antibodies of the present invention are assays (either in vitro or in vivo) to detect the presence of IL-13Rα1 polypeptides and immunoaffinity chromatography to purify IL-13Rα1 polypeptides. Further, those antibodies of the present invention that can inhibit signaling by IL-13 through the IL-13 receptor, as well as those antibodies that can inhibit signaling by IL-13 and IL-4 through the IL-13 receptor, may be used to inhibit a biological activity that results from such signaling.

Therefore, in one embodiment, such antibodies may be used in therapeutic applications to treat disorders caused or exacerbated (directly or indirectly) by the signaling of IL-13 or IL-4 through the IL-13 receptor complex. A therapeutic application involves in vivo administration of a blocking antibody to a mammal in an amount effective to inhibit signaling by IL-13 and/or IL-4 through the IL-13 receptor. Preferably, the antibodies are human or humanized monoclonal antibodies of the present invention.

The antibodies may be used to treat diseases or conditions induced by either or both IL-13 and IL-4 including but not limited to fibrosis, Hodgkin's disease, ulcerative colitis, scleroderma, lung disorders such as asthma and chronic obstructive pulmonary disease, allergic rhinitis, oncological conditions, inflammatory bowel disease and other inflammatory conditions in the gastrointestinal tract and allergic reactions to medication.

An antibody in accordance with the present invention is the murine monoclonal antibody 1D9, and humanized forms of mAb 1D9.

The amino acid sequence of the variable region of the light chain of mAb 1D9 is presented in SEQ ID NO: 27. The amino acid sequence for the variable region of the heavy chain of mAb 1D9 is presented as SEQ ID NO:28 Amino acid sequence of murine 1D9 CDR regions from $V_L$ domain grafted onto a human consensus framework is presented in SEQ ID NO: 25 Amino acid sequence of murine 1D9 CDR regions from $V_H$ domain grafted onto human consensus framework is presented as SEQ ID NO: 26.

Antibodies of the present invention include, but are not limited to, monoclonal antibodies that comprise, in their light chain, residues 1 to 112 of SEQ ID NO:25; and antibodies that additionally or alternatively comprise, in their heavy chain, residues 1 to 121 of SEQ ID NO:26, or monoclonal antibodies that comprise, in their light chain, residues 1 to 112 of SEQ ID NO:27; and antibodies that additionally or alternatively comprise, in their heavy chain, residues 1 to 121 of SEQ ID NO:28.

Particular monoclonal antibodies of the invention are selected from the group consisting of mAb 1D9; a mAb that is cross-reactive with mAb 1D9; a mAb that binds to the same epitope as mAb 1D9; a mAb that competes with mAb 1D9 for binding to a cell that expresses human IL-13Rα1; a mAb that possesses a biological activity of mAb 1D9; and an antigen-binding fragment of any of the foregoing antibodies. Antibodies in accordance with this embodiment include 6A9 and 3F10 as discussed in the Examples.

In one embodiment, the antibody has a binding affinity for human IL-13Rα1 that is substantially equivalent to the binding affinity of mAb 1D9 for human IL-13Rα1. mAb 1D9 is an IgG1 antibody. mAb of other isotypes (including but not limited to IgG4), derived from mAb 1D9 are also encompassed by the present invention. Hybridoma cell lines that produce any such monoclonal antibodies also are provided by the present invention.

Procedures for switching (altering) the subclass or isotype of an antibody are also well known to those skilled in the art. Such procedures may involve, for example, recombinant DNA technology, whereby DNA encoding antibody polypeptide chains that confer the desired subclass is substituted for DNA encoding the corresponding polypeptide chain of the parent antibody. This procedure is useful, for example, in certain antibody therapeutic applications where are particular antibody isotype is preferred, such as in the treatment of asthma where IgG4 may be the preferred antibody isotype.

One example of a biological activity of mAb 1D9 is the ability to bind to IL-13Rα1 and inhibit signaling by IL-13 and IL-4 through the IL-13 receptor complex. In one embodiment, a mAb of the invention possesses IL-13 biological activity blocking activity substantially equivalent to that of mAb 1D9; and possesses IL-4 biological activity blocking activity substantially equivalent to that of mAb 1D9. Such activity may be measured in any suitable conventional assay (e.g. as measured in the CD23 expression assay described below).

Particular embodiments of the invention are directed to novel polypeptides. DNA and amino acid sequence information has been determined for polypeptides that are components of certain antibodies of the present invention, as discussed in Examples 7, 8, and 9 below. Among the polypeptides of the present invention is a purified polypeptide comprising an amino acid sequence selected from the group consisting of the amino acid sequence presented in SEQ ID NO:25, SEQ ID NO:26, SEQ ID NO:27 and SEQ ID NO:28. For in vivo use, the polypeptides advantageously are purified. A polypeptide may be purified individually, or in the form of a purified antibody of which the polypeptide is a component.

The ability of the antibodies of the present invention to interfere with signaling by IL-13 and/or IL-4 through the IL-13 receptor complex can be confirmed in a number of assays.

One assay that may be used is described in International Patent Publication No. WO 01/92340, which is incorporated herein by reference. This assay is based on ability of both IL-13 and IL-4 to enhance the expression of the activation-associated surface antigen CD23 on human B cells. The antibodies of the present invention are tested for the ability to inhibit CD23 expression induced by IL-13 and by IL-4.

In brief, antibodies raised against human IL-13Rα1 can be tested either in the form of hybridoma supernatants or purified protein. Prior to addition to cultures, the antibodies are buffer exchanged against culture medium (RPMI 1640 plus 10% v/v heat-inactivated fetal bovine serum) by centrifugation, using Centricon filter devices (Amicon) with a 10 kDa cutoff.

Human peripheral blood B cells are purified as described (Morris et al., *J. Biol. Chem.* 274: 418-423, 1999). The B cells ($3\times10^5$/well) in culture medium are placed in 96-well round-bottomed microtiter plates and preincubated at room temperature for 30 min with test antibodies. Recombinant human IL-13 or IL-4 is then added to the cultures, and the cells cultured for 20-24 hours at 37° C. in a humidified atmosphere of 5% $CO_2$. At the end of the culture period, the cells are washed once in PBS+0.02% $NaN_3$ in the 96-well culture plate and resuspended in blocking buffer (2% normal rabbit serum+1% normal goat serum in PBS+$NaN_3$).

Phycoerythrin (PE)-conjugated CD23 monoclonal antibody (mAb) or PE-conjugated isotype control mAb (both from Pharmingen) are added to cells at a final dilution of 1:10. Cells are incubated for 30 minutes at 4° C., washed ×3 in PBS+$NaN_3$ and analyzed on a FacScan (Becton Dickinson) for CD23 expression.

Negative controls such as cells cultured with hybridoma growth medium or isotype-matched non-blocking human anti-hIL-13 receptor antibody are included. An anti-huIL-4R murine mAb (R&D Systems), previously shown to block the binding and function of both hIL-4 and hIL-13, can be used as a positive control for neutralization of CD23 induction by IL-4 and IL-13.

An alternative assay for identifying antibodies that function as IL-13Rα1 antagonists and block signaling by either IL-13 and/or IL-4 is described below and in the Examples.

In this assay, 293A12-cells are engineered to express chimeric polypeptides comprising the extracellular domain of either IL-13Rα1 or IL-4Rα operably connected to the transmembrane and cytoplasmic domains of the protein, gp130. When the engineered 293A12-cells are in the presence of IL-13 or IL-4, the chimeric polypeptides form a heterodimeric receptor complex which permits signal transduction to occur. The IL-13- or IL-4-mediated signal transduction is observable via an identifiable signal, such as the activation of a gene encoding a reporter molecule (Example 5).

Anti-IL-13Rα1 antibodies that antagonize IL-13 or IL-4 signaling through the IL-13 receptor will inhibit IL-13- and IL-4-mediated activation of the reporter molecule.

The level of signal transduction is conveniently determined by selecting cells wherein signal transduction activates a pathway regulating the expression of a gene encoding a reporter molecule that provides an identifiable signal. Preferred reporter molecules are enzymes such as luciferase.

293A12 cells are particularly preferred in this assay as they are 293T cells which stably express genetic material encoding a luciferase reporter molecule (Example 3). The expression of the luciferase reporter molecule is regulated by a STAT-3 signaling pathway which is activated by gp130 signaling.

The signal transduction portion from gp130 is particularly preferred, as it induces STAT-3 phosphorylation which leads to the expression of the STAT-3 activated luciferase reporter gene. However, the signal transduction portion from other molecules may also be employed. The choice of the signal transduction portion of the polypeptides must be matched to the activation or promoter portion of the gene encoding the reporter molecule.

Those skilled in the art appreciate that the cell based assays of the invention, for example described above and in Example 4, may be utilised as a basis for screening for modulators of IL-13Rα1/ligand interaction. While such methods are well known to those skilled in the art, a brief description of the method is provided herein. The method involves subjecting appropriately engineered cells to a signal producing amount of IL-13 or IL-4 under conditions where, in the absence of any antagonism of ligand receptor binding, a signal, for example luciferase expression, may be detected. The exposure is then conducted in the presence of test compounds and the level of signal detected compared with that detected in the absence of a test compound. Test compounds may include compound libraries, for example libraries of natural product extracts or libraries of synthetic compounds. Alternatively, phage display libraries of antibody variable domains and the like, or panels of monoclonal antibodies against IL-13Rα1 may be screened across the assay.

Chimeric polypeptides that may be used in the assay of the present invention are described in Examples 1 and 2 and comprise the amino acid sequences set forth in SEQ ID NO:8 and SEQ ID NO:10.

cDNA encoding the chimeric polypeptides contemplated for use in this assay comprise a nucleotide sequence selected from SEQ ID NO:7 and SEQ ID NO:9. The sequence defined by SEQ ID NO:7 comprises a sequence which encodes the IL-4Rα extracellular domain fused to the transmembrane and cytoplasmic domains of gp130. SEQ ID NO:9 comprises a sequence which encodes the IL-13Rα1 extracellular domain fused to the transmembrane and cytoplasmic domains of gp130.

Although 293A12 cells are described in the assay of the present invention, other cells may be used. Generally a eukaryotic cell is employed, and more particularly, a mammalian cell. The mammalian cells may be derived from humans, livestock animals, laboratory test animals and companion animals. Non-mammalian cells contemplated herein include cells from avian species, reptilian species, amphibian species and insect species. Preferably, the cell lacks endogenous γc.

The term "operably connected" is used in its broadest context to include molecules which have associated together such that they are in functional interaction with each other. Generally, the association is by a chemical linkage or bond. Preferably, the chemical linkage or bond is a peptide bond. The terms include, therefore, a polypeptide comprising a contiguous series of amino acids each linked via a peptide bond wherein one contiguous series of amino acids has ligand-binding properties and another contiguous series of amino acids has signal transduction properties.

Pharmaceutically acceptable carriers and/or diluents include any and all solvents, dispersion media, coatings, antibacterial and antifungal agents, agents used for adjusting tonicity, buffers, chelating agents, and absorption delaying agents and the like. The use of such media and agents for pharmaceutical active substances is well known in the art. Except insofar as any conventional media or agent is incompatible with the active ingredient, use thereof in the therapeutic compositions is contemplated. Supplementary active ingredients can also be incorporated into the compositions.

The pharmaceutical forms suitable for injectable use include sterile aqueous solutions (where water soluble) and sterile powders for the extemporaneous preparation of sterile injectable solutions. It must be stable under the conditions of manufacture and storage and must be preserved against the contaminating action of microorganisms such as bacteria and fungi. The carrier can be a solvent or dilution medium comprising, for example, water, ethanol, polyol (for example, glycerol, propylene glycol and liquid polyethylene glycol, and the like), suitable mixtures thereof and vegetable oils. The proper fluidity can be maintained, for example, by the use of superfactants. The preventions of the action of microorganisms can be brought about by various anti-bacterial and anti-fungal agents, for example, parabens, chlorobutanol, phenol, sorbic acid, thirmerosal and the like. In many cases, it will be preferable to include agents to adjust tonicity, for example, sugars or sodium chloride. Prolonged absorption of the injectable compositions can be brought about by the use in the compositions of agents delaying absorption, for example, aluminium monostearate and gelatin. The compositions may also include buffers and chelating agents.

Sterile injectable solutions are prepared by incorporating the active compounds in the required amount in the appropriate solvent with the active ingredient and optionally other active ingredients as required, followed by filtered sterilization or other appropriate means of sterilization. In the case of sterile powders for the preparation of sterile injectable solutions, suitable methods of preparation include vacuum drying and the freeze-drying technique which yield a powder of active ingredient plus any additionally desired ingredient.

The amount of active compound in such therapeutically useful compositions is such that a suitable dosage will be obtained.

The compositions of the present invention are useful in modifying an IL-13- or IL-4-mediated condition including but not limited to fibrosis, Hodgkin's disease, ulcerative colitis, scleroderma, lung disorders such as asthma and chronic obstructive pulmonary disease, allergic rhinitis, oncological conditions, inflammatory bowel disease and other inflammatory conditions in the gastrointestinal tract, allergic reactions to medication and any other IL-13 mediated diseases or conditions.

The human and humanized antibodies of the present invention and in particular humanized 1D9 are useful in the treatment of such conditions. Any adverse condition resulting from IL-13 and/or IL-4 interaction with IL-13Rα1 may be treated or prevented by the administration of the antibodies of the invention such as humanized 1D9.

Accordingly, another aspect of the present invention contemplates a method for the treatment or prophylaxis of a condition mediated by IL-13 and/or IL-4 such as but not limited to an inflammatory condition, said method comprising administering to a subject an effective amount of an antibody, such as humanized 1D9, for a time and under conditions sufficient to inhibit IL-13 and/or IL-4 signaling through the IL-13 receptor complex.

An "effective amount" in this context is an amount of an antibody sufficient to reduce IL-13 and/or IL-4 signaling through the IL-13 receptor complex by at least 40%, preferably at least 50%, more preferably by at least 60%, still more preferably by at least 70-80% or greater than 90%.

The method may also be measured at the level of amelioration of symptoms. Hence, an effective amount would be that amount required to at least partially alleviate symptoms of, for example, inflammation.

Preferably, the subject is a human. However, veterinary applications are also contemplated for livestock animals as well as companion animals. In such cases it would be necessary to prepare an appropriate antibody designed to avoid an immunogenic response to the antibody by the mammal.

In a specific embodiment, therefore, the present invention provides a method for ameliorating the effects of IL-13 or Il-4 mediated conditions in a human subject, said method comprising administering to said subject an effective amount of a humanized 1D9 monoclonal antibody or its equivalent for a time and under conditions sufficient to ameliorate the effects of inflammation.

The present invention further contemplates the use of a humanized 1D9 or its equivalent in the manufacture of a medicament in the treatment or prophylaxis of an inflammatory condition in a subject.

The humanized 1D9 may also be used to deliver specific drugs conjugated thereto to particular sites, such as cells carrying the IL-13Rα1 receptor. The humanized 1D9 antibodies may also be used to conduct imaging analysis to screen for active IL-13Rα1 receptors.

The present invention is further described by the following non-limiting Examples.

EXAMPLE 1

Construction of the IL13Rα1/gp130 Chimera

To generate the chimeric IL13Rα1/gp130 cDNA molecule, the IL13R was amplified with a 5' oligomer containing an Asc1 restriction enzyme site, for cloning into the pEFBOS vector, and a 3' oligomer that contained an overlapping region homologous to the gp130 cDNA. The oligomers used to amplify the gp130 cDNA comprised a 3' oligomer containing an Mlu1 restriction enzyme site.

IL-13R1 Oligomers

5' oligomer:
AGCTGGCGCGCCAGGCGCCTACGGAAACTCAGCCACCTGTG  [SEQ ID 11]

3' oligomer:
CAGGCACGACTATGGCTTCAATTTCTCCTGTGGAATTGCGCTTCTTACCTATACTC [SEQ ID NO: 12]

gp130 Oligomers

5' oligomer:
[SEQ ID NO: 13]
GGAGAAATTGAAGCCATAGTCGTGCCTGTTTGCTTAGC

3' oligomer:
[SEQ ID NO: 14]
ACGTACGCGTTCACTGAGGCATGTAGCCGCCTTGCCG

The PCR conditions to amplify the IL-13Rα1 and the gp130 regions required for the construction of the chimeric cDNA were identical for both molecules. One cycle of 94° C. for 2 mins, 35 cycles of 94° C. for 10 secs, 50° C. for 10 secs and 68° C. for 1 min and one cycle at 68° C. for 5 mins. The molecules were amplified using the PLATINUM Pfx DNA polymerase kit (Invitrogen).

The chimeric cDNA molecule was amplified using the PCR products generated from the previously described reactions, with the same conditions being used, except that the extension time was lengthened from 60 to 90 secs. The oligomers used to generate the chimeric cDNA molecule were:

5' oligomer:
[SEQ ID NO: 11]
AGCTGGCGCGCCAGGCGCCTACGGAAACTCAGCCACCTGTG

3' oligomer:
[SEQ ID NO: 14]
ACGTACGCGTTCACTGAGGCATGTAGCCGCCTTGCCG

The chimeric cDNA was the cloned into the Mlu1 restriction enzyme site of the pEFBOS mammalian expression vector, which contains the murine IL-3 signal sequence and a FLAG peptide at the N terminus. The cloning was carried out using the Amersham ligation kit.

EXAMPLE 2

Construction of the IL-4Rα/gp130 Chimera

The IL-4Rα was amplified by RT-PCR, from mRNA isolated from Jurkat cells, using the Titan RT-PCR kit (Roche). The oligomers use to amplify the IL-4Rα were:—

5' oligomer:
[SEQ ID NO: 15]
TGA AGG TCT TGC AAG AGC CCA CCT GCG

3' oligomer:
[SEQ ID NO: 16]
GTG CTG CTC GAA GGG CTCCCT GTA GGA G

The PCR conditions were as follows. One cycle of 50° C. for 30 mins and 94° C. for 2 mins, 35 cycles of 94° C. for 30 secs, 50° C. for 30 secs and 68° C. for 1 min and one cycle of 68° C. for 7 min.

To generate the chimeric IL-4Rα/gp130 cDNA molecule, the IL-4Rα was amplified with oligomers that comprised of a 5' oligomer that contained an Asc1 restriction enzyme site, for cloning into the pEFBOS vector and a 3' oligomer that contained an overlapping region homologous to the gp130 cDNA. The oligomers used to amplify the gp130 cDNA comprised a 3' oligomer containing an Mlu1 restriction enzyme site.

IL-4R Oligomers

5' oligomer:
AGCTGGCGCGCCTGAAGGTCTTGCAGGAGCCCACCTGCG  [SEQ ID NO: 17]

3' oligomer:
CAGGCACGACTATGGCTTCAATTTCTCCGTGCTGCTCGAAGGGCTCCCTGTAGGAG [SEQ ID NO: 18]

gp130 Oligomers

5' oligomer:
[SEQ ID NO: 13]
GGAGAAATTGAAGCCATAGTCGTGCCTGTTTGCTTAGC

3' oligomer:
[SEQ ID NO: 14]
ACGTACGCGTTCACTGAGGCATGTAGCCGCCTTGCCG

The PCR conditions to amplify the IL-4-a receptor and the gp 130 regions required for the construction of the chimeric cDNA were identical for both molecules. One cycle of 94° C. for 2 mins, 35 cycles of 94° C. for 10 secs, 50° C. for 10 secs and 68° C. for 1 min and one cycle at 68° C. for 5 mins The molecules were amplified using the PLATINUM Pfx DNA polymerase kit (Invitrogen).

The chimeric cDNA molecule was amplified using the PCR products generated from the previously described reactions, with the same conditions being used, except that the extension time was lengthened from 60 to 90 secs. The oligomers used to generate the chimeric cDNA molecule were:

```
5' oligomer:
                                        [SEQ ID NO: 17]
AGCTGGCGCGCCTGAAGGTCTTGCAGGAGCCCACCTGCG 3' oligomer:
                                        [SEQ ID NO: 14]
ACGTACGCGTTCACTGAGGCATGTAGCCGCCTTGCCG
```

The chimeric cDNA was cloned into the Mlu1 restriction enzyme site of the pEFBOS mammalian expression vector, which contains the murine IL-3 signal sequence and a FLAG peptide at the N terminus. The cloning was carried out using the Amersham ligation kit.

EXAMPLE 3

Generation of A12 Cells 293T cells (obtained from Amrad Biotech) were cotransfected with 10 μg APRE-luc (Nakajima et al., *EMBO J.* 15: 3651-3658, 1996) and 1 μg pGK-puro using lipofectamine (Life Technologies, Lot #KE4Y01).

Cells were selected in 25 μg/ml puromycin and positive clones tested for luciferase response.

Cell line A25-20 was subsequently further cloned by limit dilution, giving the clone 293T-A12.

EXAMPLE 4

Development of Assays for Analysis of IL-13Rα1 Interaction

Human factor-dependent (GM-CSF, IL-6, IL-4, or IL-13 etc.) TF-1 cells were previously used as the standard bioassay for IL-13 activity which is based on assessing the neutralizing/inhibitory activity of mouse and human mAbs. However, the assay has proven to be extremely unreliable with a relatively poor response to IL-13 and a low signal to background ratio.

Development of a Cell-Based Assay

Figure 1:
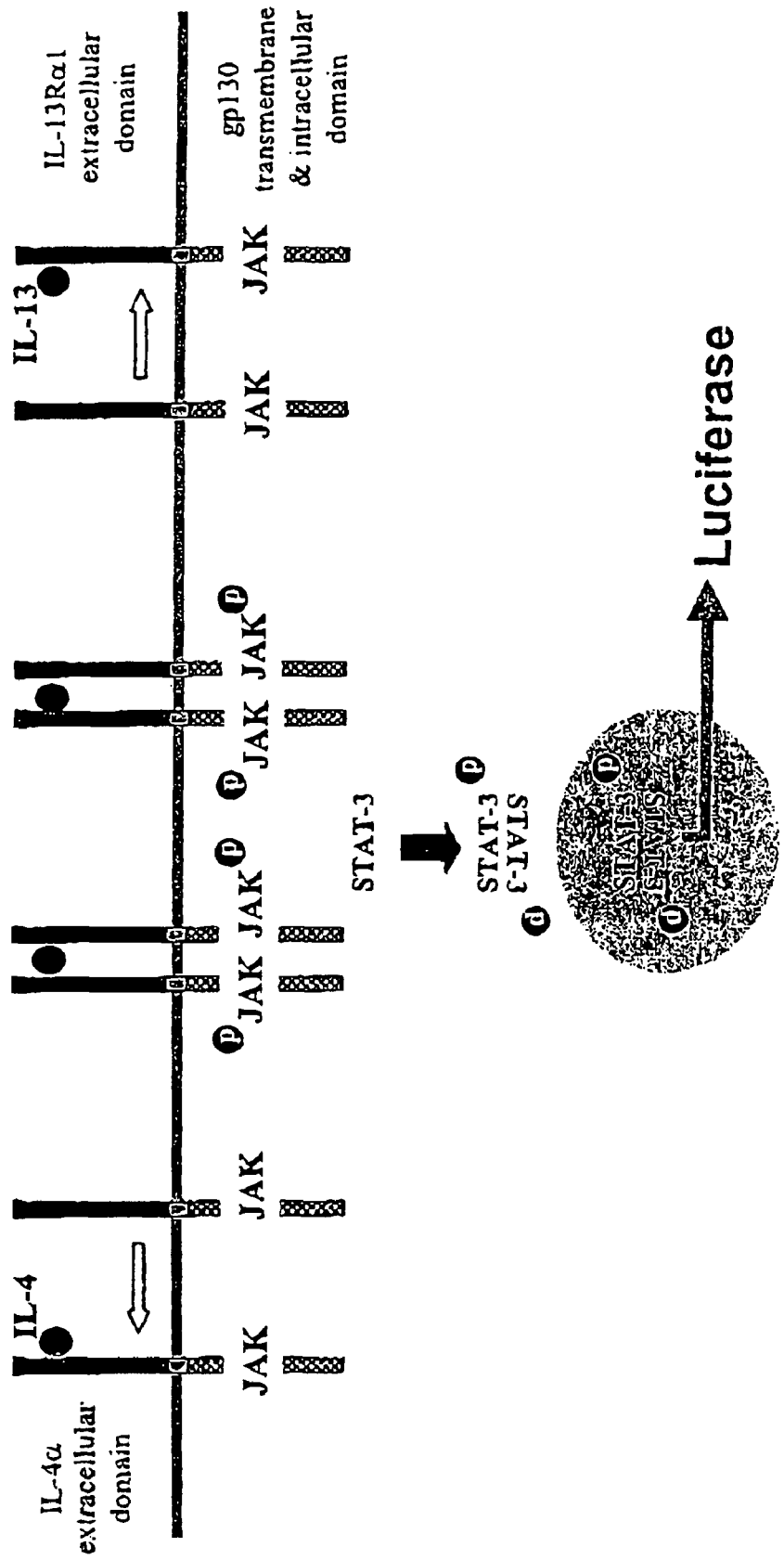
FIG. 1 is a diagrammatic representation showing that dimerization of chimeric receptors mediated by IL-13 or IL-4 induces STAT-3 phosphorylation through the gp130 intracellular domain and subsequently expression of the STAT-3 activated luciferase reporter gene.

The inventors developed an assay based on a chimeric receptor strategy. The strategy involves fusing the extracellular domain of both the IL-13Rα1 and the IL-4Rα to the transmembrane and cytoplasmic domains of gp130. Following production of these two chimeric receptors in the 293A12 cell line (a 293T derivative with stable expression of a luciferase reporter under the control of a STAT-3 responsive promoter), IL-13 mediated dimerization activates STAT-3 and subsequently luciferase reporter gene expression (FIG. 1).

An important aspect of this strategy is that it allows the identification of IL-13Rα1 antagonists such as mAbs that inhibit IL-4 signaling mediated through the IL-4 type II receptor complex. IL-4 signals through a type I receptor complex that incorporates the IL-4Rα and γc, and a type II receptor complex that incorporates the IL-4Rα and IL-13Rα1. Cell lines such as TF-1 are not suited to this purpose as they co-express γc and IL-13Rα1 such that IL-4 may signal through either of the two receptor complexes. In contrast, in the engineered cell line of the present invention, only IL-4 signaling through the type II complex should lead to luciferase expression, irrespective of 293T cell γc expression.

Using IL-13Rα1 and gp130 cDNAs as template, a human IL-13Rα1-gp130 chimeric receptor cDNA is generated by splice-overlap-extension PCR and cloned into pEFBOS for expression as an N-terminal FLAG-tagged protein. For generation of the IL-4Rα-gp130 chimeric receptor, an IL-4Rα cDNA (extracellular domain only) is cloned by RT-PCR using mRNA extracted from TF-1 cells. The chimeric IL-4Rα-gp130 receptor cDNA is generated by splice-overlap-extension PCR and also cloned into pEFBOS for expression as an N-terminal FLAG-tagged protein.

Figure 2:
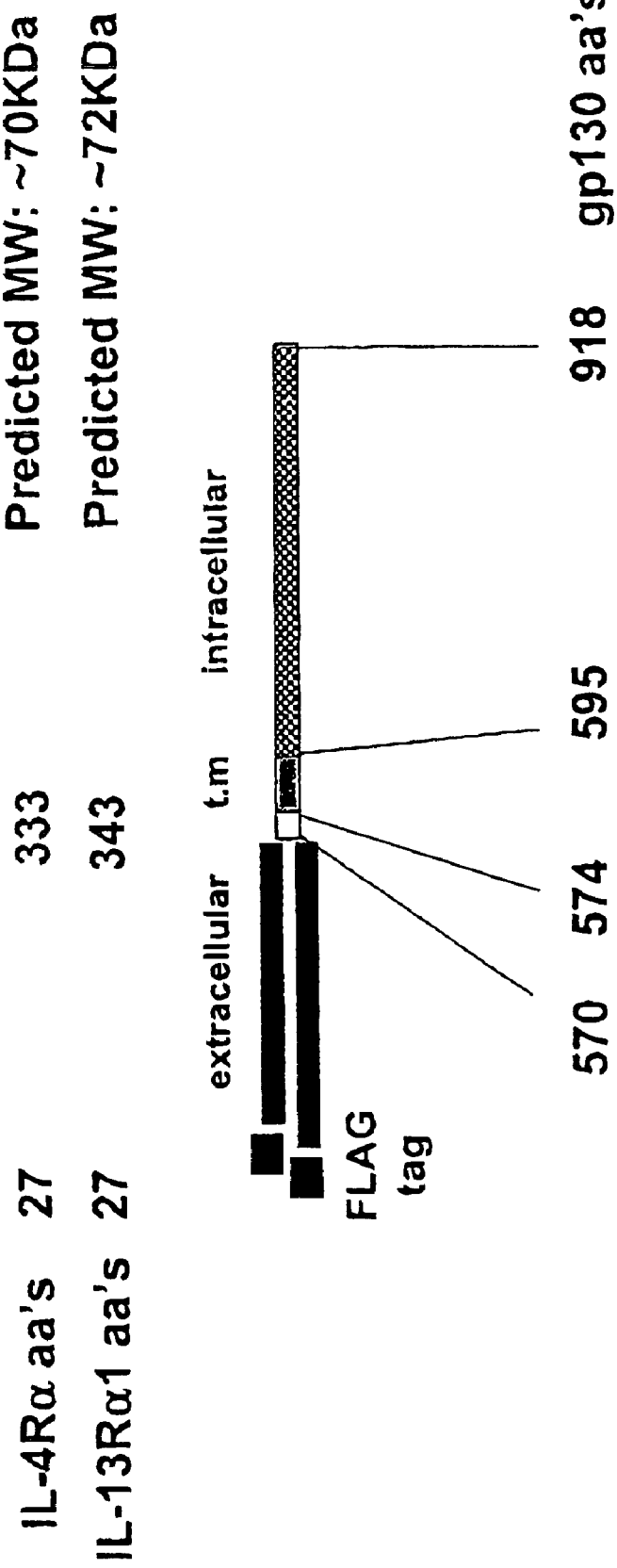
FIG. 2 is a diagrammatic representation showing construction of chimeric receptors incorporating the IL-13Rα1 or IL-4Rα extracellular domain and the transmembrane and intracellular domains of gp130; cloned into the pEFBOS vectors for expression as an N-terminal FLAG-tagged protein.
Figure 3:
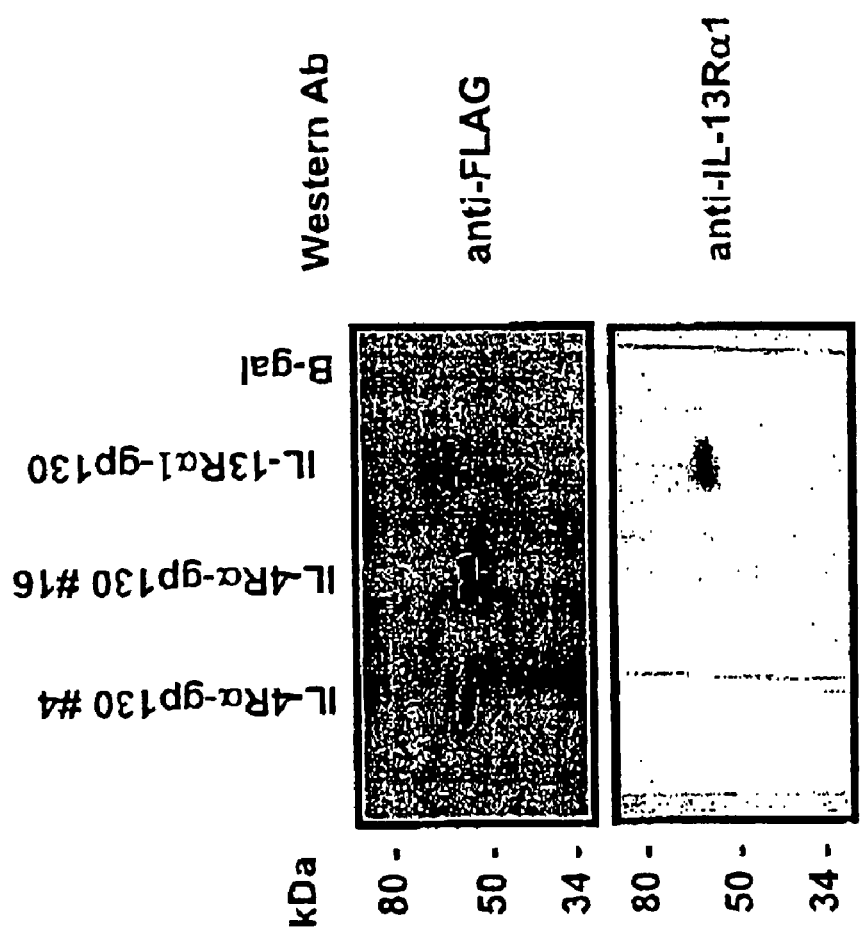
FIG. 3 is a photographic representation showing transient expression of chimeric receptor constructs in COS cells. COS cells were transfected with pEFBOS encoding FLAG-tagged IL-13Rα1-130, FLAG-tagged IL-4Rα-gp130 (two independent clones) or control β-gal. Cell lysates were recovered at 72 hrs and after SDS-PAGE and Western transfer, probed with either an anti-FLAG antibody or the IL-13Rα1-specific mAb 1D9.

Details of both chimeric receptors are provided in schematic form in FIG. 2. Transient expression in COS cells, followed by Western blot analysis with anti-FLAG or anti-IL-13Rα1 antibodies confirmed that both constructs encode a protein of the expected molecular weight (FIG. 3).

To isolate stable lines, 293A12 cells are co-transfected with the chimeric receptor constructs and a vector encoding the gene for hygromycin resistance. Following hygromycin selection, 100 isolated resistant colonies are picked and expanded through 48 and 24 well plates. Subsequently 56 of the picked colonies are assayed for luciferase in the presence of LIF (+ve control), IL-13 and IL-4. Thirteen of the 56 colonies assayed appear to express luciferase in response to both IL-13 and IL-4 in addition to LIF (Table 2) and of these 11 were expanded for freezing and further analysis.

Figures 4A, 4B:
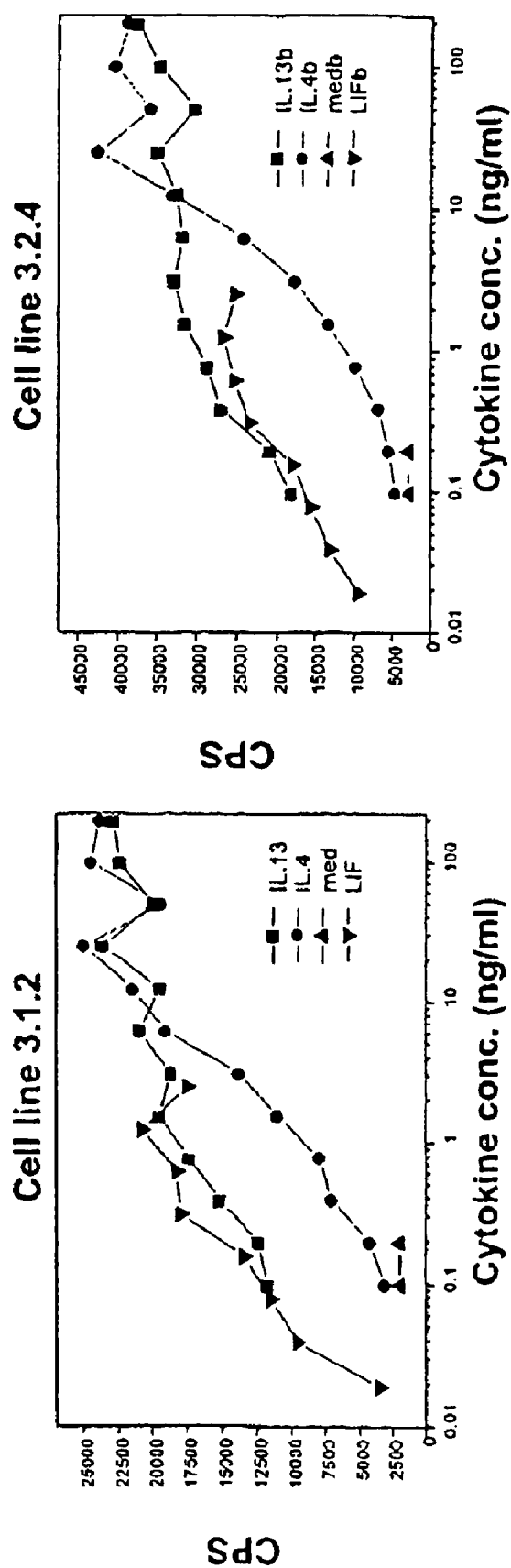
FIG. 4 is a graphical representation showing a dose-response analysis to LIF, IL-13 and IL-4 of chimeric receptor transfected 293A12 lines 3.1.2 and 3.2.4. 293A12 cells are derivatives of 293T cells that have been stably transfected with a STAT-3 luciferase reporter construct. After initial analysis, lines 3.1.2 (A) and 3.2.4 (B) were expanded and assayed against titrating LIF, IL-13 and IL-4. Both lines and an additional line, 3.2.5 were cloned by limiting dilution. Assay conditions were 5×10⁴ cells/well 24 hr incubation.

The two cell lines with the best signal to noise ratio (3.1.2 and 3.2.4) were subsequently cloned by limited dilution and for both, a full dose response analysis with respect to IL-4, IL-13 and LIF was conducted (FIG. 4). For both cell lines, the response to IL-13 appears similar to that observed for LIF with 50% of maximal activity observed at 100-200 pg/ml. For IL-4, 50% of maximal activity observed at 2-4 ng/ml for both lines. Consistent with earlier data, the signal to noise ratio for both lines is in excess of 10. The data indicate that these cell lines represent the best cell-based assays for either IL-13 or IL-4.

Molecular Assay

A molecular assay based on the interaction of IL-13Rα1 with IL-13 represents the best primary screen for both monoclonal antibodies and, potentially, small molecule antagonists. As stated above, however, the interaction of IL-13 with the IL-13Rα1 is weak (>200 nM) and not amenable to a simple ELISA-based approach. While FRET and fluorescence polarization-based assays have been contemplated, the development of such assays is labour and material intensive.

A chimeric receptor protein that incorporates the extracellular domain of the IL-13Rα1 (human or mouse) and the Fc portion of human IgG has been developed (R & D Systems). These chimeric proteins are expressed as preformed dimers, based on inter-Fc region disulphide bonds and are expected to associate more tightly with IL-13 than the monomeric form of the receptor.

For initial Biosensor studies, human IL-13 was immobilized to the Biosensor chip and a dose-response analysis of human and mouse IL-13Rα1-Fc binding was completed. Both chimeric receptors associated with human IL-13, with the signal obtained for the mouse receptor substantially higher than that obtained with the human receptor. Similar results are obtained with immobilized mouse IL-13. These findings confirm the cross-species activity of IL-13. To confirm the specificity of this interaction, a competitive binding-based approach is employed. A fixed concentration of chimeric mouse receptor protein was incubated with titrating soluble mouse IL-13 and binding of the receptor to immobilized mouse IL-13 was assessed. The soluble IL-13 was able to compete for binding to the chip in a dose-dependant manner. Similar data was obtained using the chimeric human receptor.

A qualitative comparison of sensorgrams obtained in this study to data obtained previously with monomeric receptor protein, indicated a substantial improvement in binding kinetics. This improvement is attributed to a much slower off-rate for the dimeric form, compared with the monomeric form, of the receptor. To further quantify this interaction a complete dose-response analysis using both human and mouse chimeric receptor proteins and immobilized human and mouse IL-13 was undertaken. Primary data obtained for the binding of the chimeric human and mouse receptors to mouse IL-13 are presented in Table 3. The chimeric mouse receptor appears to have an approximately 10-fold greater affinity for both human and mouse IL-13 compared with the chimeric human receptor. Nevertheless, the chimeric human receptor demonstrates a 100-fold increase in affinity for IL-13 compared with the monomeric form of the receptor.

Biosensor data indicate a substantial increase in binding affinity for the dimeric form of the receptor compared with the monomeric form and suggested that an ELISA-based approach to a molecular assay may be feasible. Preliminary experiments indicated that the interaction of soluble chimeric receptors with plate bound mouse IL-13 is readily detectable using an anti-huIg-HRPO conjugate. As expected, a higher concentration of the human receptor is required to obtain a signal equivalent to that obtained with the mouse receptor. Subsequently, both chimeric mouse and human receptors were titrated over various concentrations of plate bound IL-13 to establish optimal assay conditions. Results indicated that the chimeric human receptor titrates over a dose-range of 0.312-10 µg/ml with plate bound IL-13 at concentrations greater than 2.5 µg/ml. In comparison, the chimeric mouse receptor titrates over a dose-range of 0.02-0.625 µg/ml with plate bound IL-13 at greater than 1.25 µg/ml. As expected, control chimeric receptor, Flt-Fc, failed to bind in this assay.

EXAMPLE 5

Analysis of IL-13Rα1-Specific Mouse mAbs

Analysis Using Biochemical Assays—Biosensor and ELISA

Figure 5:
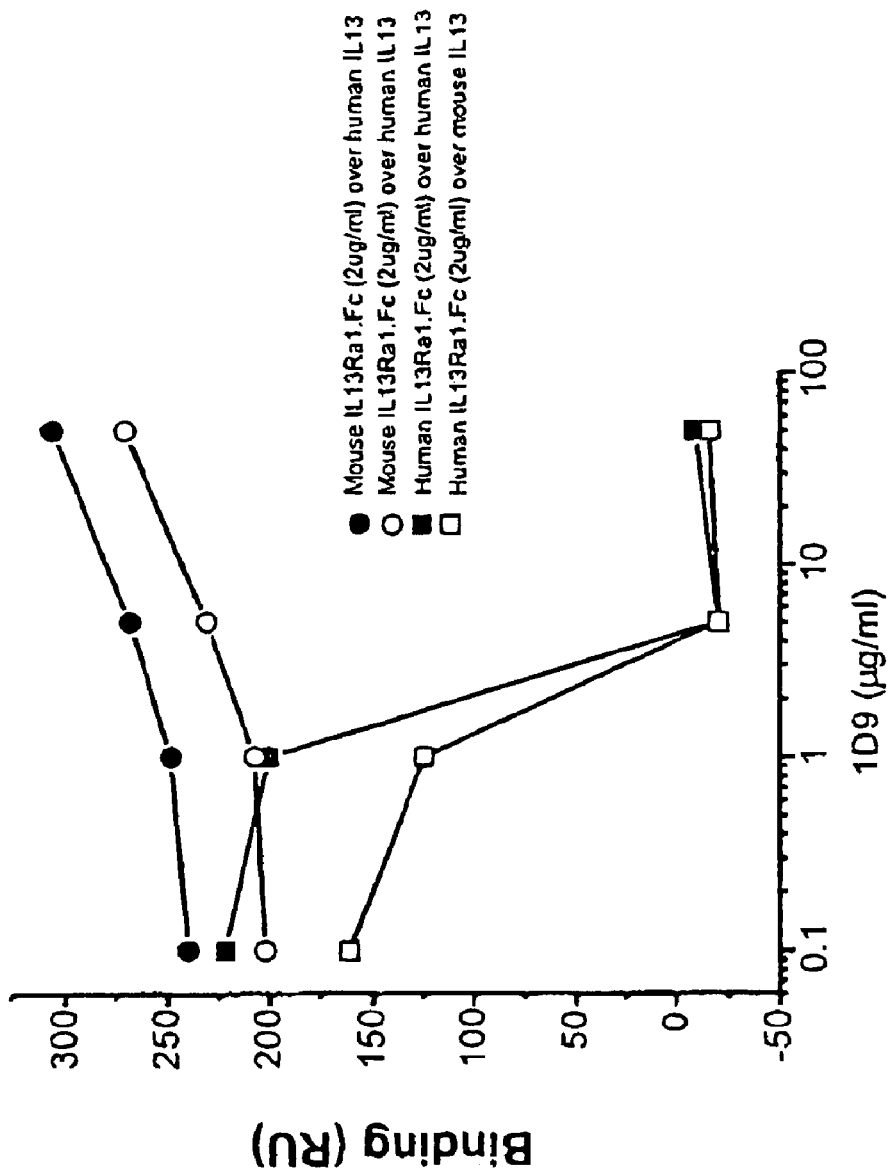
FIG. 5 is a graphical representation showing Biosensor analysis of mAb 1D9 inhibition of binding of chimeric human IL-13Rα1-Fc to human and mouse IL-13. mAb 1D9 and the chimeric receptors were pre-incubated at the indicated concentrations for 1 hour prior to analysis.
Figure 6B:
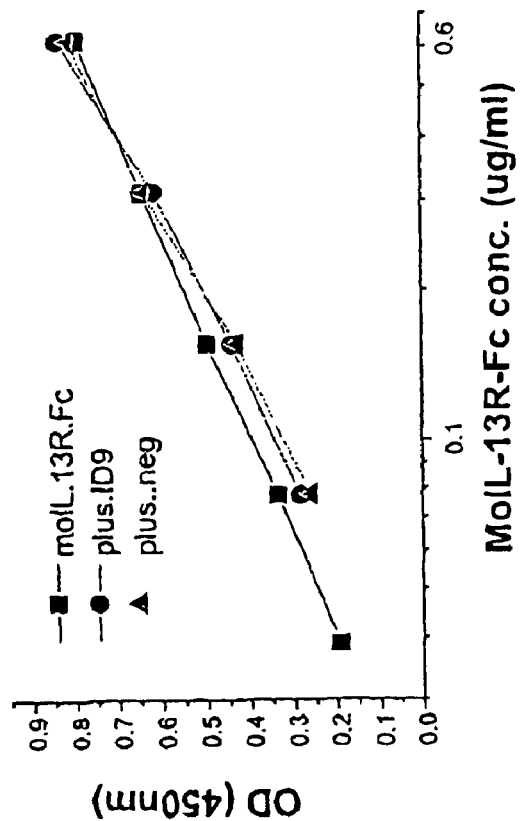
FIG. 6 is a graphical representation showing that mouse mAb 1D9 inhibits the binding of chimeric human (A) but not chimeric mouse (B) IL-13Rα1-Fc to plate bound mouse IL-13. Titrating chimeric receptor proteins were pre-incubated with mAbs (final concentration 50 µg/ml) for 45 min prior to transfer to assay plates coated with mouse IL-13. Anti-VEGF-B specific mAb 6C12 was used as a negative control.
Figure 6A:
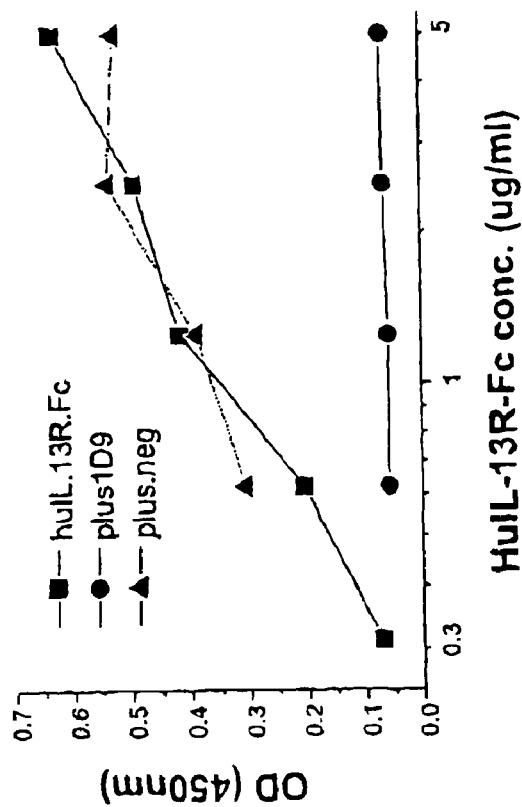

Initially mouse mAb 1D9 is tested for its ability to inhibit the interaction of the chimeric human and mouse IL-13Rα1-Fc with IL-13 using both an ELISA- and Biosensor-based approach. In Biosensor studies, 1D9 clearly inhibits the interaction of the chimeric human receptor with both human and mouse IL-13 but has no effect on the binding of the chimeric mouse receptor (FIG. 5). Identical results are obtained with the ELISA-based assay. 1D9 is a potent inhibitor of the chimeric human receptor, compared with a control mAb, but has no effect on the binding of the chimeric mouse receptor to mouse IL-13 (FIG. 6). The Biosensor study incorporated a 1D9 dose-response analysis and a further dose-response analysis was undertaken using the ELISA. These results demonstrated that 1D9 is a potent antagonist with an $IC_{50}$ similar to the concentration of target receptor used in the assays (~20 nM for the ELISA). The selectivity of 1D9 for human but not mouse IL-13Rα1 is also demonstrated using Western blot analysis.

Figure 7:
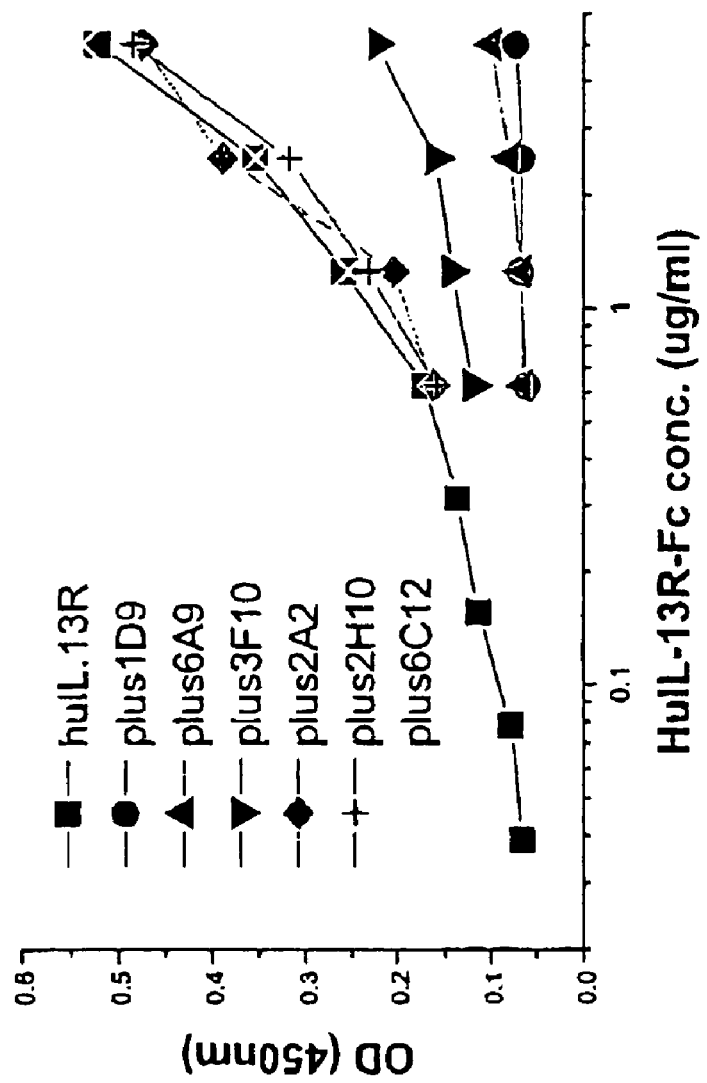
FIG. 7 is a graphical representation showing analysis of further IL-13Rα1 specific mouse mAbs for ability to inhibit binding of chimeric human IL-13Rα1 to plate bound mouse IL-13. Titrating chimeric human receptor was pre-incubated with IL-13Rα1 specific mAbs (1D9, 6A9, 3F10, 2A2) or negative control antibodies (2H10, 6C12) at a final concentration of 50 m/ml for 45 min prior to transfer to assay plates.

In further studies, additional mouse mAbs are tested by ELISA for their ability to inhibit the interaction of the chimeric human receptor with IL-13. mAb 6A9, which interacts with the same epitope as 1D9 shows potent antagonist activity (FIG. 7). mAb 3F10 binds to a different epitope and appeared to have a partial inhibitory activity. In contrast, mAb 2A2 which binds to a further unrelated epitope and which is most useful in Western blot analysis, fails to inhibit the chimeric receptor-ligand interaction. As expected unrelated control mAbs 2H10 and 6C12 had no effect on binding.

Analysis Using the Cell-Based Assay

The uncloned IL-13/IL-4-responsive transfected 293A12 derivative, 3.2.4, is expanded and used to assess the antagonist activity of the IL-13Rα1-specific mouse mAbs 1D9, 6A9 and 2A2. 3.2.4 cells are pre-incubated for 45 mins in titrating mAb prior to the addition of either IL-13 or IL-4 to a final concentration of 10 or 1 ng/ml. Luciferase production is assessed at 24 hrs.

Figure 8:
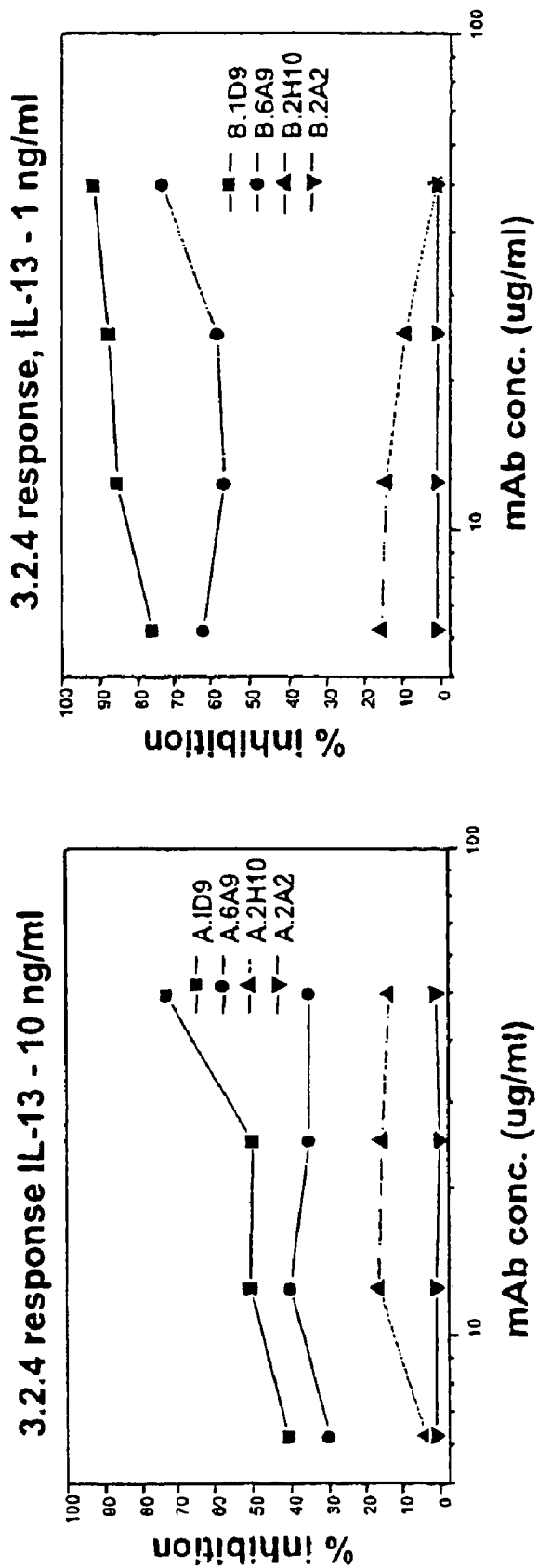
FIG. 8 is a graphical representation showing that mouse mAbs against the human IL-13Rα1 inhibit the 3.2.4 response to IL-13. 3.2.4-cells are cultured for 24 hrs in the presence of 10 or 1 ng/ml IL-13 and the indicated concentration of mAb. mAbs 1D9, 6A9 and 2A2 are IL-13Rα1 specific mAbs and 2H10 was an isotype matched negative control antibody. Percentage inhibition is calculated from (response to cytokine plus mAb/response to cytokine only)×100.

Results presented in FIG. 8 demonstrate that, in agreement with biochemical assay data, mAbs 1D9 and 6A9 (but not mAb 2A2) are able to inhibit IL-13 mediated luciferase expression. For both 6A9 and 1D9, the inhibitory activity was most pronounced with IL-13 at 1 ng/ml. 1D9 appeared to be more potent than 6A9 with almost complete inhibition of the response to 1 ng/ml of IL-13 over the dose-range of mAb tested. The negative control unrelated mAb 2H10 had no effect on IL-13-induced luciferase expression as expected.

Figure 9:
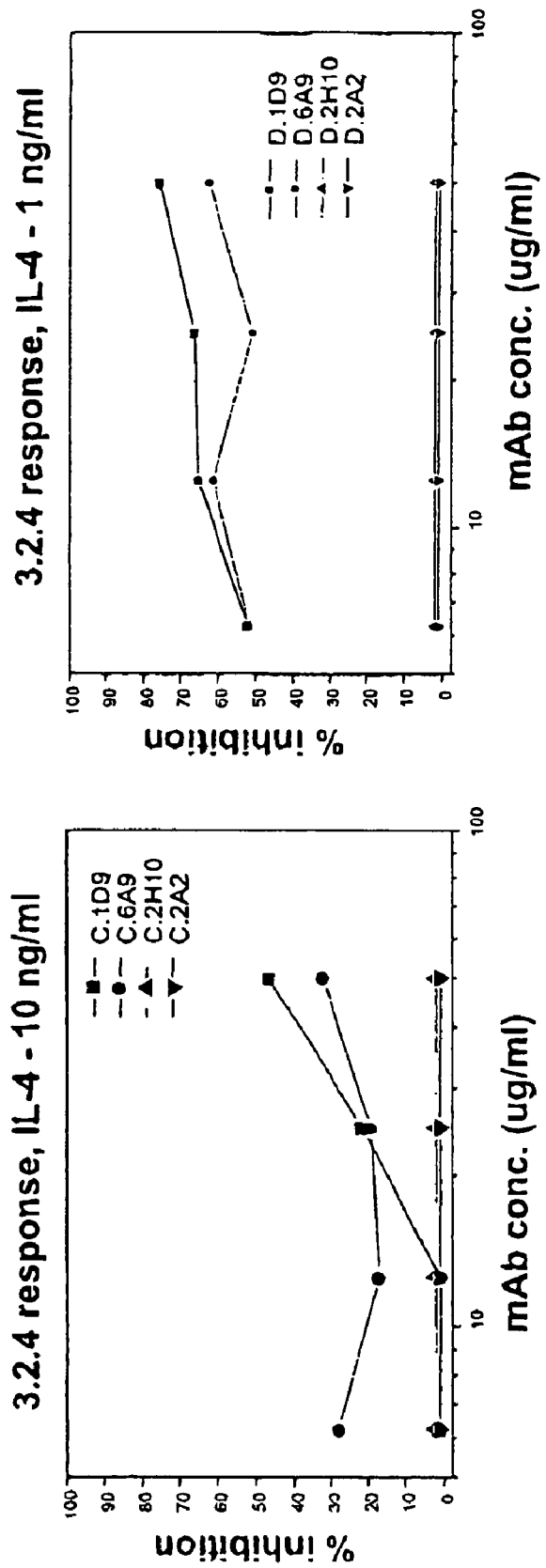
FIG. 9 is a graphical representation showing that mouse mAbs against the human IL-13Rα1 inhibit the 3.2.4 response to IL-4. 3.2.4-cells were cultured for 24 hrs in the presence of 10 or 1 ng/ml IL-4 and the indicated concentration of mAb. mAbs 1D9, 6A9 and 2A2 are IL-13Rα1 specific mAbs and 2H10 was an isotype matched negative control antibody. Percentage inhibition is calculated from (response to cytokine plus mAb/response to cytokine only)×100.

Unlike biochemical-based assays and existing cell-based assays, the 3.2.4 line allows the effects of IL-13Rα1 specific mAbs on IL-4 signaling through the type II IL-4 receptor complex to be assessed. Results presented in FIG. 9 demonstrate that both mAbs that are able to inhibit IL-13-mediated activity are also able to inhibit IL-4 mediated luciferase expression. Again, the effect was substantially more pronounced with cytokine at 1 ng/ml compared with 10 ng/ml and again 1D9 appeared to be the most potent of the two antibodies. As with IL-13, neither mAb 2A2 nor the negative control mAb 2H10, had any effect on IL-4-induced luciferase expression.

EXAMPLE 6

Cloning and Sequencing of the Murine Antibody Variable Regions

Messenger RNA was prepared from hybridoma cells producing the 1D9 mAb and reverse transcribed using an oligo-dT primer to produce cDNA. Partially degenerate PCR primers based on the amino-terminal amino acid sequence and the antibody isotype were used to amplify the mature mouse heavy and light variable domains and incorporate restriction enzyme sites for cloning. The subsequent clones and PCR products were sequenced to reveal the amino acid sequence for each of the variable regions of 1D9 (FIG. 1).

EXAMPLE 7

Construction of a Human Fab Template

A synthetic human fragment antibody binding (Fab) was generated from synthetic oligonucleotides as a template for intermediate and humanized variants of the 1D9 mouse antibody. The synthetic human Fab consisted of variable domain sequences derived from the consensus sequences for the most abundant human subclasses ($V_L\kappa$ subgroup I and $V_H$ subgroup III) and human constant regions (REI human $\kappa_1$ light chain $C_L$ and IgG1 $C_H1$). The synthetic human Fab sequences were subsequently inserted into a single *E. coli* expression vector to generate a dicistronic construct for expression of either soluble or phage displayed functional Fab.

EXAMPLE 8

Generation of CDR-Grafted Fabs and Mouse-Human Chimeric Fabs

As a starting point for humanization, a CDR-grafted Fab was generated by grafting the six complementarity-determining regions (CDRs) of the parent 1D9 antibody onto the synthetic human Fab. Optimization of key framework residues within a CDR-graft Fab is often required for correct presentation of the murine CDRs by the human framework and hence retention of potent binding affinity. Chimeric Fab fragments are equivalent in their antigen binding properties to the fully murine Fab fragment so can be used to determine if the CDR-grafted Fab requires framework optimization. A mouse-human chimeric Fab fragment consisting of the murine 1D9 heavy and light chain variable regions fused to the corresponding synthetic human constant domains was therefore generated as a reference for antigen binding affinity.

EXAMPLE 9

Comparison of the Binding Affinities of the Chimeric and CDR-Grafted Fabs

The binding affinity of the CDR-grafted and chimeric Fabs for IL-13R.alpah.1 were compared in Competition based assays, both as phage displayed Fabs in an ELISA format (FIG. 11A) and as purified soluble protein by a BIACORE™ biosensor competition assay (FIG. 11B). The CDR-grafted Fab has similar affinity for IL-13R.alpha.1 as the reference murine-human chimeric Fab. This indicates that the CDR-graft Fab does not require optimization of the framework residues and can be considered humanized.

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

TABLE 2

Response of transfected (FLAG-tagged IL-13Rα1-gp130 and IL-4Rα-gp130 and picked 293A12 colonies to LIF, IL-13 and IL-4

| Line# | Med | LIF* | IL-13 | IL-4 |
|---|---|---|---|---|
| 3.1.1 | 6791 | 61220 | 7381 | 12469 |
| 3.1.2 | 3539 | 42150 | 34094 (9.6) | 53998 (15.2) |
| 2.3.1 | 4626 | 43264 | 4383 | 4458 |
| 2.3.2 | 5850 | 52813 | 5377 | 5252 |
| 1.2.2 | 4921 | 45047 | 15093 (3.1) | 29866 (6.1) |
| 1.2.3 | 7222 | 159076 | 7183 | 7298 |
| 3.2.4* | 7783 | 61163 | 42046 (5.4) | 117971 (15.1) |
| 3.2.5 | 6823 | 62906 | 73145 (10.7) | 129369 (18.9) |
| 3.2.6 | 7849 | 67302 | 8307 | 16826 |
| 3.2.7 | 21589 | 163102 | 88581 (4.1) | 136760 (6.3) |
| 3.2.8 | 10698 | 89447 | 10352 | 12778 |
| 3.2.9 | 4093 | 45747 | 4141 | 4530 |

*LIF, IL-13 and IL-4 all used at a final concentration of 100 ng/ml, 24 hr assay.
*Representative data, 12 of 56 colonies assessed.

TABLE 3

Affinity (KD) of chimeric mouse and human IL-13Rα1-Fc proteins for immobilized mouse and human IL-13

| | Chimeric receptor* | |
|---|---|---|
| | mIL-13Rα1-Fc | hIL-13Rα1-Fc |
| Mouse IL-13 | 0.536 nM | 15.11 nM |
| Human IL-13 | 0.784 nM | 5.93 nM |

Bibliography

Ahdieh et al., *Am J. Physiol. Cell Physiol.* 281(6): C2029-2038, 2000
Akaiwa et al., *Cytokine* 13: 75-84, 2001
Antibodies: A Laboratory Manual, Harlow and Land (eds.), Cold Spring Harbor Laboratory Press, Cold Spring Harbor, N.Y., 1988
Bailer et al., *Eur. J. Immunol.* 30(5): 1340-1349, 2000
Bailer et al., *J. Immunol.* 162(12): 7534-7542, 1999
Bird, Science 242: 423, 1988
Callard et al., *Immunology Today* 17(3): 108, 1996
Danahay et al., *Am. J. Physiol. Lung Cell Mol. Physiol.* 282 (2): L226-236, 2002
David et al., *Oncogene* 20(46): 6660-6668, 2001
Gauchat et al., *Eur. J. Immunol.* 28: 4286-4298, 1998
Gauchat et al., *Eur. J. Immunol.* 30: 3157-3164, 2000
Howard et al., *Am J Hum Genet* 70(1): 230-236, 2002
Howard et al., *Am. J. Hum. Genet.* 70(1): 230-236, 2002
Huston et al., *Proc. Natl. Acad. Sci. USA* 85: 5879, 1988
Kabat et al. in Sequences of Proteins of Immunological Interest, 5th Ed., US Dept. of Health and Human Services, PHS, NIH, NIH Publication No. 91-3242, 1991
Kortt et al., *Protein Engineering* 10: 423, 1997
Larrick et al., *Bio/Technology* 7: 934, 1989
Liu et al., *Proc. Natl. Acad. Sci. USA* 84: 3439, 1987
Monoclonal Antibodies, Hybridomas: A New Dimension in Biological Analyses, Kennet et al. (eds.), Plenum Press, New York, 1980
Morris et al., *J. Biol. Chem.* 274: 418-423, 1999
Morse et al., *Am. J. Physiol. Lung Cell Mol. Physiol.* 282(1): L44-49, 2002
Noguchi et al., *Hum Immunol* 62(11): 1251-1257, 2001
Perez et al., *J. Immunol.* 168(3): 1428-1434, 2002
Riechmann et al., *Nature* 332: 323, 1988
Ward et al., *Nature* 334: 544, 1989
Winter and Harris, *TIPS* 14: 139, 1993

The invention claimed is:

1. An isolated monoclonal antibody or an antigen-binding fragment thereof which competes with monoclonal antibody 1D9 produced by the hybridoma deposited at the European Collection of Cell Cultures (ECACC) under Accession No. 03032101 for binding to the IL-13Rα1 chain as set forth in SEQ ID NO: 4, wherein said antibody or antigen-binding fragment thereof antagonizes IL-13 receptor-mediated signaling by IL-13 and IL-4.

2. The antibody or fragment of claim 1, wherein said antibody is a chimeric, human, or humanized antibody.

3. A composition comprising a monoclonal antibody or antigen binding fragment thereof which competes with monoclonal antibody 1D9 produced by the hybridoma deposited at the European Collection of Cell Cultures (ECACC) under Accession No. 03032101 for binding to the IL-13Rα1 chain as set forth in SEQ ID NO:4, wherein said antibody or antigen-binding fragment thereof antagonizes IL-13 receptor-mediated signaling by IL-13 and IL-4, and a pharmaceutically acceptable carrier.

4. The composition of claim 3, wherein said antibody is a chimeric, human, or humanized antibody.

* * * * *

SEQUENCE LISTING

<160> NUMBER OF SEQ ID NOS: 28

<210> SEQ ID NO 1
<211> LENGTH: 2478
<212> TYPE: DNA
<213> ORGANISM: human
<220> FEATURE:
<221> NAME/KEY: CDS
<222> LOCATION: (1)..(2478)
<223> OTHER INFORMATION:

<400> SEQUENCE: 1 atg ggg tgg ctt tgc tct ggg ctc ctg ttc cct gtg agc tgc ctg gtc        48

```
    Met Gly Trp Leu Cys Ser Gly Leu Leu Phe Pro Val Ser Cys Leu Val
    1               5                   10                  15 ctg ctg cag gtg gca agc tct ggg aac atg aag gtc ttg cag gag ccc         96
Leu Leu Gln Val Ala Ser Ser Gly Asn Met Lys Val Leu Gln Glu Pro
            20                  25                  30 acc tgc gtc tcc gac tac atg agc atc tct act tgc gag tgg aag atg         144
Thr Cys Val Ser Asp Tyr Met Ser Ile Ser Thr Cys Glu Trp Lys Met
            35                  40                  45 aat ggt ccc acc aat tgc agc acc gag ctc cgc ctg ttg tac cag ctg         192
Asn Gly Pro Thr Asn Cys Ser Thr Glu Leu Arg Leu Leu Tyr Gln Leu
    50                  55                  60 gtt ttt ctg ctc tcc gaa gcc cac acg tgt atc cct gag aac aac gga         240
Val Phe Leu Leu Ser Glu Ala His Thr Cys Ile Pro Glu Asn Asn Gly
65              70                  75                  80 ggc gcg ggg tgc gtg tgc cac ctc ctc atg gat gac gtg gtc agt gcg         288
Gly Ala Gly Cys Val Cys His Leu Leu Met Asp Asp Val Val Ser Ala
                85                  90                  95 gat aac tat aca ctg gac ctg tgg gct ggg cag cag ctg ctg tgg aag         336
Asp Asn Tyr Thr Leu Asp Leu Trp Ala Gly Gln Gln Leu Leu Trp Lys
            100                 105                 110 ggc tcc ttc aag ccc agc gag cat gtg aaa ccc agg gcc cca gga aac         384
Gly Ser Phe Lys Pro Ser Glu His Val Lys Pro Arg Ala Pro Gly Asn
        115                 120                 125 ctg aca gtt cac acc aat gtc tcc gac act ctg ctg ctg acc tgg agc         432
Leu Thr Val His Thr Asn Val Ser Asp Thr Leu Leu Leu Thr Trp Ser
    130                 135                 140 aac ccg tat ccc cct gac aat tac ctg tat aat cat ctc acc tat gca         480
Asn Pro Tyr Pro Pro Asp Asn Tyr Leu Tyr Asn His Leu Thr Tyr Ala
145                 150                 155                 160 gtc aac att tgg agt gaa aac gac ccg gca gat ttc aga atc tat aac         528
Val Asn Ile Trp Ser Glu Asn Asp Pro Ala Asp Phe Arg Ile Tyr Asn
                165                 170                 175 gtg acc tac cta gaa ccc tcc ctc cgc atc gca gcc agc acc ctg aag         576
Val Thr Tyr Leu Glu Pro Ser Leu Arg Ile Ala Ala Ser Thr Leu Lys
            180                 185                 190 tct ggg att tcc tac agg gca cgg gtg agg gcc tgg gct cag tgc tat         624
Ser Gly Ile Ser Tyr Arg Ala Arg Val Arg Ala Trp Ala Gln Cys Tyr
        195                 200                 205 aac acc acc tgg agt gag tgg agc ccc agc acc aag tgg cac aac tcc         672
Asn Thr Thr Trp Ser Glu Trp Ser Pro Ser Thr Lys Trp His Asn Ser
    210                 215                 220 tac agg gag ccc ttc gag cag cac ctc ctg ctg ggc gtc agc gtt tcc         720
Tyr Arg Glu Pro Phe Glu Gln His Leu Leu Leu Gly Val Ser Val Ser
225                 230                 235                 240 tgc att gtc atc ctg gcc gtc tgc ctg ttg tgc tat gtc agc atc acc         768
Cys Ile Val Ile Leu Ala Val Cys Leu Leu Cys Tyr Val Ser Ile Thr
                245                 250                 255 aag att aag aaa gaa tgg tgg gat cag att ccc aac cca gcc cgc agc         816
Lys Ile Lys Lys Glu Trp Trp Asp Gln Ile Pro Asn Pro Ala Arg Ser
            260                 265                 270 cgc ctc gtg gct ata ata atc cag gat gct cag ggg tca cag tgg gag         864
Arg Leu Val Ala Ile Ile Ile Gln Asp Ala Gln Gly Ser Gln Trp Glu
        275                 280                 285 aag cgg tcc cga ggc cag gaa cca gcc aag tgc cca cac tgg aag aat         912
Lys Arg Ser Arg Gly Gln Glu Pro Ala Lys Cys Pro His Trp Lys Asn
    290                 295                 300 tgt ctt acc aag ctc ttg ccc tgt ttt ctg gag cac aac atg aaa agg         960
Cys Leu Thr Lys Leu Leu Pro Cys Phe Leu Glu His Asn Met Lys Arg
305                 310                 315                 320 gat gaa gat cct cac aag gct gcc aaa gag atg cct ttc cag ggc tct         1008
```

-continued

```
                Asp Glu Asp Pro His Lys Ala Ala Lys Glu Met Pro Phe Gln Gly Ser
                                325                 330                 335 gga aaa tca gca tgg tgc cca gtg gag atc agc aag aca gtc ctc tgg      1056
Gly Lys Ser Ala Trp Cys Pro Val Glu Ile Ser Lys Thr Val Leu Trp
            340                 345                 350 cca gag agc atc agc gtg gtg cga tgt gtg gag ttg ttt gag gcc ccg      1104
Pro Glu Ser Ile Ser Val Val Arg Cys Val Glu Leu Phe Glu Ala Pro
            355                 360                 365 gtg gag tgt gag gag gag gag gta gag gaa gaa aaa ggg agc ttc          1152
Val Glu Cys Glu Glu Glu Glu Val Glu Glu Glu Lys Gly Ser Phe
        370                 375                 380 tgt gca tcg cct gag agc agc agg gat gac ttc cag gag gga agg gag      1200
Cys Ala Ser Pro Glu Ser Ser Arg Asp Asp Phe Gln Glu Gly Arg Glu
385                 390                 395                 400 ggc att gtg gcc cgg cta aca gag agc ctg ttc ctg gac ctg ctc gga      1248
Gly Ile Val Ala Arg Leu Thr Glu Ser Leu Phe Leu Asp Leu Leu Gly
                405                 410                 415 gag gag aat ggg ggc ttt tgc cag cag gac atg ggg gag tca tgc ctt      1296
Glu Glu Asn Gly Gly Phe Cys Gln Gln Asp Met Gly Glu Ser Cys Leu
            420                 425                 430 ctt cca cct tcg gga agt acg agt gct cac atg ccc tgg gat gag ttc      1344
Leu Pro Pro Ser Gly Ser Thr Ser Ala His Met Pro Trp Asp Glu Phe
        435                 440                 445 cca agt gca ggg ccc aag gag gca cct ccc tgg ggc aag gag cag cct      1392
Pro Ser Ala Gly Pro Lys Glu Ala Pro Pro Trp Gly Lys Glu Gln Pro
    450                 455                 460 ctc cac ctg gag cca agt cct cct gcc agc ccg acc cag agt cca gac      1440
Leu His Leu Glu Pro Ser Pro Pro Ala Ser Pro Thr Gln Ser Pro Asp
465                 470                 475                 480 aac ctg act tgc aca gag acg ccc ctc gtc atc gca ggc aac cct gct      1488
Asn Leu Thr Cys Thr Glu Thr Pro Leu Val Ile Ala Gly Asn Pro Ala
                485                 490                 495 tac cgc agc ttc agc aac tcc ctg agc cag tca ccg tgt ccc aga gag      1536
Tyr Arg Ser Phe Ser Asn Ser Leu Ser Gln Ser Pro Cys Pro Arg Glu
            500                 505                 510 ctg ggt cca gac cca ctg ctg gcc aga cac ctg gag gaa gta gaa ccc      1584
Leu Gly Pro Asp Pro Leu Leu Ala Arg His Leu Glu Glu Val Glu Pro
        515                 520                 525 gag atg ccc tgt gtc ccc cag ctc tct gag cca acc act gtg ccc caa      1632
Glu Met Pro Cys Val Pro Gln Leu Ser Glu Pro Thr Thr Val Pro Gln
    530                 535                 540 cct gag cca gaa acc tgg gag cag atc ctc cgc cga aat gtc ctc cag      1680
Pro Glu Pro Glu Thr Trp Glu Gln Ile Leu Arg Arg Asn Val Leu Gln
545                 550                 555                 560 cat ggg gca gct gca gcc ccc gtc tcg gcc ccc acc agt ggc tat cag      1728
His Gly Ala Ala Ala Ala Pro Val Ser Ala Pro Thr Ser Gly Tyr Gln
                565                 570                 575 gag ttt gta cat gcg gtg gag cag ggt ggc acc cag gcc agt gcg gtg      1776
Glu Phe Val His Ala Val Glu Gln Gly Gly Thr Gln Ala Ser Ala Val
            580                 585                 590 gtg ggc ttg ggt ccc cca gga gag gct ggt tac aag gcc ttc tca agc      1824
Val Gly Leu Gly Pro Pro Gly Glu Ala Gly Tyr Lys Ala Phe Ser Ser
        595                 600                 605 ctg ctt gcc agc agt gct gtg tcc cca gag aaa tgt ggg ttt ggg gct      1872
Leu Leu Ala Ser Ser Ala Val Ser Pro Glu Lys Cys Gly Phe Gly Ala
    610                 615                 620 agc agt ggg gaa gag ggg tat aag cct ttc caa gac ctc att cct ggc      1920
Ser Ser Gly Glu Glu Gly Tyr Lys Pro Phe Gln Asp Leu Ile Pro Gly
625                 630                 635                 640 tgc cct ggg gac cct gcc cca gtc cct gtc ccc ttg ttc acc ttt gga      1968
```

```
                Cys Pro Gly Asp Pro Ala Pro Val Pro Val Pro Leu Phe Thr Phe Gly
                                645                 650                 655 ctg gac agg gag cca cct cgc agt ccg cag agc tca cat ctc cca agc              2016
Leu Asp Arg Glu Pro Pro Arg Ser Pro Gln Ser Ser His Leu Pro Ser
            660                 665                 670 agc tcc cca gag cac ctg ggt ctg gag ccg ggg gaa aag gta gag gac              2064
Ser Ser Pro Glu His Leu Gly Leu Glu Pro Gly Glu Lys Val Glu Asp
675                 680                 685 atg cca aag ccc cca ctt ccc cag gag cag gcc aca gac ccc ctt gtg              2112
Met Pro Lys Pro Pro Leu Pro Gln Glu Gln Ala Thr Asp Pro Leu Val
        690                 695                 700 gac agc ctg ggc agt ggc att gtc tac tca gcc ctt acc tgc cac ctg              2160
Asp Ser Leu Gly Ser Gly Ile Val Tyr Ser Ala Leu Thr Cys His Leu
705                 710                 715                 720 tgc ggc cac ctg aaa cag tgt cat ggc cag gag gat ggt ggc cag acc              2208
Cys Gly His Leu Lys Gln Cys His Gly Gln Glu Asp Gly Gly Gln Thr
                725                 730                 735 cct gtc atg gcc agt cct tgc tgt ggc tgc tgc tgt gga gac agg tcc              2256
Pro Val Met Ala Ser Pro Cys Cys Gly Cys Cys Cys Gly Asp Arg Ser
            740                 745                 750 tcg ccc cct aca acc ccc ctg agg gcc cca gac ccc tct cca ggt ggg              2304
Ser Pro Pro Thr Thr Pro Leu Arg Ala Pro Asp Pro Ser Pro Gly Gly
        755                 760                 765 gtt cca ctg gag gcc agt ctg tgt ccg gcc tcc ctg gca ccc tcg ggc              2352
Val Pro Leu Glu Ala Ser Leu Cys Pro Ala Ser Leu Ala Pro Ser Gly
770                 775                 780 atc tca gag aag agt aaa tcc tca tcc ttc cat cct gcc cct ggc              2400
Ile Ser Glu Lys Ser Lys Ser Ser Ser Phe His Pro Ala Pro Gly
785                 790                 795                 800 aat gct cag agc tca agc cag acc ccc aaa atc gtg aac ttt gtc tcc              2448
Asn Ala Gln Ser Ser Ser Gln Thr Pro Lys Ile Val Asn Phe Val Ser
                805                 810                 815 gtg gga ccc aca tac atg agg gtc tct tag                                      2478
Val Gly Pro Thr Tyr Met Arg Val Ser
            820                 825

<210> SEQ ID NO 2
<211> LENGTH: 825
<212> TYPE: PRT
<213> ORGANISM: human

<400> SEQUENCE: 2

Met Gly Trp Leu Cys Ser Gly Leu Leu Phe Pro Val Ser Cys Leu Val
1               5                   10                  15

Leu Leu Gln Val Ala Ser Ser Gly Asn Met Lys Val Leu Gln Glu Pro
            20                  25                  30

Thr Cys Val Ser Asp Tyr Met Ser Ile Ser Thr Cys Glu Trp Lys Met
        35                  40                  45

Asn Gly Pro Thr Asn Cys Ser Thr Glu Leu Arg Leu Leu Tyr Gln Leu
    50                  55                  60

Val Phe Leu Leu Ser Glu Ala His Thr Cys Ile Pro Glu Asn Asn Gly
65                  70                  75                  80

Gly Ala Gly Cys Val Cys His Leu Leu Met Asp Asp Val Val Ser Ala
                85                  90                  95

Asp Asn Tyr Thr Leu Asp Leu Trp Ala Gly Gln Gln Leu Leu Trp Lys
            100                 105                 110

Gly Ser Phe Lys Pro Ser Glu His Val Lys Pro Arg Ala Pro Gly Asn
        115                 120                 125

Leu Thr Val His Thr Asn Val Ser Asp Thr Leu Leu Leu Thr Trp Ser
```

```
                130                 135                 140
Asn Pro Tyr Pro Pro Asp Asn Tyr Leu Tyr Asn His Leu Thr Tyr Ala
145                 150                 155                 160

Val Asn Ile Trp Ser Glu Asn Asp Pro Ala Asp Phe Arg Ile Tyr Asn
                165                 170                 175

Val Thr Tyr Leu Glu Pro Ser Leu Arg Ile Ala Ala Ser Thr Leu Lys
                180                 185                 190

Ser Gly Ile Ser Tyr Arg Ala Arg Val Arg Ala Trp Ala Gln Cys Tyr
                195                 200                 205

Asn Thr Thr Trp Ser Glu Trp Ser Pro Ser Thr Lys Trp His Asn Ser
210                 215                 220

Tyr Arg Glu Pro Phe Glu Gln His Leu Leu Leu Gly Val Ser Val Ser
225                 230                 235                 240

Cys Ile Val Ile Leu Ala Val Cys Leu Leu Cys Tyr Val Ser Ile Thr
                245                 250                 255

Lys Ile Lys Lys Glu Trp Trp Asp Gln Ile Pro Asn Pro Ala Arg Ser
                260                 265                 270

Arg Leu Val Ala Ile Ile Gln Asp Ala Gln Gly Ser Gln Trp Glu
                275                 280                 285

Lys Arg Ser Arg Gly Gln Glu Pro Ala Lys Cys Pro His Trp Lys Asn
290                 295                 300

Cys Leu Thr Lys Leu Leu Pro Cys Phe Leu Glu His Asn Met Lys Arg
305                 310                 315                 320

Asp Glu Asp Pro His Lys Ala Ala Lys Glu Met Pro Phe Gln Gly Ser
                325                 330                 335

Gly Lys Ser Ala Trp Cys Pro Val Glu Ile Ser Lys Thr Val Leu Trp
                340                 345                 350

Pro Glu Ser Ile Ser Val Val Arg Cys Val Glu Leu Phe Glu Ala Pro
                355                 360                 365

Val Glu Cys Glu Glu Glu Glu Val Glu Glu Lys Gly Ser Phe
                370                 375                 380

Cys Ala Ser Pro Glu Ser Ser Arg Asp Asp Phe Gln Glu Gly Arg Glu
385                 390                 395                 400

Gly Ile Val Ala Arg Leu Thr Glu Ser Leu Phe Leu Asp Leu Leu Gly
                405                 410                 415

Glu Glu Asn Gly Gly Phe Cys Gln Gln Asp Met Gly Glu Ser Cys Leu
                420                 425                 430

Leu Pro Pro Ser Gly Ser Thr Ser Ala His Met Pro Trp Asp Glu Phe
                435                 440                 445

Pro Ser Ala Gly Pro Lys Glu Ala Pro Pro Trp Gly Lys Glu Gln Pro
450                 455                 460

Leu His Leu Glu Pro Ser Pro Pro Ala Ser Pro Thr Gln Ser Pro Asp
465                 470                 475                 480

Asn Leu Thr Cys Thr Glu Thr Pro Leu Val Ile Ala Gly Asn Pro Ala
                485                 490                 495

Tyr Arg Ser Phe Ser Asn Ser Leu Ser Gln Ser Pro Cys Pro Arg Glu
                500                 505                 510

Leu Gly Pro Asp Pro Leu Leu Ala Arg His Leu Glu Glu Val Glu Pro
                515                 520                 525

Glu Met Pro Cys Val Pro Gln Leu Ser Glu Pro Thr Thr Val Pro Gln
                530                 535                 540

Pro Glu Pro Glu Thr Trp Glu Gln Ile Leu Arg Arg Asn Val Leu Gln
545                 550                 555                 560
```

-continued

```
His Gly Ala Ala Ala Ala Pro Val Ser Ala Pro Thr Ser Gly Tyr Gln
            565                 570                 575

Glu Phe Val His Ala Val Glu Gln Gly Thr Gln Ala Ser Ala Val
        580                 585                 590

Val Gly Leu Gly Pro Pro Gly Glu Ala Gly Tyr Lys Ala Phe Ser Ser
    595                 600                 605

Leu Leu Ala Ser Ser Ala Val Ser Pro Glu Lys Cys Gly Phe Gly Ala
        610                 615                 620

Ser Ser Gly Glu Glu Gly Tyr Lys Pro Phe Gln Asp Leu Ile Pro Gly
625                 630                 635                 640

Cys Pro Gly Asp Pro Ala Pro Val Pro Val Pro Leu Phe Thr Phe Gly
            645                 650                 655

Leu Asp Arg Glu Pro Pro Arg Ser Pro Gln Ser Ser His Leu Pro Ser
        660                 665                 670

Ser Ser Pro Glu His Leu Gly Leu Glu Pro Gly Glu Lys Val Glu Asp
            675                 680                 685

Met Pro Lys Pro Pro Leu Pro Gln Glu Gln Ala Thr Asp Pro Leu Val
        690                 695                 700

Asp Ser Leu Gly Ser Gly Ile Val Tyr Ser Ala Leu Thr Cys His Leu
705                 710                 715                 720

Cys Gly His Leu Lys Gln Cys His Gly Gln Glu Asp Gly Gly Gln Thr
            725                 730                 735

Pro Val Met Ala Ser Pro Cys Cys Gly Cys Cys Cys Gly Asp Arg Ser
        740                 745                 750

Ser Pro Pro Thr Thr Pro Leu Arg Ala Pro Asp Pro Ser Pro Gly Gly
        755                 760                 765

Val Pro Leu Glu Ala Ser Leu Cys Pro Ala Ser Leu Ala Pro Ser Gly
    770                 775                 780

Ile Ser Glu Lys Ser Lys Ser Ser Ser Phe His Pro Ala Pro Gly
785                 790                 795                 800

Asn Ala Gln Ser Ser Ser Gln Thr Pro Lys Ile Val Asn Phe Val Ser
            805                 810                 815

Val Gly Pro Thr Tyr Met Arg Val Ser
        820                 825

<210> SEQ ID NO 3
<211> LENGTH: 1284
<212> TYPE: DNA
<213> ORGANISM: human
<220> FEATURE:
<221> NAME/KEY: CDS
<222> LOCATION: (1)..(1284)
<223> OTHER INFORMATION:

<400> SEQUENCE: 3 atg gag tgg ccg gcg cgg ctc tgc ggg ctg tgg gcg ctg ctc ctc tgc     48
Met Glu Trp Pro Ala Arg Leu Cys Gly Leu Trp Ala Leu Leu Leu Cys
1               5                   10                  15 gcc ggc ggc ggg ggc ggg ggc ggg ggc gcc gcg cct acg gaa act cag     96
Ala Gly Gly Gly Gly Gly Gly Gly Gly Ala Ala Pro Thr Glu Thr Gln
            20                  25                  30 cca cct gtg aca aat ttg agt gtc tct gtt gaa aac ctc tgc aca gta    144
Pro Pro Val Thr Asn Leu Ser Val Ser Val Glu Asn Leu Cys Thr Val
        35                  40                  45 ata tgg aca tgg aat cca ccc gag gga gcc agc tca aat tgt agt cta    192
Ile Trp Thr Trp Asn Pro Pro Glu Gly Ala Ser Ser Asn Cys Ser Leu
    50                  55                  60 tgg tat ttt agt cat ttt ggc gac aaa caa gat aag aaa ata gct ccg    240
```

-continued

| | | |
|---|---|---|
| Trp Tyr Phe Ser His Phe Gly Asp Lys Gln Asp Lys Lys Ile Ala Pro<br>65                                   70                             75                             80 | | |
| gaa act cgt cgt tca ata gaa gta ccc ctg aat gag agg att tgt ctg<br>Glu Thr Arg Arg Ser Ile Glu Val Pro Leu Asn Glu Arg Ile Cys Leu<br>                            85                             90                             95 | | 288 |
| caa gtg ggg tcc cag tgt agc acc aat gag agt gag aag cct agc att<br>Gln Val Gly Ser Gln Cys Ser Thr Asn Glu Ser Glu Lys Pro Ser Ile<br>              100                        105                        110 | | 336 |
| ttg gtt gaa aaa tgc atc tca ccc cca gaa ggt gat cct gag tct gct<br>Leu Val Glu Lys Cys Ile Ser Pro Pro Glu Gly Asp Pro Glu Ser Ala<br>              115                        120                        125 | | 384 |
| gtg act gag ctt caa tgc att tgg cac aac ctg agc tac atg aag tgt<br>Val Thr Glu Leu Gln Cys Ile Trp His Asn Leu Ser Tyr Met Lys Cys<br>130                              135                             140 | | 432 |
| tct tgg ctc cct gga agg aat acc agt ccc gac act aac tat act ctc<br>Ser Trp Leu Pro Gly Arg Asn Thr Ser Pro Asp Thr Asn Tyr Thr Leu<br>145                              150                             155                        160 | | 480 |
| tac tat tgg cac aga agc ctg gaa aaa att cat caa tgt gaa aac atc<br>Tyr Tyr Trp His Arg Ser Leu Glu Lys Ile His Gln Cys Glu Asn Ile<br>                            165                        170                        175 | | 528 |
| ttt aga gaa ggc caa tac ttt ggt tgt tcc ttt gat ctg acc aaa gtg<br>Phe Arg Glu Gly Gln Tyr Phe Gly Cys Ser Phe Asp Leu Thr Lys Val<br>              180                        185                        190 | | 576 |
| aag gat tcc agt ttt gaa caa cac agt gtc caa ata atg gtc aag gat<br>Lys Asp Ser Ser Phe Glu Gln His Ser Val Gln Ile Met Val Lys Asp<br>                            195                        200                        205 | | 624 |
| aat gca gga aaa att aaa cca tcc ttc aat ata gtg cct tta act tcc<br>Asn Ala Gly Lys Ile Lys Pro Ser Phe Asn Ile Val Pro Leu Thr Ser<br>210                              215                             220 | | 672 |
| cgt gtg aaa cct gat cct cca cat att aaa aac ctc tcc ttc cac aat<br>Arg Val Lys Pro Asp Pro Pro His Ile Lys Asn Leu Ser Phe His Asn<br>225                              230                             235                        240 | | 720 |
| gat gac cta tat gtg caa tgg gag aat cca cag aat ttt att agc aga<br>Asp Asp Leu Tyr Val Gln Trp Glu Asn Pro Gln Asn Phe Ile Ser Arg<br>                            245                        250                        255 | | 768 |
| tgc cta ttt tat gaa gta gaa gtc aat aac agc caa act gag aca cat<br>Cys Leu Phe Tyr Glu Val Glu Val Asn Asn Ser Gln Thr Glu Thr His<br>            260                        265                        270 | | 816 |
| aat gtt ttc tac gtc caa gag gct aaa tgt gag aat cca gaa ttt gag<br>Asn Val Phe Tyr Val Gln Glu Ala Lys Cys Glu Asn Pro Glu Phe Glu<br>            275                        280                        285 | | 864 |
| aga aat gtg gag aat aca tct tgt ttc atg gtc cct ggt gtt ctt cct<br>Arg Asn Val Glu Asn Thr Ser Cys Phe Met Val Pro Gly Val Leu Pro<br>            290                        295                        300 | | 912 |
| gat act ttg aac aca gtc aga ata aga gtc aaa aca aat aag tta tgc<br>Asp Thr Leu Asn Thr Val Arg Ile Arg Val Lys Thr Asn Lys Leu Cys<br>305                              310                             315                        320 | | 960 |
| tat gag gat gac aaa ctc tgg agt aat tgg agc caa gaa atg agt ata<br>Tyr Glu Asp Asp Lys Leu Trp Ser Asn Trp Ser Gln Glu Met Ser Ile<br>                            325                        330                        335 | | 1008 |
| ggt aag aag cgc aat tcc aca ctc tac ata acc atg tta ctc att gtt<br>Gly Lys Lys Arg Asn Ser Thr Leu Tyr Ile Thr Met Leu Leu Ile Val<br>            340                        345                        350 | | 1056 |
| cca gtc atc gtc gca gat gca atc ata gta ctc ctg ctt tac cta aaa<br>Pro Val Ile Val Ala Asp Ala Ile Ile Val Leu Leu Leu Tyr Leu Lys<br>            355                        360                        365 | | 1104 |
| agg ctc aag att att ata ttc cct cca att cct gat cct ggc aag att<br>Arg Leu Lys Ile Ile Ile Phe Pro Pro Ile Pro Asp Pro Gly Lys Ile<br>370                              375                             380 | | 1152 |
| ttt aaa gaa atg ttt gga gac cag aat gat gat act ctg cac tgg aag | | 1200 |

```
Phe Lys Glu Met Phe Gly Asp Gln Asn Asp Asp Thr Leu His Trp Lys
385                 390                 395                 400 aag tac gac atc tat gag aag caa acc aag gag gaa acc gac tct gta    1248
Lys Tyr Asp Ile Tyr Glu Lys Gln Thr Lys Glu Glu Thr Asp Ser Val
                405                 410                 415 gtg ctg ata gaa aac ctg aag aaa gcc tct cag tga                    1284
Val Leu Ile Glu Asn Leu Lys Lys Ala Ser Gln
            420                 425

<210> SEQ ID NO 4
<211> LENGTH: 427
<212> TYPE: PRT
<213> ORGANISM: human

<400> SEQUENCE: 4

Met Glu Trp Pro Ala Arg Leu Cys Gly Leu Trp Ala Leu Leu Leu Cys
1               5                   10                  15

Ala Gly Gly Gly Gly Gly Gly Gly Ala Ala Pro Thr Glu Thr Gln
            20                  25                  30

Pro Pro Val Thr Asn Leu Ser Val Ser Val Glu Asn Leu Cys Thr Val
                35                  40                  45

Ile Trp Thr Trp Asn Pro Pro Glu Gly Ala Ser Ser Asn Cys Ser Leu
50                  55                  60

Trp Tyr Phe Ser His Phe Gly Asp Lys Gln Asp Lys Lys Ile Ala Pro
65                  70                  75                  80

Glu Thr Arg Arg Ser Ile Glu Val Pro Leu Asn Glu Arg Ile Cys Leu
                85                  90                  95

Gln Val Gly Ser Gln Cys Ser Thr Asn Glu Ser Glu Lys Pro Ser Ile
            100                 105                 110

Leu Val Glu Lys Cys Ile Ser Pro Pro Glu Gly Asp Pro Glu Ser Ala
        115                 120                 125

Val Thr Glu Leu Gln Cys Ile Trp His Asn Leu Ser Tyr Met Lys Cys
    130                 135                 140

Ser Trp Leu Pro Gly Arg Asn Thr Ser Pro Asp Thr Asn Tyr Thr Leu
145                 150                 155                 160

Tyr Tyr Trp His Arg Ser Leu Glu Lys Ile His Gln Cys Glu Asn Ile
                165                 170                 175

Phe Arg Glu Gly Gln Tyr Phe Gly Cys Ser Phe Asp Leu Thr Lys Val
            180                 185                 190

Lys Asp Ser Ser Phe Glu Gln His Ser Val Gln Ile Met Val Lys Asp
        195                 200                 205

Asn Ala Gly Lys Ile Lys Pro Ser Phe Asn Ile Val Pro Leu Thr Ser
    210                 215                 220

Arg Val Lys Pro Asp Pro Pro His Ile Lys Asn Leu Ser Phe His Asn
225                 230                 235                 240

Asp Asp Leu Tyr Val Gln Trp Glu Asn Pro Gln Asn Phe Ile Ser Arg
                245                 250                 255

Cys Leu Phe Tyr Glu Val Glu Val Asn Asn Ser Gln Thr Glu Thr His
            260                 265                 270

Asn Val Phe Tyr Val Gln Glu Ala Lys Cys Glu Asn Pro Glu Phe Glu
        275                 280                 285

Arg Asn Val Glu Asn Thr Ser Cys Phe Met Val Pro Gly Val Leu Pro
    290                 295                 300

Asp Thr Leu Asn Thr Val Arg Ile Arg Val Lys Thr Asn Lys Leu Cys
305                 310                 315                 320

Tyr Glu Asp Asp Lys Leu Trp Ser Asn Trp Ser Gln Glu Met Ser Ile
```

```
                325                 330                 335
Gly Lys Lys Arg Asn Ser Thr Leu Tyr Ile Thr Met Leu Leu Ile Val
            340                 345                 350

Pro Val Ile Val Ala Asp Ala Ile Ile Val Leu Leu Leu Tyr Leu Lys
            355                 360                 365

Arg Leu Lys Ile Ile Ile Phe Pro Ile Pro Asp Pro Gly Lys Ile
        370                 375                 380

Phe Lys Glu Met Phe Gly Asp Gln Asn Asp Thr Leu His Trp Lys
385                 390                 395                 400

Lys Tyr Asp Ile Tyr Glu Lys Gln Thr Lys Glu Glu Thr Asp Ser Val
                405                 410                 415

Val Leu Ile Glu Asn Leu Lys Lys Ala Ser Gln
            420                 425

<210> SEQ ID NO 5
<211> LENGTH: 2757
<212> TYPE: DNA
<213> ORGANISM: human
<220> FEATURE:
<221> NAME/KEY: CDS
<222> LOCATION: (1)..(2757)
<223> OTHER INFORMATION:

<400> SEQUENCE: 5 atg ttg acg ttg cag act tgg gta gtg caa gcc ttg ttt att ttc ctc      48
Met Leu Thr Leu Gln Thr Trp Val Val Gln Ala Leu Phe Ile Phe Leu
1               5                   10                  15 acc act gaa tct aca ggt gaa ctt cta gat cca tgt ggt tat atc agt     96
Thr Thr Glu Ser Thr Gly Glu Leu Leu Asp Pro Cys Gly Tyr Ile Ser
                20                  25                  30 cct gaa tct cca gtt gta caa ctt cat tct aat ttc act gca gtt tgt    144
Pro Glu Ser Pro Val Val Gln Leu His Ser Asn Phe Thr Ala Val Cys
            35                  40                  45 gtg cta aag gaa aaa tgt atg gat tat ttt cat gta aat gct aat tac    192
Val Leu Lys Glu Lys Cys Met Asp Tyr Phe His Val Asn Ala Asn Tyr
        50                  55                  60 att gtc tgg aaa aca aac cat ttt act att cct aag gag caa tat act    240
Ile Val Trp Lys Thr Asn His Phe Thr Ile Pro Lys Glu Gln Tyr Thr
65                  70                  75                  80 atc ata aac aga aca gca tcc agt gtc acc ttt aca gat ata gct tca    288
Ile Ile Asn Arg Thr Ala Ser Ser Val Thr Phe Thr Asp Ile Ala Ser
                85                  90                  95 tta aat att cag ctc act tgc aac att ctt aca ttc gga cag ctt gaa    336
Leu Asn Ile Gln Leu Thr Cys Asn Ile Leu Thr Phe Gly Gln Leu Glu
                100                 105                 110 cag aat gtt tat gga atc aca ata att tcg ggc ttg cct cca gaa aaa    384
Gln Asn Val Tyr Gly Ile Thr Ile Ile Ser Gly Leu Pro Pro Glu Lys
            115                 120                 125 cct aaa aat ttg agt tgc att gtg aac gag ggg aag aaa atg agg tgt    432
Pro Lys Asn Leu Ser Cys Ile Val Asn Glu Gly Lys Lys Met Arg Cys
        130                 135                 140 gag tgg gat ggt gga agg gaa aca cac ttg gag aca aac ttc act tta    480
Glu Trp Asp Gly Gly Arg Glu Thr His Leu Glu Thr Asn Phe Thr Leu
145                 150                 155                 160 aaa tct gaa tgg gca aca cac aag ttt gct gat tgc aaa gca aaa cgt    528
Lys Ser Glu Trp Ala Thr His Lys Phe Ala Asp Cys Lys Ala Lys Arg
                165                 170                 175 gac acc ccc acc tca tgc act gtt gat tat tct act gtg tat ttt gtc    576
Asp Thr Pro Thr Ser Cys Thr Val Asp Tyr Ser Thr Val Tyr Phe Val
            180                 185                 190
```

```
aac att gaa gtc tgg gta gaa gca gag aat gcc ctt ggg aag gtt aca       624
Asn Ile Glu Val Trp Val Glu Ala Glu Asn Ala Leu Gly Lys Val Thr
        195                 200                 205 tca gat cat atc aat ttt gat cct gta tat aaa gtg aag ccc aat ccg       672
Ser Asp His Ile Asn Phe Asp Pro Val Tyr Lys Val Lys Pro Asn Pro
    210                 215                 220 cca cat aat tta tca gtg atc aac tca gag gaa ctg tct agt atc tta       720
Pro His Asn Leu Ser Val Ile Asn Ser Glu Glu Leu Ser Ser Ile Leu
225                 230                 235                 240 aaa ttg aca tgg acc aac cca agt att aag agt gtt ata ata cta aaa       768
Lys Leu Thr Trp Thr Asn Pro Ser Ile Lys Ser Val Ile Ile Leu Lys
            245                 250                 255 tat aac att caa tat agg acc aaa gat gcc tca act tgg agc cag att       816
Tyr Asn Ile Gln Tyr Arg Thr Lys Asp Ala Ser Thr Trp Ser Gln Ile
        260                 265                 270 cct cct gaa gac aca gca tcc acc cga tct tca ttc act gtc caa gac       864
Pro Pro Glu Asp Thr Ala Ser Thr Arg Ser Ser Phe Thr Val Gln Asp
    275                 280                 285 ctt aaa cct ttt aca gaa tat gtg ttt agg att cgc tgt atg aag gaa       912
Leu Lys Pro Phe Thr Glu Tyr Val Phe Arg Ile Arg Cys Met Lys Glu
290                 295                 300 gat ggt aag gga tac tgg agt gac tgg agt gaa gaa gca agt ggg atc       960
Asp Gly Lys Gly Tyr Trp Ser Asp Trp Ser Glu Glu Ala Ser Gly Ile
305                 310                 315                 320 acc tat gaa gat aga cca tct aaa gca cca agt ttc tgg tat aaa ata      1008
Thr Tyr Glu Asp Arg Pro Ser Lys Ala Pro Ser Phe Trp Tyr Lys Ile
            325                 330                 335 gat cca tcc cat act caa ggc tac aga act gta caa ctc gtg tgg aag      1056
Asp Pro Ser His Thr Gln Gly Tyr Arg Thr Val Gln Leu Val Trp Lys
        340                 345                 350 aca ttg cct cct ttt gaa gcc aat gga aaa atc ttg gat tat gaa gtg      1104
Thr Leu Pro Pro Phe Glu Ala Asn Gly Lys Ile Leu Asp Tyr Glu Val
    355                 360                 365 act ctc aca aga tgg aaa tca cat tta caa aat tac aca gtt aat gcc      1152
Thr Leu Thr Arg Trp Lys Ser His Leu Gln Asn Tyr Thr Val Asn Ala
370                 375                 380 aca aaa ctg aca gta aat ctc aca aat gat cgc tat cta gca acc cta      1200
Thr Lys Leu Thr Val Asn Leu Thr Asn Asp Arg Tyr Leu Ala Thr Leu
385                 390                 395                 400 aca gta aga aat ctt gtt ggc aaa tca gat gca gct gtt tta act atc      1248
Thr Val Arg Asn Leu Val Gly Lys Ser Asp Ala Ala Val Leu Thr Ile
            405                 410                 415 cct gcc tgt gac ttt caa gct act cac cct gta atg gat ctt aaa gca      1296
Pro Ala Cys Asp Phe Gln Ala Thr His Pro Val Met Asp Leu Lys Ala
        420                 425                 430 ttc ccc aaa gat aac atg ctt tgg gtg gaa tgg act act cca agg gaa      1344
Phe Pro Lys Asp Asn Met Leu Trp Val Glu Trp Thr Thr Pro Arg Glu
    435                 440                 445 tct gta aag aaa tat ata ctt gag tgg tgt gtg tta tca gat aaa gca      1392
Ser Val Lys Lys Tyr Ile Leu Glu Trp Cys Val Leu Ser Asp Lys Ala
450                 455                 460 ccc tgt atc aca gac tgg caa caa gaa gat ggt acc gtg cat cgc acc      1440
Pro Cys Ile Thr Asp Trp Gln Gln Glu Asp Gly Thr Val His Arg Thr
465                 470                 475                 480 tat tta aga ggg aac tta gca gag agc aaa tgc tat ttg ata aca gtt      1488
Tyr Leu Arg Gly Asn Leu Ala Glu Ser Lys Cys Tyr Leu Ile Thr Val
            485                 490                 495 act cca gta tat gct gat gga cca gga agc cct gaa tcc ata aag gca      1536
Thr Pro Val Tyr Ala Asp Gly Pro Gly Ser Pro Glu Ser Ile Lys Ala
        500                 505                 510
```

```
tac ctt aaa caa gct cca cct tcc aaa gga cct act gtt cgg aca aaa    1584
Tyr Leu Lys Gln Ala Pro Pro Ser Lys Gly Pro Thr Val Arg Thr Lys
        515                 520                 525 aaa gta ggg aaa aac gaa gct gtc tta gag tgg gac caa ctt cct gtt    1632
Lys Val Gly Lys Asn Glu Ala Val Leu Glu Trp Asp Gln Leu Pro Val
530                 535                 540 gat gtt cag aat gga ttt atc aga aat tat act ata ttt tat aga acc    1680
Asp Val Gln Asn Gly Phe Ile Arg Asn Tyr Thr Ile Phe Tyr Arg Thr
545                 550                 555                 560 atc att gga aat gaa act gct gtg aat gtg gat tct tcc cac aca gaa    1728
Ile Ile Gly Asn Glu Thr Ala Val Asn Val Asp Ser Ser His Thr Glu
                565                 570                 575 tat aca ttg tcc tct ttg act agt gac aca ttg tac atg gta cga atg    1776
Tyr Thr Leu Ser Ser Leu Thr Ser Asp Thr Leu Tyr Met Val Arg Met
        580                 585                 590 gca gca tac aca gat gaa ggt ggg aag gat ggt cca gaa ttc act ttt    1824
Ala Ala Tyr Thr Asp Glu Gly Gly Lys Asp Gly Pro Glu Phe Thr Phe
            595                 600                 605 act acc cca aag ttt gct caa gga gaa att gaa gcc ata gtc gtg cct    1872
Thr Thr Pro Lys Phe Ala Gln Gly Glu Ile Glu Ala Ile Val Val Pro
610                 615                 620 gtt tgc tta gca ttc cta ttg aca act ctt ctg gga gtg ctg ttc tgc    1920
Val Cys Leu Ala Phe Leu Leu Thr Thr Leu Leu Gly Val Leu Phe Cys
625                 630                 635                 640 ttt aat aag cga gac cta att aaa aaa cac atc tgg cct aat gtt cca    1968
Phe Asn Lys Arg Asp Leu Ile Lys Lys His Ile Trp Pro Asn Val Pro
                645                 650                 655 gat cct tca aag agt cat att gcc cag tgg tca cct cac act cct cca    2016
Asp Pro Ser Lys Ser His Ile Ala Gln Trp Ser Pro His Thr Pro Pro
        660                 665                 670 agg cac aat ttt aat tca aaa gat caa atg tat tca gat ggc aat ttc    2064
Arg His Asn Phe Asn Ser Lys Asp Gln Met Tyr Ser Asp Gly Asn Phe
            675                 680                 685 act gat gta agt gtt gtg gaa ata gaa gca aat gac aaa aag cct ttt    2112
Thr Asp Val Ser Val Val Glu Ile Glu Ala Asn Asp Lys Lys Pro Phe
690                 695                 700 cca gaa gat ctg aaa tta ttg gac ctg ttc aaa aag gaa aaa att aat    2160
Pro Glu Asp Leu Lys Leu Leu Asp Leu Phe Lys Lys Glu Lys Ile Asn
705                 710                 715                 720 act gaa gga cac agc agt ggt att ggg ggg tct tca tgc atg tca tct    2208
Thr Glu Gly His Ser Ser Gly Ile Gly Gly Ser Ser Cys Met Ser Ser
                725                 730                 735 tct agg cca agc att tct agc agt gat gaa aat gaa tct tca caa aac    2256
Ser Arg Pro Ser Ile Ser Ser Ser Asp Glu Asn Glu Ser Ser Gln Asn
        740                 745                 750 act tcg agc act gtc cag tat tct acc gtg gta cac agt ggc tac aga    2304
Thr Ser Ser Thr Val Gln Tyr Ser Thr Val Val His Ser Gly Tyr Arg
            755                 760                 765 cac caa gtt ccg tca gtc caa gtc ttc tca aga tcc gag tct acc cag    2352
His Gln Val Pro Ser Val Gln Val Phe Ser Arg Ser Glu Ser Thr Gln
770                 775                 780 ccc ttg tta gat tca gag gag cgg cca gaa gat cta caa tta gta gat    2400
Pro Leu Leu Asp Ser Glu Glu Arg Pro Glu Asp Leu Gln Leu Val Asp
785                 790                 795                 800 cat gta gat ggc ggt gat ggt att ttg ccc agg caa cag tac ttc aaa    2448
His Val Asp Gly Gly Asp Gly Ile Leu Pro Arg Gln Gln Tyr Phe Lys
                805                 810                 815 cag aac tgc agt cag cat gaa tcc agt cca gat att tca cat ttt gaa    2496
Gln Asn Cys Ser Gln His Glu Ser Ser Pro Asp Ile Ser His Phe Glu
        820                 825                 830
```

```
agg  tca  aag  caa  gtt  tca  tca  gtc  aat  gag  gaa  gat  ttt  gtt  aga  ctt    2544
Arg  Ser  Lys  Gln  Val  Ser  Ser  Val  Asn  Glu  Glu  Asp  Phe  Val  Arg  Leu
          835                 840                 845 aaa  cag  cag  att  tca  gat  cat  att  tca  caa  tcc  tgt  gga  tct  ggg  caa    2592
Lys  Gln  Gln  Ile  Ser  Asp  His  Ile  Ser  Gln  Ser  Cys  Gly  Ser  Gly  Gln
850                 855                 860 atg  aaa  atg  ttt  cag  gaa  gtt  tct  gca  gca  gat  gct  ttt  ggt  cca  ggt    2640
Met  Lys  Met  Phe  Gln  Glu  Val  Ser  Ala  Ala  Asp  Ala  Phe  Gly  Pro  Gly
865                 870                 875                 880 act  gag  gga  caa  gta  gaa  aga  ttt  gaa  aca  gtt  ggc  atg  gag  gct  gcg    2688
Thr  Glu  Gly  Gln  Val  Glu  Arg  Phe  Glu  Thr  Val  Gly  Met  Glu  Ala  Ala
          885                 890                 895 act  gat  gaa  ggc  atg  cct  aaa  agt  tac  tta  cca  cag  act  gta  cgg  caa    2736
Thr  Asp  Glu  Gly  Met  Pro  Lys  Ser  Tyr  Leu  Pro  Gln  Thr  Val  Arg  Gln
900                 905                 910 ggc  ggc  tac  atg  cct  cag  tga                                                  2757
Gly  Gly  Tyr  Met  Pro  Gln
          915

<210> SEQ ID NO 6
<211> LENGTH: 918
<212> TYPE: PRT
<213> ORGANISM: human

<400> SEQUENCE: 6

Met Leu Thr Leu Gln Thr Trp Val Val Gln Ala Leu Phe Ile Phe Leu
1               5                   10                  15

Thr Thr Glu Ser Thr Gly Glu Leu Leu Asp Pro Cys Gly Tyr Ile Ser
            20                  25                  30

Pro Glu Ser Pro Val Val Gln Leu His Ser Asn Phe Thr Ala Val Cys
        35                  40                  45

Val Leu Lys Glu Lys Cys Met Asp Tyr Phe His Val Asn Ala Asn Tyr
    50                  55                  60

Ile Val Trp Lys Thr Asn His Phe Thr Ile Pro Lys Glu Gln Tyr Thr
65                  70                  75                  80

Ile Ile Asn Arg Thr Ala Ser Ser Val Thr Phe Thr Asp Ile Ala Ser
                85                  90                  95

Leu Asn Ile Gln Leu Thr Cys Asn Ile Leu Thr Phe Gly Gln Leu Glu
            100                 105                 110

Gln Asn Val Tyr Gly Ile Thr Ile Ile Ser Gly Leu Pro Pro Glu Lys
        115                 120                 125

Pro Lys Asn Leu Ser Cys Ile Val Asn Glu Gly Lys Lys Met Arg Cys
    130                 135                 140

Glu Trp Asp Gly Gly Arg Glu Thr His Leu Glu Thr Asn Phe Thr Leu
145                 150                 155                 160

Lys Ser Glu Trp Ala Thr His Lys Phe Ala Asp Cys Lys Ala Lys Arg
                165                 170                 175

Asp Thr Pro Thr Ser Cys Thr Val Asp Tyr Ser Thr Val Tyr Phe Val
            180                 185                 190

Asn Ile Glu Val Trp Val Glu Ala Glu Asn Ala Leu Gly Lys Val Thr
        195                 200                 205

Ser Asp His Ile Asn Phe Asp Pro Val Tyr Lys Val Lys Pro Asn Pro
    210                 215                 220

Pro His Asn Leu Ser Val Ile Asn Ser Glu Glu Leu Ser Ser Ile Leu
225                 230                 235                 240

Lys Leu Thr Trp Thr Asn Pro Ser Ile Lys Ser Val Ile Ile Leu Lys
                245                 250                 255
```

-continued

```
Tyr Asn Ile Gln Tyr Arg Thr Lys Asp Ala Ser Thr Trp Ser Gln Ile
            260                 265                 270

Pro Pro Glu Asp Thr Ala Ser Thr Arg Ser Ser Phe Thr Val Gln Asp
        275                 280                 285

Leu Lys Pro Phe Thr Glu Tyr Val Phe Arg Ile Arg Cys Met Lys Glu
290                 295                 300

Asp Gly Lys Gly Tyr Trp Ser Asp Trp Ser Glu Glu Ala Ser Gly Ile
305                 310                 315                 320

Thr Tyr Glu Asp Arg Pro Ser Lys Ala Pro Ser Phe Trp Tyr Lys Ile
                325                 330                 335

Asp Pro Ser His Thr Gln Gly Tyr Arg Thr Val Gln Leu Val Trp Lys
            340                 345                 350

Thr Leu Pro Pro Phe Glu Ala Asn Gly Lys Ile Leu Asp Tyr Glu Val
        355                 360                 365

Thr Leu Thr Arg Trp Lys Ser His Leu Gln Asn Tyr Thr Val Asn Ala
370                 375                 380

Thr Lys Leu Thr Val Asn Leu Thr Asn Asp Arg Tyr Leu Ala Thr Leu
385                 390                 395                 400

Thr Val Arg Asn Leu Val Gly Lys Ser Asp Ala Ala Val Leu Thr Ile
                405                 410                 415

Pro Ala Cys Asp Phe Gln Ala Thr His Pro Val Met Asp Leu Lys Ala
            420                 425                 430

Phe Pro Lys Asp Asn Met Leu Trp Val Glu Trp Thr Thr Pro Arg Glu
        435                 440                 445

Ser Val Lys Lys Tyr Ile Leu Glu Trp Cys Val Leu Ser Asp Lys Ala
450                 455                 460

Pro Cys Ile Thr Asp Trp Gln Gln Glu Asp Gly Thr Val His Arg Thr
465                 470                 475                 480

Tyr Leu Arg Gly Asn Leu Ala Glu Ser Lys Cys Tyr Leu Ile Thr Val
                485                 490                 495

Thr Pro Val Tyr Ala Asp Gly Pro Gly Ser Pro Glu Ser Ile Lys Ala
            500                 505                 510

Tyr Leu Lys Gln Ala Pro Pro Ser Lys Gly Pro Thr Val Arg Thr Lys
        515                 520                 525

Lys Val Gly Lys Asn Glu Ala Val Leu Glu Trp Asp Gln Leu Pro Val
530                 535                 540

Asp Val Gln Asn Gly Phe Ile Arg Asn Tyr Thr Ile Phe Tyr Arg Thr
545                 550                 555                 560

Ile Ile Gly Asn Glu Thr Ala Val Asn Val Asp Ser Ser His Thr Glu
                565                 570                 575

Tyr Thr Leu Ser Ser Leu Thr Ser Asp Thr Leu Tyr Met Val Arg Met
            580                 585                 590

Ala Ala Tyr Thr Asp Glu Gly Gly Lys Asp Gly Pro Glu Phe Thr Phe
        595                 600                 605

Thr Thr Pro Lys Phe Ala Gln Gly Glu Ile Glu Ala Ile Val Val Pro
610                 615                 620

Val Cys Leu Ala Phe Leu Leu Thr Thr Leu Leu Gly Val Leu Phe Cys
625                 630                 635                 640

Phe Asn Lys Arg Asp Leu Ile Lys Lys His Ile Trp Pro Asn Val Pro
                645                 650                 655

Asp Pro Ser Lys Ser His Ile Ala Gln Trp Ser Pro His Thr Pro Pro
            660                 665                 670

Arg His Asn Phe Asn Ser Lys Asp Gln Met Tyr Ser Asp Gly Asn Phe
        675                 680                 685
```

```
Thr Asp Val Ser Val Val Glu Ile Glu Ala Asn Asp Lys Lys Pro Phe
    690                 695                 700
Pro Glu Asp Leu Lys Leu Leu Asp Leu Phe Lys Lys Glu Lys Ile Asn
705                 710                 715                 720
Thr Glu Gly His Ser Ser Gly Ile Gly Gly Ser Ser Cys Met Ser Ser
                725                 730                 735
Ser Arg Pro Ser Ile Ser Ser Ser Asp Glu Asn Glu Ser Ser Gln Asn
            740                 745                 750
Thr Ser Ser Thr Val Gln Tyr Ser Thr Val Val His Ser Gly Tyr Arg
        755                 760                 765
His Gln Val Pro Ser Val Gln Val Phe Ser Arg Ser Glu Ser Thr Gln
    770                 775                 780
Pro Leu Leu Asp Ser Glu Glu Arg Pro Glu Asp Leu Gln Leu Val Asp
785                 790                 795                 800
His Val Asp Gly Gly Asp Gly Ile Leu Pro Arg Gln Gln Tyr Phe Lys
                805                 810                 815
Gln Asn Cys Ser Gln His Glu Ser Ser Pro Asp Ile Ser His Phe Glu
            820                 825                 830
Arg Ser Lys Gln Val Ser Ser Val Asn Glu Glu Asp Phe Val Arg Leu
        835                 840                 845
Lys Gln Gln Ile Ser Asp His Ile Ser Gln Ser Cys Gly Ser Gly Gln
    850                 855                 860
Met Lys Met Phe Gln Glu Val Ser Ala Ala Asp Ala Phe Gly Pro Gly
865                 870                 875                 880
Thr Glu Gly Gln Val Glu Arg Phe Glu Thr Val Gly Met Glu Ala Ala
                885                 890                 895
Thr Asp Glu Gly Met Pro Lys Ser Tyr Leu Pro Gln Thr Val Arg Gln
            900                 905                 910
Gly Gly Tyr Met Pro Gln
        915

<210> SEQ ID NO 7
<211> LENGTH: 1662
<212> TYPE: DNA
<213> ORGANISM: human
<220> FEATURE:
<221> NAME/KEY: CDS
<222> LOCATION: (1)..(1662)
<223> OTHER INFORMATION:

<400> SEQUENCE: 7 atg gtt ctt gcc agc tct acc acc agc atc cac acc atg ctg ctc ctg      48
Met Val Leu Ala Ser Ser Thr Thr Ser Ile His Thr Met Leu Leu Leu
1               5                   10                  15 ctc ctg atg ctc ttc cac ctg gga ctc caa gct tca atc tcg gcg cgc      96
Leu Leu Met Leu Phe His Leu Gly Leu Gln Ala Ser Ile Ser Ala Arg
            20                  25                  30 cag gac tac aag gac gac gat gac aag acg cgc ctg aag gtc ttg cag     144
Gln Asp Tyr Lys Asp Asp Asp Asp Lys Thr Arg Leu Lys Val Leu Gln
        35                  40                  45 gag ccc acc tgc gtc tcc gac tac atg agc atc tct act tgc gag tgg     192
Glu Pro Thr Cys Val Ser Asp Tyr Met Ser Ile Ser Thr Cys Glu Trp
    50                  55                  60 aag atg aat ggt ccc acc aat tgc agc acc gag ctc cgc ctg ttg tac     240
Lys Met Asn Gly Pro Thr Asn Cys Ser Thr Glu Leu Arg Leu Leu Tyr
65                  70                  75                  80 cag ctg gtt ttt ctg ctc tcc gaa gcc cac acg tgt atc cct gag aac     288
Gln Leu Val Phe Leu Leu Ser Glu Ala His Thr Cys Ile Pro Glu Asn
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 85  |     |     |     |     | 90  |     |     |     |     | 95  |     |      |
| aac | gga | ggc | gcg | ggg | tgc | gtg | tgc | cac | ctg | ctc | atg | gat | gac | gtg | gtc | 336  |
| Asn | Gly | Gly | Ala | Gly | Cys | Val | Cys | His | Leu | Leu | Met | Asp | Asp | Val | Val |      |
|     |     |     | 100 |     |     |     |     | 105 |     |     |     |     | 110 |     |     |      |
| agt | gcg | gat | aac | tat | aca | ctg | gac | ctg | tgg | gct | ggg | cag | cag | ctg | ctg | 384  |
| Ser | Ala | Asp | Asn | Tyr | Thr | Leu | Asp | Leu | Trp | Ala | Gly | Gln | Gln | Leu | Leu |      |
|     | 115 |     |     |     |     | 120 |     |     |     |     | 125 |     |     |     |     |      |
| tgg | aag | ggc | tcc | ttc | aag | ccc | agc | gag | cat | gtg | aaa | ccc | agg | gcc | cca | 432  |
| Trp | Lys | Gly | Ser | Phe | Lys | Pro | Ser | Glu | His | Val | Lys | Pro | Arg | Ala | Pro |      |
| 130 |     |     |     |     | 135 |     |     |     |     | 140 |     |     |     |     |     |      |
| gga | aac | ctg | aca | gtt | cac | acc | aat | gtc | tcc | gac | act | ctg | ctg | ctg | acc | 480  |
| Gly | Asn | Leu | Thr | Val | His | Thr | Asn | Val | Ser | Asp | Thr | Leu | Leu | Leu | Thr |      |
| 145 |     |     |     |     | 150 |     |     |     |     | 155 |     |     |     |     | 160 |      |
| tgg | agc | aac | ccg | tat | ccc | cct | gac | aat | tac | ctg | tat | aat | cat | ctc | acc | 528  |
| Trp | Ser | Asn | Pro | Tyr | Pro | Pro | Asp | Asn | Tyr | Leu | Tyr | Asn | His | Leu | Thr |      |
|     |     |     | 165 |     |     |     |     | 170 |     |     |     |     | 175 |     |     |      |
| tat | gca | gtc | aac | att | tgg | agt | gaa | aac | gac | ccg | gca | gat | ttc | aga | atc | 576  |
| Tyr | Ala | Val | Asn | Ile | Trp | Ser | Glu | Asn | Asp | Pro | Ala | Asp | Phe | Arg | Ile |      |
|     |     |     | 180 |     |     |     |     | 185 |     |     |     |     | 190 |     |     |      |
| tat | aac | gtg | acc | tac | cta | gaa | ccc | tcc | ctc | cgc | atc | gca | gcc | agc | acc | 624  |
| Tyr | Asn | Val | Thr | Tyr | Leu | Glu | Pro | Ser | Leu | Arg | Ile | Ala | Ala | Ser | Thr |      |
|     | 195 |     |     |     |     | 200 |     |     |     |     | 205 |     |     |     |     |      |
| ctg | aag | tct | ggg | att | tcc | tac | agg | gca | cgg | gtg | agg | gcc | tgg | gct | cag | 672  |
| Leu | Lys | Ser | Gly | Ile | Ser | Tyr | Arg | Ala | Arg | Val | Arg | Ala | Trp | Ala | Gln |      |
| 210 |     |     |     |     | 215 |     |     |     |     | 220 |     |     |     |     |     |      |
| tgc | tat | aac | acc | acc | tgg | agt | gag | tgg | agc | ccc | agc | acc | aag | tgg | cac | 720  |
| Cys | Tyr | Asn | Thr | Thr | Trp | Ser | Glu | Trp | Ser | Pro | Ser | Thr | Lys | Trp | His |      |
| 225 |     |     |     | 230 |     |     |     |     | 235 |     |     |     |     | 240 |     |      |
| aac | tcc | tac | agg | gag | ccc | ttc | gag | cag | cac | gga | gaa | att | gaa | gcc | ata | 768  |
| Asn | Ser | Tyr | Arg | Glu | Pro | Phe | Glu | Gln | His | Gly | Glu | Ile | Glu | Ala | Ile |      |
|     |     |     | 245 |     |     |     |     | 250 |     |     |     |     | 255 |     |     |      |
| gtc | gtg | cct | gtt | tgc | tta | gca | ttc | cta | ttg | aca | act | ctt | ctg | gga | gtg | 816  |
| Val | Val | Pro | Val | Cys | Leu | Ala | Phe | Leu | Leu | Thr | Thr | Leu | Leu | Gly | Val |      |
|     |     |     | 260 |     |     |     |     | 265 |     |     |     |     | 270 |     |     |      |
| ctg | ttc | tgc | ttt | aat | aag | cga | gac | cta | att | aaa | aaa | cac | atc | tgg | cct | 864  |
| Leu | Phe | Cys | Phe | Asn | Lys | Arg | Asp | Leu | Ile | Lys | Lys | His | Ile | Trp | Pro |      |
|     | 275 |     |     |     |     | 280 |     |     |     |     | 285 |     |     |     |     |      |
| aat | gtt | cca | gat | cct | tca | aag | agt | cat | att | gcc | cag | tgg | tca | cct | cac | 912  |
| Asn | Val | Pro | Asp | Pro | Ser | Lys | Ser | His | Ile | Ala | Gln | Trp | Ser | Pro | His |      |
| 290 |     |     |     |     | 295 |     |     |     |     | 300 |     |     |     |     |     |      |
| act | cct | cca | agg | cac | aat | ttt | aat | tca | aaa | gat | caa | atg | tat | tca | gat | 960  |
| Thr | Pro | Pro | Arg | His | Asn | Phe | Asn | Ser | Lys | Asp | Gln | Met | Tyr | Ser | Asp |      |
| 305 |     |     |     |     | 310 |     |     |     |     | 315 |     |     |     |     | 320 |      |
| ggc | aat | ttc | act | gat | gta | agt | gtt | gtg | gaa | ata | gaa | gca | aat | gac | aaa | 1008 |
| Gly | Asn | Phe | Thr | Asp | Val | Ser | Val | Val | Glu | Ile | Glu | Ala | Asn | Asp | Lys |      |
|     |     |     | 325 |     |     |     |     | 330 |     |     |     |     | 335 |     |     |      |
| aag | cct | ttt | cca | gaa | gat | ctg | aaa | tta | ttg | gac | ctg | ttc | aaa | aag | gaa | 1056 |
| Lys | Pro | Phe | Pro | Glu | Asp | Leu | Lys | Leu | Leu | Asp | Leu | Phe | Lys | Lys | Glu |      |
|     |     |     | 340 |     |     |     |     | 345 |     |     |     |     | 350 |     |     |      |
| aaa | att | aat | act | gaa | gga | cac | agc | agt | ggt | att | ggg | ggg | tct | tca | tgc | 1104 |
| Lys | Ile | Asn | Thr | Glu | Gly | His | Ser | Ser | Gly | Ile | Gly | Gly | Ser | Ser | Cys |      |
|     | 355 |     |     |     |     | 360 |     |     |     |     | 365 |     |     |     |     |      |
| atg | tca | tct | tct | agg | cca | agc | att | tct | agc | agt | gat | gaa | aat | gaa | tct | 1152 |
| Met | Ser | Ser | Ser | Arg | Pro | Ser | Ile | Ser | Ser | Ser | Asp | Glu | Asn | Glu | Ser |      |
| 370 |     |     |     |     | 375 |     |     |     |     | 380 |     |     |     |     |     |      |
| tca | caa | aac | act | tcg | agc | act | gtc | cag | tat | tct | acc | gtg | gta | cac | agt | 1200 |
| Ser | Gln | Asn | Thr | Ser | Ser | Thr | Val | Gln | Tyr | Ser | Thr | Val | Val | His | Ser |      |
| 385 |     |     |     |     | 390 |     |     |     |     | 395 |     |     |     |     | 400 |      |
| ggc | tac | aga | cac | caa | gtt | ccg | tca | gtc | caa | gtc | ttc | tca | aga | tcc | gag | 1248 |
| Gly | Tyr | Arg | His | Gln | Val | Pro | Ser | Val | Gln | Val | Phe | Ser | Arg | Ser | Glu |      |

```
                         405                  410                     415
tct acc cag ccc ttg tta gat tca gag gag cgg cca caa gat cta caa     1296
Ser Thr Gln Pro Leu Leu Asp Ser Glu Glu Arg Pro Gln Asp Leu Gln
            420                 425                 430 tta gta gat cat gta gat ggc ggt gat ggt att ttg ccc agg caa cag     1344
Leu Val Asp His Val Asp Gly Gly Asp Gly Ile Leu Pro Arg Gln Gln
        435                 440                 445 tac ttc aaa cag aac tgc agt cag cat gaa tcc agt cca gat att tca     1392
Tyr Phe Lys Gln Asn Cys Ser Gln His Glu Ser Ser Pro Asp Ile Ser
    450                 455                 460 cat ttt gaa agg tca aag caa gtt tca tca gtc aat gag gaa gat ttt     1440
His Phe Glu Arg Ser Lys Gln Val Ser Ser Val Asn Glu Glu Asp Phe
465                 470                 475                 480 gtt aga ctt aaa cag cag att tca gat cat att tca caa tcc tgt gga     1488
Val Arg Leu Lys Gln Gln Ile Ser Asp His Ile Ser Gln Ser Cys Gly
                485                 490                 495 tct ggg caa atg aaa atg ttt cag gaa gtt tct gca gca gat gct ttt     1536
Ser Gly Gln Met Lys Met Phe Gln Glu Val Ser Ala Ala Asp Ala Phe
            500                 505                 510 ggt cca ggt act gag gga caa gta gaa aga ttt gaa aca gtt ggc atg     1584
Gly Pro Gly Thr Glu Gly Gln Val Glu Arg Phe Glu Thr Val Gly Met
        515                 520                 525 gag gct gcg act gat gaa ggc atg cct aaa agt tac tta cca cag act     1632
Glu Ala Ala Thr Asp Glu Gly Met Pro Lys Ser Tyr Leu Pro Gln Thr
    530                 535                 540 gta cgg caa ggc ggc tac atg cct cag tga                             1662
Val Arg Gln Gly Gly Tyr Met Pro Gln
545                 550

<210> SEQ ID NO 8
<211> LENGTH: 553
<212> TYPE: PRT
<213> ORGANISM: human

<400> SEQUENCE: 8

Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
            20                  25                  30

Gln Asp Tyr Lys Asp Asp Asp Lys Thr Arg Leu Lys Val Leu Gln
        35                  40                  45

Glu Pro Thr Cys Val Ser Asp Tyr Met Ser Ile Ser Thr Cys Glu Trp
    50                  55                  60

Lys Met Asn Gly Pro Thr Asn Cys Ser Thr Glu Leu Arg Leu Leu Tyr
65                  70                  75                  80

Gln Leu Val Phe Leu Leu Ser Glu Ala His Thr Cys Ile Pro Glu Asn
                85                  90                  95

Asn Gly Gly Ala Gly Cys Val Cys His Leu Leu Met Asp Asp Val Val
            100                 105                 110

Ser Ala Asp Asn Tyr Thr Leu Asp Leu Trp Ala Gly Gln Gln Leu Leu
        115                 120                 125

Trp Lys Gly Ser Phe Lys Pro Ser Glu His Val Lys Pro Arg Ala Pro
    130                 135                 140

Gly Asn Leu Thr Val His Thr Asn Val Ser Asp Thr Leu Leu Leu Thr
145                 150                 155                 160

Trp Ser Asn Pro Tyr Pro Pro Asp Asn Tyr Leu Tyr Asn His Leu Thr
                165                 170                 175

Tyr Ala Val Asn Ile Trp Ser Glu Asn Asp Pro Ala Asp Phe Arg Ile
```

```
                      180                 185                 190
Tyr Asn Val Thr Tyr Leu Glu Pro Ser Leu Arg Ile Ala Ala Ser Thr
                195                 200                 205

Leu Lys Ser Gly Ile Ser Tyr Arg Ala Arg Val Arg Ala Trp Ala Gln
            210                 215                 220

Cys Tyr Asn Thr Thr Trp Ser Glu Trp Ser Pro Ser Thr Lys Trp His
225                 230                 235                 240

Asn Ser Tyr Arg Glu Pro Phe Glu Gln His Gly Glu Ile Glu Ala Ile
                245                 250                 255

Val Val Pro Val Cys Leu Ala Phe Leu Leu Thr Thr Leu Leu Gly Val
            260                 265                 270

Leu Phe Cys Phe Asn Lys Arg Asp Leu Ile Lys Lys His Ile Trp Pro
        275                 280                 285

Asn Val Pro Asp Pro Ser Lys Ser His Ile Ala Gln Trp Ser Pro His
290                 295                 300

Thr Pro Pro Arg His Asn Phe Asn Ser Lys Asp Gln Met Tyr Ser Asp
305                 310                 315                 320

Gly Asn Phe Thr Asp Val Ser Val Val Glu Ile Glu Ala Asn Asp Lys
                325                 330                 335

Lys Pro Phe Pro Glu Asp Leu Lys Leu Leu Asp Leu Phe Lys Lys Glu
            340                 345                 350

Lys Ile Asn Thr Glu Gly His Ser Ser Gly Ile Gly Gly Ser Ser Cys
        355                 360                 365

Met Ser Ser Ser Arg Pro Ser Ile Ser Ser Ser Asp Glu Asn Glu Ser
370                 375                 380

Ser Gln Asn Thr Ser Ser Thr Val Gln Tyr Ser Thr Val Val His Ser
385                 390                 395                 400

Gly Tyr Arg His Gln Val Pro Ser Val Gln Val Phe Ser Arg Ser Glu
                405                 410                 415

Ser Thr Gln Pro Leu Leu Asp Ser Glu Glu Arg Pro Gln Asp Leu Gln
            420                 425                 430

Leu Val Asp His Val Asp Gly Gly Asp Gly Ile Leu Pro Arg Gln Gln
        435                 440                 445

Tyr Phe Lys Gln Asn Cys Ser Gln His Glu Ser Ser Pro Asp Ile Ser
    450                 455                 460

His Phe Glu Arg Ser Lys Gln Val Ser Ser Val Asn Glu Glu Asp Phe
465                 470                 475                 480

Val Arg Leu Lys Gln Gln Ile Ser Asp His Ile Ser Gln Ser Cys Gly
                485                 490                 495

Ser Gly Gln Met Lys Met Phe Gln Glu Val Ser Ala Ala Asp Ala Phe
            500                 505                 510

Gly Pro Gly Thr Glu Gly Gln Val Glu Arg Phe Glu Thr Val Gly Met
        515                 520                 525

Glu Ala Ala Thr Asp Glu Gly Met Pro Lys Ser Tyr Leu Pro Gln Thr
    530                 535                 540

Val Arg Gln Gly Gly Tyr Met Pro Gln
545                 550

<210> SEQ ID NO 9
<211> LENGTH: 1995
<212> TYPE: DNA
<213> ORGANISM: human
<220> FEATURE:
<221> NAME/KEY: CDS
<222> LOCATION: (1)..(1995)
<223> OTHER INFORMATION:
```

<400> SEQUENCE: 9

```
atg gtt ctt gcc agc tct acc acc agc atc cac acc atg ctg ctc ctg      48
Met Val Leu Ala Ser Ser Thr Thr Ser Ile His Thr Met Leu Leu Leu
1               5                   10                  15 ctc ctg atg ctc ttc cac ctg gga ctc caa gct tca atc tcg gcg cgc      96
Leu Leu Met Leu Phe His Leu Gly Leu Gln Ala Ser Ile Ser Ala Arg
            20                  25                  30 cag gac tac aag gac gac gat gac aag acg cgc cag gcg cct acg gaa     144
Gln Asp Tyr Lys Asp Asp Asp Asp Lys Thr Arg Gln Ala Pro Thr Glu
        35                  40                  45 act cag cca cct gtg aca aat ttg agt gtc tct gtt gaa aac ctc tgc     192
Thr Gln Pro Pro Val Thr Asn Leu Ser Val Ser Val Glu Asn Leu Cys
    50                  55                  60 aca gta ata tgg aca tgg aat cca ccc gag gga gcc agc tca aat tgt     240
Thr Val Ile Trp Thr Trp Asn Pro Pro Glu Gly Ala Ser Ser Asn Cys
65                  70                  75                  80 agt cta tgg tat ttt agt cat ttt ggc gac aaa caa gat aag aaa ata     288
Ser Leu Trp Tyr Phe Ser His Phe Gly Asp Lys Gln Asp Lys Lys Ile
                85                  90                  95 gct ccg gaa act cgt cgt tca ata gaa gta ccc ctg aat gag agg att     336
Ala Pro Glu Thr Arg Arg Ser Ile Glu Val Pro Leu Asn Glu Arg Ile
            100                 105                 110 tgt ctg caa gtg ggg tcc cag tgt agc acc aat gag agt gag aag cct     384
Cys Leu Gln Val Gly Ser Gln Cys Ser Thr Asn Glu Ser Glu Lys Pro
        115                 120                 125 agc att ttg gtt gaa aaa tgc atc tca ccc cca gaa ggt gat cct gag     432
Ser Ile Leu Val Glu Lys Cys Ile Ser Pro Pro Glu Gly Asp Pro Glu
    130                 135                 140 tct gct gtg act gag ctt caa tgc att tgg cac aac ctg agc tac atg     480
Ser Ala Val Thr Glu Leu Gln Cys Ile Trp His Asn Leu Ser Tyr Met
145                 150                 155                 160 aag tgt tct tgg ctc cct gga agg aat acc agt ccc gac act aac tat     528
Lys Cys Ser Trp Leu Pro Gly Arg Asn Thr Ser Pro Asp Thr Asn Tyr
                165                 170                 175 act ctc tac tat tgg cac aga agc ctg gaa aaa att cat caa tgt gaa     576
Thr Leu Tyr Tyr Trp His Arg Ser Leu Glu Lys Ile His Gln Cys Glu
            180                 185                 190 aac atc ttt aga gaa ggc caa tac ttt ggt tgt tcc ttt gat ctg acc     624
Asn Ile Phe Arg Glu Gly Gln Tyr Phe Gly Cys Ser Phe Asp Leu Thr
        195                 200                 205 aaa gtg aag gat tcc agt ttt gaa caa cac agt gtc caa ata atg gtc     672
Lys Val Lys Asp Ser Ser Phe Glu Gln His Ser Val Gln Ile Met Val
    210                 215                 220 aag gat aat gca gga aaa att aaa cca tcc ttc aat ata gtg cct tta     720
Lys Asp Asn Ala Gly Lys Ile Lys Pro Ser Phe Asn Ile Val Pro Leu
225                 230                 235                 240 act tcc cgt gtg aaa cct gat cct cca cat att aaa aac ctc tcc ttc     768
Thr Ser Arg Val Lys Pro Asp Pro Pro His Ile Lys Asn Leu Ser Phe
                245                 250                 255 cac aat gat gac cta tat gtg caa tgg gag aat cca cag aat ttt att     816
His Asn Asp Asp Leu Tyr Val Gln Trp Glu Asn Pro Gln Asn Phe Ile
            260                 265                 270 agc aga tgc cta ttt tat gaa gta gaa gtc aat aac agc caa act gag     864
Ser Arg Cys Leu Phe Tyr Glu Val Glu Val Asn Asn Ser Gln Thr Glu
        275                 280                 285 aca cat aat gtt ttc tac gtc caa gag gct aaa tgt gag aat cca gaa     912
Thr His Asn Val Phe Tyr Val Gln Glu Ala Lys Cys Glu Asn Pro Glu
    290                 295                 300 ttt gag aga aat gtg gag aat aca tct tgt ttc atg gtc cct ggt gtt     960
Phe Glu Arg Asn Val Glu Asn Thr Ser Cys Phe Met Val Pro Gly Val
```

```
Phe Glu Arg Asn Val Glu Asn Thr Ser Cys Phe Met Val Pro Gly Val
305                 310                 315                 320 ctt cct gat act ttg aac aca gtc aga ata aga gtc aaa aca aat aag    1008
Leu Pro Asp Thr Leu Asn Thr Val Arg Ile Arg Val Lys Thr Asn Lys
                325                 330                 335 tta tgc tat gag gat gac aaa ctc tgg agt aat tgg agc caa gaa atg    1056
Leu Cys Tyr Glu Asp Asp Lys Leu Trp Ser Asn Trp Ser Gln Glu Met
                340                 345                 350 agt ata ggt aag aag cgc aat tcc aca gga gaa att gaa gcc ata gtc    1104
Ser Ile Gly Lys Lys Arg Asn Ser Thr Gly Glu Ile Glu Ala Ile Val
            355                 360                 365 gtg cct gtt tgc tta gca ttc cta ttg aca act ctt ctg gga gtg ctg    1152
Val Pro Val Cys Leu Ala Phe Leu Leu Thr Thr Leu Leu Gly Val Leu
        370                 375                 380 ttc tgc ttt aat aag cga gac cta att aaa aaa cac atc tgg cct aat    1200
Phe Cys Phe Asn Lys Arg Asp Leu Ile Lys Lys His Ile Trp Pro Asn
385                 390                 395                 400 gtt cca gat cct tca aag agt cat att gcc cag tgg tca cct cac act    1248
Val Pro Asp Pro Ser Lys Ser His Ile Ala Gln Trp Ser Pro His Thr
                405                 410                 415 cct cca agg cac aat ttt aat tca aaa gat caa atg tat tca gat ggc    1296
Pro Pro Arg His Asn Phe Asn Ser Lys Asp Gln Met Tyr Ser Asp Gly
                420                 425                 430 aat ttc act gat gta agt gtt gtg gaa ata gaa gca aat gac aaa aag    1344
Asn Phe Thr Asp Val Ser Val Val Glu Ile Glu Ala Asn Asp Lys Lys
                435                 440                 445 cct ttt cca gaa gat ctg aaa tta ttg gac ctg ttc aaa aag gaa aaa    1392
Pro Phe Pro Glu Asp Leu Lys Leu Leu Asp Leu Phe Lys Lys Glu Lys
        450                 455                 460 att aat act gaa gga cac agc agt ggt att ggg ggg tct tca tgc atg    1440
Ile Asn Thr Glu Gly His Ser Ser Gly Ile Gly Gly Ser Ser Cys Met
465                 470                 475                 480 tca tct tct agg cca agc att tct agc agt gat gaa aat gaa tct tca    1488
Ser Ser Ser Arg Pro Ser Ile Ser Ser Ser Asp Glu Asn Glu Ser Ser
                485                 490                 495 caa aac act tcg agc act gtc cag tat tct acc gtg gta cac agt ggc    1536
Gln Asn Thr Ser Ser Thr Val Gln Tyr Ser Thr Val Val His Ser Gly
                500                 505                 510 tac aga cac caa gtt ccg tca gtc caa gtc ttc tca aga tcc gag tct    1584
Tyr Arg His Gln Val Pro Ser Val Gln Val Phe Ser Arg Ser Glu Ser
            515                 520                 525 acc cag ccc ttg tta gat tca gag gag cgg cca gaa gat cta caa tta    1632
Thr Gln Pro Leu Leu Asp Ser Glu Glu Arg Pro Glu Asp Leu Gln Leu
        530                 535                 540 gta gat cat gta gat ggc ggt gat ggt att ttg ccc agg caa cag tac    1680
Val Asp His Val Asp Gly Gly Asp Gly Ile Leu Pro Arg Gln Gln Tyr
545                 550                 555                 560 ttc aaa cag aac tgc agt cag cat gaa tcc agt cca gat att tca cat    1728
Phe Lys Gln Asn Cys Ser Gln His Glu Ser Ser Pro Asp Ile Ser His
                565                 570                 575 ttt gaa agg tca aag caa gtt tca tca gtc aat gag gaa gat ttt gtt    1776
Phe Glu Arg Ser Lys Gln Val Ser Ser Val Asn Glu Glu Asp Phe Val
                580                 585                 590 aga ctt aaa cag cag att tca gat cat att tca caa tcc tgt gga tct    1824
Arg Leu Lys Gln Gln Ile Ser Asp His Ile Ser Gln Ser Cys Gly Ser
                595                 600                 605 ggg caa atg aaa atg ttt cag gaa gtt tct gca gca gat gct ttt ggt    1872
Gly Gln Met Lys Met Phe Gln Glu Val Ser Ala Ala Asp Ala Phe Gly
        610                 615                 620 cca ggt act gag gga caa gta gaa aga ttt gaa aca gtt ggc atg gag    1920
```

-continued

```
Pro Gly Thr Glu Gly Gln Val Glu Arg Phe Glu Thr Val Gly Met Glu
625                 630                 635                 640 gct gcg act gat gaa ggc atg cct aaa agt tac tta cca cag act gta     1968
Ala Ala Thr Asp Glu Gly Met Pro Lys Ser Tyr Leu Pro Gln Thr Val
                645                 650                 655 cgg caa ggc ggc tac atg cct cag tga                                 1995
Arg Gln Gly Gly Tyr Met Pro Gln
                660
```

<210> SEQ ID NO 10
<211> LENGTH: 664
<212> TYPE: PRT
<213> ORGANISM: human

<400> SEQUENCE: 10

```
Met Val Leu Ala Ser Ser Thr Thr Ser Ile His Thr Met Leu Leu Leu
1               5                   10                  15

Leu Leu Met Leu Phe His Leu Gly Leu Gln Ala Ser Ile Ser Ala Arg
                20                  25                  30

Gln Asp Tyr Lys Asp Asp Asp Lys Thr Arg Gln Ala Pro Thr Glu
            35                  40                  45

Thr Gln Pro Pro Val Thr Asn Leu Ser Val Ser Val Glu Asn Leu Cys
        50                  55                  60

Thr Val Ile Trp Thr Trp Asn Pro Pro Glu Gly Ala Ser Ser Asn Cys
65                  70                  75                  80

Ser Leu Trp Tyr Phe Ser His Phe Gly Asp Lys Gln Asp Lys Lys Ile
                85                  90                  95

Ala Pro Glu Thr Arg Arg Ser Ile Glu Val Pro Leu Asn Glu Arg Ile
            100                 105                 110

Cys Leu Gln Val Gly Ser Gln Cys Ser Thr Asn Glu Ser Glu Lys Pro
        115                 120                 125

Ser Ile Leu Val Glu Lys Cys Ile Ser Pro Glu Gly Asp Pro Glu
    130                 135                 140

Ser Ala Val Thr Glu Leu Gln Cys Ile Trp His Asn Leu Ser Tyr Met
145                 150                 155                 160

Lys Cys Ser Trp Leu Pro Gly Arg Asn Thr Ser Pro Asp Thr Asn Tyr
                165                 170                 175

Thr Leu Tyr Tyr Trp His Arg Ser Leu Glu Lys Ile His Gln Cys Glu
            180                 185                 190

Asn Ile Phe Arg Glu Gly Gln Tyr Phe Gly Cys Ser Phe Asp Leu Thr
        195                 200                 205

Lys Val Lys Asp Ser Ser Phe Glu Gln His Ser Val Gln Ile Met Val
    210                 215                 220

Lys Asp Asn Ala Gly Lys Ile Lys Pro Ser Phe Asn Ile Val Pro Leu
225                 230                 235                 240

Thr Ser Arg Val Lys Pro Asp Pro Pro His Ile Lys Asn Leu Ser Phe
                245                 250                 255

His Asn Asp Asp Leu Tyr Val Gln Trp Glu Asn Pro Gln Asn Phe Ile
            260                 265                 270

Ser Arg Cys Leu Phe Tyr Glu Val Glu Val Asn Asn Ser Gln Thr Glu
        275                 280                 285

Thr His Asn Val Phe Tyr Val Gln Glu Ala Lys Cys Glu Asn Pro Glu
    290                 295                 300

Phe Glu Arg Asn Val Glu Asn Thr Ser Cys Phe Met Val Pro Gly Val
305                 310                 315                 320

Leu Pro Asp Thr Leu Asn Thr Val Arg Ile Arg Val Lys Thr Asn Lys
```

```
                325                 330                 335
Leu Cys Tyr Glu Asp Asp Lys Leu Trp Ser Asn Trp Ser Gln Glu Met
            340                 345                 350

Ser Ile Gly Lys Lys Arg Asn Ser Thr Gly Glu Ile Glu Ala Ile Val
        355                 360                 365

Val Pro Val Cys Leu Ala Phe Leu Leu Thr Thr Leu Leu Gly Val Leu
    370                 375                 380

Phe Cys Phe Asn Lys Arg Asp Leu Ile Lys Lys His Ile Trp Pro Asn
385                 390                 395                 400

Val Pro Asp Pro Ser Lys Ser His Ile Ala Gln Trp Ser Pro His Thr
                405                 410                 415

Pro Pro Arg His Asn Phe Asn Ser Lys Asp Gln Met Tyr Ser Asp Gly
            420                 425                 430

Asn Phe Thr Asp Val Ser Val Val Glu Ile Glu Ala Asn Asp Lys Lys
        435                 440                 445

Pro Phe Pro Glu Asp Leu Lys Leu Leu Asp Leu Phe Lys Lys Glu Lys
    450                 455                 460

Ile Asn Thr Glu Gly His Ser Ser Gly Ile Gly Gly Ser Ser Cys Met
465                 470                 475                 480

Ser Ser Ser Arg Pro Ser Ile Ser Ser Ser Asp Glu Asn Glu Ser Ser
                485                 490                 495

Gln Asn Thr Ser Ser Thr Val Gln Tyr Ser Thr Val Val His Ser Gly
            500                 505                 510

Tyr Arg His Gln Val Pro Ser Val Gln Val Phe Ser Arg Ser Glu Ser
        515                 520                 525

Thr Gln Pro Leu Leu Asp Ser Glu Glu Arg Pro Glu Asp Leu Gln Leu
    530                 535                 540

Val Asp His Val Asp Gly Gly Asp Gly Ile Leu Pro Arg Gln Gln Tyr
545                 550                 555                 560

Phe Lys Gln Asn Cys Ser Gln His Glu Ser Ser Pro Asp Ile Ser His
                565                 570                 575

Phe Glu Arg Ser Lys Gln Val Ser Ser Val Asn Glu Glu Asp Phe Val
            580                 585                 590

Arg Leu Lys Gln Gln Ile Ser Asp His Ile Ser Gln Ser Cys Gly Ser
        595                 600                 605

Gly Gln Met Lys Met Phe Gln Glu Val Ser Ala Ala Asp Ala Phe Gly
    610                 615                 620

Pro Gly Thr Glu Gly Gln Val Glu Arg Phe Glu Thr Val Gly Met Glu
625                 630                 635                 640

Ala Ala Thr Asp Glu Gly Met Pro Lys Ser Tyr Leu Pro Gln Thr Val
                645                 650                 655

Arg Gln Gly Gly Tyr Met Pro Gln
            660

<210> SEQ ID NO 11
<211> LENGTH: 41
<212> TYPE: DNA
<213> ORGANISM: Artificial Sequence
<220> FEATURE:
<223> OTHER INFORMATION: oligonucleotide primer

<400> SEQUENCE: 11
agctggcgcg ccaggcgcct acggaaactc agccacctgt g                           41

<210> SEQ ID NO 12
<211> LENGTH: 56
```

<212> TYPE: DNA
<213> ORGANISM: Artificial Sequence
<220> FEATURE:
<223> OTHER INFORMATION: oligonucleotide primer

<400> SEQUENCE: 12
caggcacgac tatggcttca atttctcctg tggaattgcg cttcttacct atactc      56

<210> SEQ ID NO 13
<211> LENGTH: 38
<212> TYPE: DNA
<213> ORGANISM: Artificial Sequence
<220> FEATURE:
<223> OTHER INFORMATION: oligonucleotide primer

<400> SEQUENCE: 13
ggagaaattg aagccatagt cgtgcctgtt tgcttagc      38

<210> SEQ ID NO 14
<211> LENGTH: 37
<212> TYPE: DNA
<213> ORGANISM: Artificial Sequence
<220> FEATURE:
<223> OTHER INFORMATION: oligonucleotide primer

<400> SEQUENCE: 14
acgtacgcgt tcactgaggc atgtagccgc cttgccg      37

<210> SEQ ID NO 15
<211> LENGTH: 27
<212> TYPE: DNA
<213> ORGANISM: Artificial Sequence
<220> FEATURE:
<223> OTHER INFORMATION: oligonucleotide primer

<400> SEQUENCE: 15
tgaaggtctt gcaagagccc acctgcg      27

<210> SEQ ID NO 16
<211> LENGTH: 28
<212> TYPE: DNA
<213> ORGANISM: Artificial Sequence
<220> FEATURE:
<223> OTHER INFORMATION: oligonucleotide primer

<400> SEQUENCE: 16
gtgctgctcg aagggctccc tgtaggag      28

<210> SEQ ID NO 17
<211> LENGTH: 39
<212> TYPE: DNA
<213> ORGANISM: Artificial Sequence
<220> FEATURE:
<223> OTHER INFORMATION: oligonucleotide primer

<400> SEQUENCE: 17
agctggcgcg cctgaaggtc ttgcaggagc ccacctgcg      39

<210> SEQ ID NO 18
<211> LENGTH: 56
<212> TYPE: DNA
<213> ORGANISM: Artificial Sequence
<220> FEATURE:
<223> OTHER INFORMATION: oligonucleotide primer

<400> SEQUENCE: 18
caggcacgac tatggcttca atttctccgt gctgctcgaa gggctccctg taggag      56

```
<210> SEQ ID NO 19
<211> LENGTH: 16
<212> TYPE: PRT
<213> ORGANISM: murine

<400> SEQUENCE: 19

Arg Ser Ser Lys Ser Leu Leu His Ser Asn Gly Ile Thr Tyr Leu Tyr
1               5                   10                  15

<210> SEQ ID NO 20
<211> LENGTH: 7
<212> TYPE: PRT
<213> ORGANISM: murine

<400> SEQUENCE: 20

Gln Met Ser Asn Leu Ala Ser
1               5

<210> SEQ ID NO 21
<211> LENGTH: 9
<212> TYPE: PRT
<213> ORGANISM: murine

<400> SEQUENCE: 21

Ala Gln Asn Leu Glu Leu Pro Phe Thr
1               5

<210> SEQ ID NO 22
<211> LENGTH: 10
<212> TYPE: PRT
<213> ORGANISM: murine

<400> SEQUENCE: 22

Gly Phe Thr Phe Ser Gly Tyr Gly Met Ser
1               5                   10

<210> SEQ ID NO 23
<211> LENGTH: 17
<212> TYPE: PRT
<213> ORGANISM: murine

<400> SEQUENCE: 23

Thr Ile Ser Gly Leu Gly Gly Tyr Thr Tyr Tyr Pro Asp Ser Val Lys
1               5                   10                  15

Gly

<210> SEQ ID NO 24
<211> LENGTH: 12
<212> TYPE: PRT
<213> ORGANISM: murine

<400> SEQUENCE: 24

Arg Phe Tyr Gly Asp Tyr Val Gly Ala Met Asp Tyr
1               5                   10

<210> SEQ ID NO 25
<211> LENGTH: 112
<212> TYPE: PRT
<213> ORGANISM: human

<400> SEQUENCE: 25

Asp Ile Gln Met Thr Gln Ser Pro Ser Ser Leu Ser Ala Ser Val Gly
1               5                   10                  15
```

Asp Arg Val Thr Ile Thr Cys Arg Ser Ser Lys Ser Leu Leu His Ser
            20                  25                  30

Asn Gly Ile Thr Tyr Leu Tyr Trp Tyr Gln Gln Lys Pro Gly Lys Ala
                35                  40                  45

Pro Lys Leu Leu Ile Tyr Gln Met Ser Asn Leu Ala Ser Gly Val Pro
    50                  55                  60

Ser Arg Phe Ser Gly Ser Gly Ser Gly Thr Asp Phe Thr Leu Thr Ile
65                  70                  75                  80

Ser Ser Leu Gln Pro Glu Asp Phe Ala Thr Tyr Tyr Cys Ala Gln Asn
                85                  90                  95

Leu Glu Leu Pro Phe Thr Phe Gly Gln Gly Thr Lys Val Glu Ile Lys
            100                 105                 110

<210> SEQ ID NO 26
<211> LENGTH: 121
<212> TYPE: PRT
<213> ORGANISM: human

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Gly Tyr
            20                  25                  30

Gly Met Ser Trp Val Arg Gln Ala Pro Gly Lys Gly Leu Glu Trp Val
        35                  40                  45

Ala Thr Ile Ser Gly Leu Gly Gly Tyr Thr Tyr Tyr Pro Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Arg Phe Tyr Gly Asp Tyr Val Gly Ala Met Asp Tyr Trp Gly
            100                 105                 110

Gln Gly Thr Leu Val Thr Val Ser Ser
        115                 120

<210> SEQ ID NO 27
<211> LENGTH: 112
<212> TYPE: PRT
<213> ORGANISM: murine

<400> SEQUENCE: 27

Asp Ile Leu Met Thr Gln Ala Ala Phe Ser Asn Pro Val Thr Leu Gly
1               5                   10                  15

Thr Ser Ala Ser Ile Ser Cys Arg Ser Ser Lys Ser Leu Leu His Ser
            20                  25                  30

Asn Gly Ile Thr Tyr Leu Tyr Trp Tyr Leu Gln Lys Pro Gly Gln Ser
                35                  40                  45

Pro Gln Leu Leu Ile Tyr Gln Met Ser Asn Leu Ala Ser Gly Val Pro
    50                  55                  60

Asp Arg Phe Ser Cys Ser Gly Ser Gly Thr Asp Phe Thr Leu Ser Ile
65                  70                  75                  80

Ser Arg Val Glu Ala Glu Asp Val Gly Phe Tyr Tyr Cys Ala Gln Asn
                85                  90                  95

Leu Glu Leu Pro Phe Thr Phe Gly Ser Gly Thr Lys Leu Glu Ile Glu
            100                 105                 110

```
<210> SEQ ID NO 28
<211> LENGTH: 121
<212> TYPE: PRT
<213> ORGANISM: murine

<400> SEQUENCE: 28

Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Gly Tyr
            20                  25                  30

Gly Met Ser Trp Val Arg Gln Thr Pro Glu Lys Arg Leu Glu Trp Val
            35                  40                  45

Ala Thr Ile Ser Gly Leu Gly Gly Tyr Thr Tyr Tyr Pro Asp Ser Val
        50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Asp Asp Thr Ala Phe Tyr Tyr Cys
                85                  90                  95

Ala Arg Arg Phe Tyr Gly Asp Tyr Val Gly Ala Met Asp Tyr Trp Gly
                100                 105                 110

Gln Gly Thr Ser Val Thr Val Ser Ser
            115                 120
```